(12) United States Patent
Lisanti et al.

(10) Patent No.: US 11,441,195 B2
(45) Date of Patent: Sep. 13, 2022

(54) ENERGETIC CANCER STEM CELLS (E-CSCS): A NEW HYPER-METABOLIC AND PROLIFERATIVE TUMOR CELL PHENOTYPE, DRIVEN BY MITOCHONDRIAL ENERGY

(71) Applicant: LUNELLA BIOTECH, INC., Ottawa (CA)

(72) Inventors: Michael P. Lisanti, Fulton, MD (US); Federica Sotgia, Fulton, MD (US); Marco Fiorillo, Manchester (GB)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 17/254,157

(22) PCT Filed: Jun. 19, 2019

(86) PCT No.: PCT/US2019/037860
§ 371 (c)(1),
(2) Date: Dec. 18, 2020

(87) PCT Pub. No.: WO2019/246173
PCT Pub. Date: Dec. 26, 2019

(65) Prior Publication Data
US 2021/0254177 A1 Aug. 19, 2021

Related U.S. Application Data

(60) Provisional application No. 62/731,561, filed on Sep. 14, 2018, provisional application No. 62/686,881, filed on Jun. 19, 2018.

(51) Int. Cl.
| | |
|---|---|
| A61K 49/00 | (2006.01) |
| C12Q 1/6886 | (2018.01) |
| A61K 31/03 | (2006.01) |
| A61K 31/519 | (2006.01) |
| A61K 45/06 | (2006.01) |

(52) U.S. Cl.
CPC ............ *C12Q 1/6886* (2013.01); *A61K 31/03* (2013.01); *A61K 31/519* (2013.01); *A61K 45/06* (2013.01); *C12Q 2600/106* (2013.01); *C12Q 2600/112* (2013.01); *C12Q 2600/118* (2013.01)

(58) Field of Classification Search
None
See application file for complete search history.

(56) References Cited

U.S. PATENT DOCUMENTS

| | | |
|---|---|---|
| 2005/0089518 A1 | 4/2005 | Clarke et al. |
| 2007/0254319 A1 | 11/2007 | Donnenberg et al. |
| 2010/0162416 A1 | 6/2010 | Krtolica et al. |
| 2010/0248291 A1 | 9/2010 | Radovanovic et al. |
| 2011/0110931 A1 | 5/2011 | Matsui |
| 2012/0071465 A1 | 3/2012 | Clement et al. |
| 2012/0237931 A1 | 9/2012 | Katz |
| 2014/0017721 A1 | 1/2014 | Botchkina |
| 2020/0032278 A1* | 1/2020 | Zhang .................... C12N 15/63 |

FOREIGN PATENT DOCUMENTS

WO 2011/109899 9/2011

OTHER PUBLICATIONS

Gloria Bonuccelli, et al., "Targeting cancer stem cell propagation with palbociclib, a CDK4/6 inhibitor: Telomerase drives tumor cell heterogeneity", Oncotarget, vol. 8, No. 6, 2017, pp. 9868-9884 (17 pages).
Marco Fioriilo, et al., ""Energetic" Cancer Stem Cells (e-CSCs): A New Hyper-Metabolic and Proliferative Tumor Cell Phenotype, Driven by Mitochondrial Energy", Frotiers in Oncology, vol. 8, Article 677, Feb. 2019, 16 pages.
Bela Ozsvari, et al., "Mitoriboscins: Mitochondrial-based therapeutics targeting cancer stem cells (CSCs), bacteria and pathogenic yeast", Oncotarget, vol. 8, No. 40, 2017, pp. 67457-67472 (16 pages).
International Search Report for PCT/US2019/037860 dated Nov. 21, 2019, 5 pages.
Written Opinion of the ISA for PCT/US2019/037860 dated Nov. 21, 2019, 13 pages.
Federica Sotgia et al: "Mitochondrial markers predict recurrence, metastasis and tamoxifen-resistance in breast cancer patients: Early detection of treatment failure with companion diagnostics", Oncotarget, vol. 8, No. 40, Sep. 15, 2017 (Sep. 15, 2017), pp. 68730-68745, XP055659674.
Marco Fiorillo et al: "Cancer Stem Cell Metabolism and Potential Therapeutic Targets", Oncotarget, vol. 8, No. 12, Mar. 21, 2017 (Mar. 21, 2017) pp. 20309-20327, XP055615711.
Lamb Rebecca et al: "Mitochondrial mass, a new metabolic biomarker for stem-like cancer cells: Understanding WNT/FGF-driven anabolic signaling", Oncotarget, vol. 6, No. 31, Oct. 13, 2015 (Oct. 13, 2015), pp. 30453-30471, XP055887101.
Farnie Gillian et al: "High mitochondrial mass identifies a subpopulation of stem-like cancer cells that are chemo-resistant", Oncotarget, vol. 6, No. 31, Oct. 13, 2015 (Oct. 13, 2015), pages Searched (IPC) 30472-30486, XP055803952.

(Continued)

*Primary Examiner* — Maria G Leavitt
(74) *Attorney, Agent, or Firm* — Nixon & Vanderhye, P.C.

(57) ABSTRACT

This disclosure describes the characteristics of the "energetic" cancer stem cell (e-CSC) phenotype. This distinct sub-population of cancer stem cells (CSCs) has a unique energetic profile compared to bulk CSCs, being more glycolytic, having higher mitochondrial mass and elevated oxidative metabolism. e-CSCs also show an increased capacity to undergo cell cycle progression, enhanced anchorage-independent growth, and ALDH-positivity. The e-CSC phenotype presents new targets for cancer therapeutics, and in particular the anti-oxidant response, mitochondrial energy production, and mitochondrial biogenesis of e-CSCs makes them highly susceptible to mitochondrial inhibitors that target e-CSC anti-oxidant response, mitochondrial energy production, and mitochondrial biogenesis. Gene products for e-CSCs are disclosed, as well as classes of mitochondrial inhibiting therapeutic agents. Also disclosed are methods for identifying and separating e-CSCs from bulk cell populations.

25 Claims, 30 Drawing Sheets

(56) References Cited

OTHER PUBLICATIONS

Bela Ozsvari et al: "Targeting flavin-containing enzymes eliminates cancer stem cells (CSC5), byinhibitingmitochondrialrespiration: VitaminB2 (Riboflavin) incancertherapy", Dec. 16, 2017 (Dec. 16, 2017), XP055887186.

Ernestina Marianna De Francesco et al: Vitamin C and Doxycycline: A synthetic lethal combination therapy targeting metabolic flexibility in cancer stem cells (CSC5) Oncotarget, vol. 8, No. 40, Sep. 15, 2017 (Sep. 15, 2017), pp. 67269-67286, XP055553187, United States ISSN: 1949-2553, DOI: 10. 18632/oncotarget .18428 * see abstract *.

Snyder Vusala et al: "Cancer Stem Cell Metabolism and Potential Therapeutic Targets", Frontiers in Oncology, vol. 8, Jun. 5, 2018 (Jun. 5, 2018), XP055887074, DOI: 10.3389/fonc.2018.00203 * the whole document *.

Song in Sung: "Mitochondria as therapeutic targets for cancer stem cells", World Journal of Stem Cells, vol. 7, No. 2, Jan. 1, 2015 (Jan. 1, 2015) p. 418, XP055887177, CN ISSN: 1948-0210, DOI: 10. 4252/wjsc.v7 .i2 .418 * the whole document *.

Ashton Thomas M. et al: "Oxidative Phosphorylation as an Emerging Target in Cancer Therapy", Clinical Cancer Research, vol. 24, No. 11, Feb. 2, 2018 (Feb. 2, 2018), pp. 2482-2490, XP055809091, US ISSN: 1078-0432, DOI: 10.1158/1078-0432. CCR-17-3070 Technical Fields * the whole document *.

* cited by examiner

ENERGETIC CANCER STEM CELLS (E-CSCS): A NEW HYPER-METABOLIC AND PROLIFERATIVE TUMOR CELL PHENOTYPE, DRIVEN BY MITOCHONDRIAL ENERGY

This application is the U.S. national phase of International Application No. PCT/US2019/037860 filed Jun. 19, 2019 which designated the U.S. and claims priority to U.S. Provisional Patent Application Nos. 62/731,561 filed Sep. 14, 2018, and 62/686,881 filed Jun. 19, 2018, the entire contents of each of which are hereby incorporated by reference.

FIELD

The present disclosure relates to cancer therapies, and more specifically to identifying, separating, and/or eradicating "energetic" cancer stem cells, a sub-population of cancer stem cells that are metabolically-active, hyper-proliferative, and critically-dependent on a 3D micro-environment.

BACKGROUND

Cancer stem cells (CSCs) are tumor-initiating cells (TICs) that are resistant to conventional cancer therapies, such as chemo-therapy and radiation treatment. As a consequence, CSCs are responsible for both tumor recurrence and distant metastasis, driving treatment failure and poor clinical outcomes in cancer patients. Therefore, innovative approaches are necessary to understand how to tackle the problem of CSCs. Mechanistically, this may be related to the ability of CSCs to survive and thrive under harsh conditions and different micro-environments. Because CSCs are an especially small sub-set of the tumor cell population, their metabolic and phenotypic properties have remained largely uncharacterized, until recently.

Moreover, CSCs are strikingly resilient and highly resistant to cellular stress, which allows them to undergo anchorage-independent growth, especially under conditions of low-attachment. As a consequence, they form 3D spheroids, which retain the properties of CSCs and stem cell progenitors. In contrast, when subjected to growth in suspension, most "bulk" cancer cells die, via anoikis—a specialized type of apoptosis. As such, the clonal propagation of a single CSC results in the production of a 3D spheroid and does not involve the self-aggregation of cancer cells. Therefore, 3D spheroid formation is a functional read-out for stemness in epithelial cancer cells and allows one to enrich for a population of epithelioid cells with a stem-like phenotype. These 3D spheroids are also known as mammospheres when they are prepared using breast cancer cells, such as MCF7, among others.

Previously, 3D spheroids have been generated from 2 distinct ER(+) cells lines (MCF7 and T47D) and subjected to unbiased label-free proteomics analysis. This work started the analysis of the phenotypic behavior of CSCs at a molecular level. The 3D spheroids were directly compared with monolayers of these cell lines and processed in parallel. This allowed for an identification of the proteomic features that are characteristic of the CSC phenotype in 3D spheroids, relative to monolayers. Based on this molecular analysis, mammospheres were observed to be significantly enriched in mitochondrial proteins. These mitochondrial-related proteins included molecules involved in beta-oxidation and ketone metabolism/re-utilization, mitochondrial biogenesis, electron transport, ADP/ATP exchange/transport, CoQ synthesis and ROS production, as well as the suppression of mitophagy. As such, increased mitochondrial protein synthesis or decreased mitophagy could allow the accumulation of mitochondrial mass in CSCs.

Given the increases in CSCs, mitochondrial mass is being considered as a new metabolic biomarker to purify CSCs. Using this overall approach, it has been observed that it was possible to significantly enrich CSC activity using only MitoTracker, as a single marker for both ER(+) (MCF7) and ER(−) (MDA-MB-231) breast cancer cell lines. Remarkably, MitoTracker-high cells were found to be chemo-resistant to Paclitaxel, exhibiting resistance to the Paclitaxel-induced DNA-damage response.

What is needed, however, is a method for identifying and characterizing the most prominent CSCs based on their metabolic profiles. Further, what is needed are methods for identifying and separating such metabolically "fit" CSCs from the bulk cell population, for further analysis and research. Additionally, what is needed are therapeutic strategies and agents that specifically target the "fittest" CSCs, and eliminate further cancer growth, including anchorage-independent growth, tumor recurrence, and distant metastasis.

BRIEF SUMMARY

This disclosure relates cancer therapies, and more specifically to identifying, separating, and/or eradicating "energetic" cancer stem cells (or "e-CSCs"), a sub-population of cancer stem cells that are metabolically-active, hyper-proliferative, and critically-dependent on a 3D micro-environment. Under the present approach, a gene signature is provided for detecting the presence of e-CSCs, predicting tumor recurrence, and/or predicting metastasis. The present approach also provides methods for purifying and collecting e-CSCs from a sample. In some embodiments, the present approach allows for treating cancer through eradicating e-CSCs (e.g., at least a significant portion of e-CSCs) in a mass, reducing the likelihood of metastasis and recurrence. In some embodiments, the present approach may be used in combination with, and/or to increase the effectiveness of, other therapies.

Cancer stem cells (CSCs) are now believed to be one of the main root causes of treatment failure in cancer patients world-wide. Mechanistically, this may be related to the ability of CSCs to survive and thrive under harsh conditions and different micro-environments. The inventors proposed the theory that CSCs might become resistant to conventional therapies by "boosting" ATP production using an elevated mitochondrial OXPHOS metabolism. Consistent with this view, a variety of mitochondrial inhibitors successfully blocked 3D tumor sphere formation, including i) FDA-approved antibiotics (doxycycline, tigecycline, azithromycin, pyrvinium pamoate, atovaquone, bedaquiline), ii) natural compounds (actinonin, CAPE, berberine, brutieridin and melitidin), as well as iii) experimental compounds (oligomycin and AR-C155858, an MCT1/2 inhibitor), among others.

The inventors identified a diverse metabolic heterogeneity in the CSC population. A flow-cytometry approach was used to metabolically fractionate the cancer cell population into "low-energy" and "high-energy" cell sub-populations. For this purpose, auto-fluorescence was used as an endogenous marker of their energetic state. In this context, auto-fluorescence was attributed to the endogenous flavin-containing metabolites, such as FAD, FMN and riboflavin (Vitamin B2). One area that was explored is whether growth in a 2D or 3D micro-environment affected their metabolic rate and stem-like properties.

The current results provide novel evidence for the existence of an "energetic" CSC phenotype, representing the "fittest" CSCs. Remarkably, these e-CSCs share three qualities: They are i) metabolically-active, ii) hyper-proliferative, and iii) critically-dependent on a 3D micro-environment.

This disclosure demonstrates that mitochondrial metabolism drives the anchorage-independent proliferation of CSCs. Two human breast cancer cell lines, MCF7 (ER(+)) and MDA-MB-468 (triple-negative), were used as model systems. To directly address the issue of metabolic heterogeneity in cancer, a new distinct sub-population of CSCs—"energetic" cancer stem cells (e-CSCs)—were identified and characterized, based solely on their energetic profile. This cellular phenotype presents new and valuable targets for anti-cancer therapeutics.

In a single step, an auto-fluorescent cell sub-population was isolated based on its high flavin-content, using flow-cytometry. The cells in this population were further subjected to a detailed phenotypic characterization for e-CSCs. As a result of the characterization, e-CSCs were more glycolytic, with higher mitochondrial mass and showed significantly elevated oxidative metabolism. Additionally, e-CSCs demonstrated an increased capacity to undergo cell cycle progression, as well as enhanced anchorage-independent growth and ALDH-positivity. Given the characterization, e-CSCs are susceptible to mitochondrial inhibitors, such as those described herein. For example, e-CSCs may be targeted by treatments with either i) OXPHOS inhibitors (e.g., Diphenyleneiodonium chloride, abbreviated DPI) or ii) CDK4/6 inhibitors (e.g., Ribociclib). Also, e-CSCs may be targeted by treatments with mitochondrial inhibitors, such as, for example, mitoriboscins, mitoketoscins, antimitoscins, repurposcins, mitoflavoscins, metformin, tetracycline family members, tigecycline family members, erythromycin family members, atovaquone, bedaquiline, vitamin c, stiripentol, caffeic acid phenyl ester (CAPE), and berberine.

Finally, two distinct phenotypic sub-types of e-CSCs have been identified, depending on whether they were grown as 2D-monolayers or as 3D-spheroids. Remarkably, under 3D anchorage-independent growth conditions, e-CSCs were strictly dependent on oxidative mitochondrial metabolism. Unbiased proteomics analysis demonstrated the up-regulation of gene products specifically related to the anti-oxidant response, mitochondrial energy production, and mitochondrial biogenesis. These gene products may be used as companion biomarkers in detecting and treating e-CSCs in a cancer, as described more fully below. Further, e-CSCs are vulnerable to mitochondrial inhibiting therapeutic agents that disrupt the energetic profile and directly target and eliminate the "fittest" e-CSCs. These results have important implications for using e-CSCs, especially those derived from 3D-spheroids, i) in tumor tissue bio-banking and ii) as a new cellular platform for drug development.

It should be appreciated that the present approach may be practiced through numerous embodiments. For example, some embodiments may take the form of methods for identifying and treating e-CSCs in a cancer. A biological sample of the cancer may be obtained. This could be, for instance, tissue from a tumor, blood, urine, saliva, and a metastatic lesion, as non-limiting examples. The expression level(s) of at least one member of the e-CSC gene signature in the sample may be determined. The e-CSC gene signature described herein includes NQO1, ALDH5A1, TXNR and RRM2. In some embodiments, the expression of each gene in the e-CSC gene signature may be measured. It should be appreciated that expression levels may be determined using methods known in the art. The determined expression level(s) may be compared to a threshold level for the at least one member of the e-CSC gene signature. A pharmaceutically effective amount of at least one of an OXPHOS inhibitor and a CDK4/6 inhibitor may be administered if the determined level exceeds the threshold level. For example, a differential expression level may be obtained, using as the threshold data for a population of cancer survivors that did not experience one or more of distant metastasis, tumor recurrence, and treatment failure. In some embodiments, the administration may be indicated if the quotient of the determined level divided by the threshold level exceeds an amount, such as, for example, about 1.2, or in some embodiments, about 2.0. Measurement error may be factored into this quotient, such as, for example, ±0.05 or ±0.10.

Some embodiments of the present approach may take the form of methods for predicting and treating tumor recurrence in a cancer. In some embodiments, the cancer exists in a tumor that has been treated with hormone therapy, such as breast cancer. The cancer may be, for example, a benign lesion, a pre-malignant lesion, a malignant lesion, or a metastatic lesion. A biological sample of the cancer may be obtained, and an assay may be performed to detect the presence of e-CSCs in the biological sample. A pharmaceutically effective amount of at least one of an OXPHOS inhibitor and a CDK4/6 inhibitor may be administered if e-CSCs are detected in the biological sample. The assay to detect the presence of e-CSCs in the biological sample may include determining, or having determined, a level of expression in the biological sample of at least one member of the e-CSC gene signature, comparing the determined level to a threshold level for the at least one member, and classifying the biological sample as having e-CSCs present if the determined level exceeds the threshold level.

Some embodiments may take the form of a method for predicting and treating metastasis in a cancer. The cancer may be, for example, breast cancer. A biological sample of the cancer may be obtained, an assay may be performed to detect the presence of e-CSCs in the biological sample, and a pharmaceutically effective amount of at least one of an OXPHOS inhibitor and a CDK4/6 inhibitor may be administered if e-CSCs are detected in the biological sample. The assay to detect the presence of e-CSCs in the biological sample may include determining, or having determined, a level of expression in the biological sample of at least one member of the e-CSC gene signature, comparing the determined level to a threshold level for the at least one member, and classifying the biological sample as having e-CSCs present if the determined level exceeds the threshold level.

Some embodiments may take the form of methods for treating cancer having one or more e-CSCs. A biological sample of the cancer may be obtained, an assay may be performed to detect the presence of e-CSCs in the biological sample, and a pharmaceutically effective amount of at least one of an OXPHOS inhibitor and a CDK4/6 inhibitor may be administered if e-CSCs are detected in the biological sample. The assay to detect the presence of e-CSCs in the biological sample may include determining, or having determined, a level of expression in the biological sample of at least one member of the e-CSC gene signature, comparing the determined level to a threshold level for the at least one member, and classifying the biological sample as having e-CSCs present if the determined level exceeds the threshold level.

The e-CSC therapeutic agent(s) administered may vary between embodiments. For example, in some embodiments the therapeutic agent may be or include diphenyleneiodonium chloride (DPI). In some embodiments, the therapeutic agent may be or include Ribociclib. Examples of other therapeutic agents include, but are not limited to, atoravaquone, irinotecan, sorafenib, niclosamide, berberine chloride, Abemaciclib, and Palbociclib. It should be appreciated that in some embodiments, more than one OXPHOS inhibitor and/or more than one CDK4/6 inhibitor may be used. It should be appreciated that the e-CSC therapeutic agent(s) may be administered with (e.g., before, concurrently, or in close temporal proximity) other cancer therapies, including hormone therapy, radiation therapy, photodynamic therapy, chemotherapy, among others. The e-CSC therapeutic agent(s) may be used to increase the effectiveness of another cancer therapy, such as through reducing treatment resistance, increasing sensitivity to a treatment, and/or eradicating e-CSCs that would otherwise cause further propagation, metastasis, and/or recurrence. In some embodiments, a mitochondrial inhibitor may be administered in with (e.g., before, concurrently, or in close temporal proximity) the e-CSC therapeutic agent(s). Examples of mitochondrial inhibitors include, but are not limited to, a mitoriboscin, a mitoketoscin, a antimitoscin, a repurposcin, a mitoflavoscin, metformin, a tetracycline family member, a tigecycline family member, a erythromycin family member, atovaquone, bedaquiline, vitamin c, stiripentol, caffeic acid phenyl ester (CAPE), and berberine.

Some embodiments of the present approach may take the form of methods for identifying and purifying e-CSCs in a sample, such as a biological sample (e.g., tumor tissue, blood, etc.). The auto-fluorescent signal of cells in the sample may be measured, and an upper range of measured auto-fluorescent signals may be identified. Cells having an auto-fluorescent signal within the upper range of measured auto-fluorescent signals may be identified. In some embodiments, the upper range of measured auto-fluorescent signals is approximately the top 5% of measured auto-fluorescent signals, it should be appreciated that the upper range may vary, such as, for example, the top 10%, the top 7%, the top 4%, the top 1%, etc. In some embodiments, the identified cells may be sorted and collected. Sorting and collecting may occur through, for example, fluorescence-activated cell sorting.

In some embodiments, a single-cell suspension may be formed from the sample, and the auto-fluorescent signal of cells in the sample may be measured through the auto-fluorescent signal of cells in the suspension. It should be appreciated that auto-fluorescent signal may be measured through flow cytometry, as is known in the art, and that auto-fluorescence may be attributed to the endogenous flavin-containing metabolites, such as FAD, FMN and riboflavin. Some embodiments may include measuring ALDH activity of identified cells. Some embodiments may include measuring anchorage-independent growth of the identified cells. Some embodiments may include measuring the mitochondrial mass of the identified cells. Some embodiments may include measuring the glycolytic and oxidative mitochondrial metabolism of the identified cells. Some embodiments may include measuring the cell cycle progression and proliferative rate of the identified cells. Some embodiments may include measuring the poly-ploidy of the identified cells.

Further embodiments of the present approach may be recognized by those having ordinary skill in the art, having reviewed the following detailed description.

DESCRIPTION OF THE DRAWINGS

FIG. 2A shows an embodiment of an apparatus for e-CSC refinement and characterization, and FIGS. 2B and 2C show demonstrative flow-cytometry results.

DESCRIPTION

Figure 1:
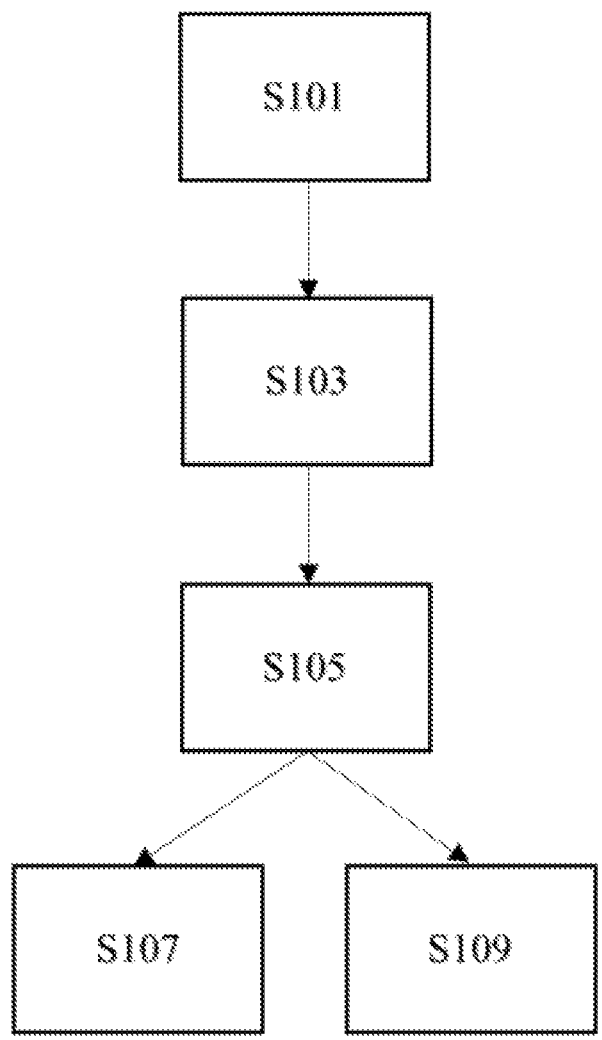
FIG. 1 shows a method for detecting, separating, and purifying e-CSCs.

The following description includes the currently contemplated modes of carrying out exemplary embodiments of the present approach. The following description is not to be taken in a limiting sense, and is made merely for the purpose of illustrating the general principles of the invention.

As described herein, the present approach relates to identifying, purifying, and collecting a hyper-proliferative cell sub-population of breast CSCs, by using an endogenous marker of energy-metabolism, namely, flavin-derived auto-fluorescence. The present approach may take various forms, depending on the embodiment. For example, under the present approach, a gene signature is provided for detecting the presence of e-CSCs, predicting tumor recurrence, and/or predicting metastasis. The present approach also allows for purifying and collecting e-CSCs from a sample. In some embodiments, the present approach allows for treating cancer through targeting and/or eradicating e-CSCs in a mass.

In addition to having a hyper-proliferative phenotype, e-CSCs showed progressive increases in stemness markers (e.g., ALDH activity and mammosphere-forming activity), a highly elevated mitochondrial mass, as well as increased glycolytic and mitochondrial activity. Moreover, the 3D sub-type of e-CSCs is strictly dependent on mitochondria, for cell propagation. Thus, under the present approach, the anchorage-independent propagation e-CSCs, derived from 3D-spheroids, may be specifically targeted with an OXPHOS inhibitor (such as, for example, DPI) to inhibit mitochondrial biogenesis, and/or a CDK4/6 inhibitor (such as, for example, Ribociclib) to inhibit cell proliferation.

Mechanistically, there are at least 2 different classes of e-CSCs that are metabolically distinct. As used herein, M-H refers to "monolayer-high" cells, and S-H refers to "spheroid-high" cells. The classification depends on whether the cells are grown in a 2D-monolayer or a 3D-spheroid micro-environment. A metabolic-switch occurs, likely during the transition from anchorage-dependent to anchorage-independent growth. This represents a metabolic shift from a glycolytic to a more oxidative mitochondrial phenotype. More specifically, in 2D-monolayer cultures, and as discussed in more detail below, 100 nM DPI increased the number M-H cells by ~7.5-fold over a 5-day period. In contrast, DPI, at exactly the same concentration, almost completely inhibited 3D-mammosphere formation, resulting in a population of anchorage-independent single live cells that were ~60% depleted of S-H cells. Therefore, the same mitochondrial OXPHOS inhibitor (DPI) had completely opposite effects, depending on the 2D vs. 3D micro-environment of the e-CSCs. These results experimentally imply that M-H cell propagation in 2D-monolayers is driven by glycolysis, while the propagation of S-H cells in 3D-spheroids is driven by mitochondrial OXPHOS. Importantly, this suggests that a critical metabolic-switch is occurring, between the M-H and S-H CSC phenotypes, specifically altering their metabolic requirements.

This 2D-to-3D transition, or "epithelial-mesenchymal-transition (EMT)" is thought to be a more mesenchymal phenotype. In support of this notion, ALDH activity was progressively increased and was at its highest levels in e-CSCs derived from the 3D-spheroids, nearly 9-fold increased, directly supporting the assertions of the present approach. Importantly, ALDH activity is an established functional biomarker of the EMT and "boosts" the production of energy-rich NAD(P)H.

The identification of this unique, energy-driven, cancer cell sub-population will undoubtedly provide new opportunities for i) bio-banking and ii) new drug screening, as well as iii) the identification of novel metabolic targets, for the prevention of tumor recurrence and inhibiting the spread of metastatic disease.

Two human breast cancer cell lines, MCF7 and MDA-MB-468, were used as model systems, to dissect the role of metabolic heterogeneity in tumorigenesis. Results with MCF7 cells are shown in FIGS. 2-8, Tables 1-6, and results with MDA-MB-468 cells are included in FIGS. 9-11. MCF7 cells are ER(+), while MDA-MB-468 cells are triple-negative. Quantitatively similar results were obtained with both model cell lines. Table 1, below, summarizes cell cycle phase data for cell populations of MCF7-derived e-CSCs. Averages are shown from 4 independent experiments. Abbreviations used: M-L, monolayer-low; M-H, monolayer-high; S-L, spheroid-low; S-H, spheroid-high.

TABLE 1

MCF7-derived e-CSCs cells demonstrate increased cell cycle progression.

|  | 2D-Monolayers (M) | | 3D-Spheroids (S) | |
| --- | --- | --- | --- | --- |
| CC-Phase (%) | M-L | M-H | S-L | S-H |
| G0/G1 | 81.25 | 53.23 | 61.50 | 37.32 |
| S-phase | 3.92 | 11.43 | 6.72 | 10.60 |
| G2/M | 8.53 | 21.23 | 11.72 | 32.43 |
| Polyploid | 3.71 | 10.74 | 9.03 | 17.13 |

Table 2, below, shows cell cycle data for cell populations from MDA-MB-468 e-CSCs. As with the MCF7 e-CSCs, these also demonstrate increased cell cycle progression. Table 3, also below, shows ALDH activity changes. The averages shown in both Tables 2 and 3 are from at least 3 independent experiments.

TABLE 2

MDA-MB-468 e-CSCs demonstrate increased cell cycle progression.

|  | 2D-Monolayers (M) | | 3D-Spheroids (S) | |
| --- | --- | --- | --- | --- |
| CC-Phase (%) | M-L | M-H | S-L | S-H |
| G0/G1 | 78.95 | 51.20 | 64.05 | 34.75 |
| S-phase | 2.96 | 12.18 | 9.03 | 18.10 |
| G2/M | 7.65 | 23.73 | 13.35 | 32.89 |
| Polyploid | 5.30 | 9.93 | 7.47 | 12.24 |

TABLE 3

MCF7-derived e-CSCs have increased ALDH activity.

| 2D-Monolayers (M) | | 3D-Spheroids (S) | |
| --- | --- | --- | --- |
| M-L | M-H | S-L | S-H |
| 0.52% | 1.03% (1.98x) | 2.13% (4.09x) | 4.59% (8.83x) |

The next series of analyses determined whether mitochondria may function as the metabolic "engines" to drive cellular hyper-proliferation in CSCs and, ultimately, anchorage-independent growth, leading to tumor recurrence and metastasis. The analysis also investigated whether two or more sub-populations of CSCs exist, depending on whether the cells are grown as 2D-monolayers or as 3D-spheroids). Cell auto-fluorescence was used as an endogenous marker of cellular energy metabolism, which directly reflects cellular content of flavin-containing compounds (FAD, FMN and riboflavin (Vitamin B2)), which are all high-energy cell metabolites.

FIG. 1 shows a method for detecting, separating, and purifying e-CSCs according to the present approach. The method is described in connection with e-CSCs from MCF7 cells, but it should be appreciated that the method may be applied to cells from other cancer types. First, at S101, single cell suspensions of MCF7 cells were prepared. Then, at S103, the MCF7 cells were subjected to metabolic fractionation by flow cytometry to isolate CSCs. The flow cytometry was based on the endogenous auto-fluorescence (AF) of Flavin adenine dinucleotide/Flavin mononucleotide (FAD/FMN) high-energy metabolites. The designator AF(+) refers to cells having high levels of FAD/FMN. The high (H) and low (L) sub-populations of AF cells were then collected from MCF7 cells at S105, and then grown either as i) 2D-monolayers (S107) or ii) 3D-spheroids (S109) using methods known in the art. The "high-energy" AF(+) cells were then designated as either e-CSCs (2D) and e-CSCs (3D).

With respect to the data described herein, 2D-monolayers and 3D-spheroids were first collected and used to prepare single-cell suspensions. These suspensions were then subjected to flow-cytometry to isolate cells based on their auto-fluorescent properties. Briefly, the "Low-(L)" and "High-(H)" auto-fluorescent cell sub-populations were selected by gating, within the auto-fluorescence signal. Only cells with the least (bottom 5%) or the most (top 5%) auto-fluorescent signal were collected. Both the "Low" and "High" sub-populations of auto-fluorescent cells, generated from either 2D-monolayers (M-L vs. M-H) or 3D-spheroids (S-L vs. S-H) were then subjected to a detailed phenotypic characterization and separation. The M-H ("monolayer-high") and S-H ("spheroid-high") cell sub-populations were predicted to be the most energetic, based on their high (H) flavin-content.

Figure 2A:
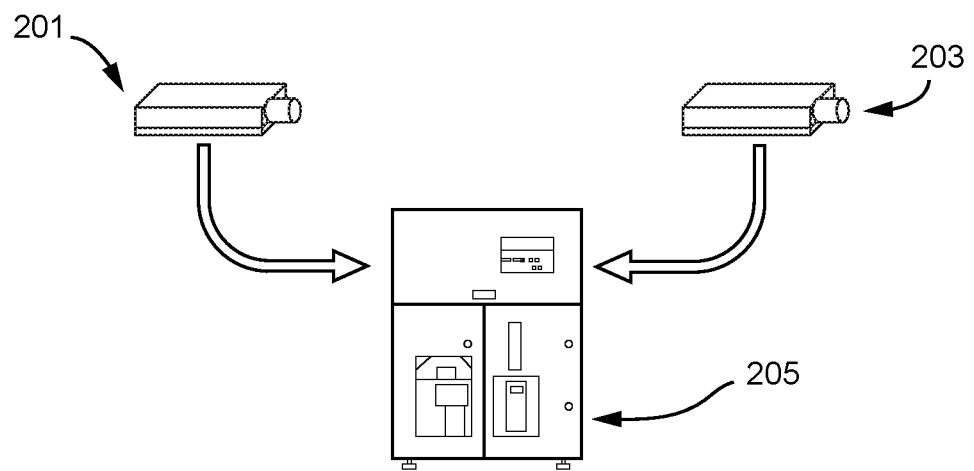
FIGS. 2A-2C relate to refinement and characterization of e-CSCs.
Figure 2B:
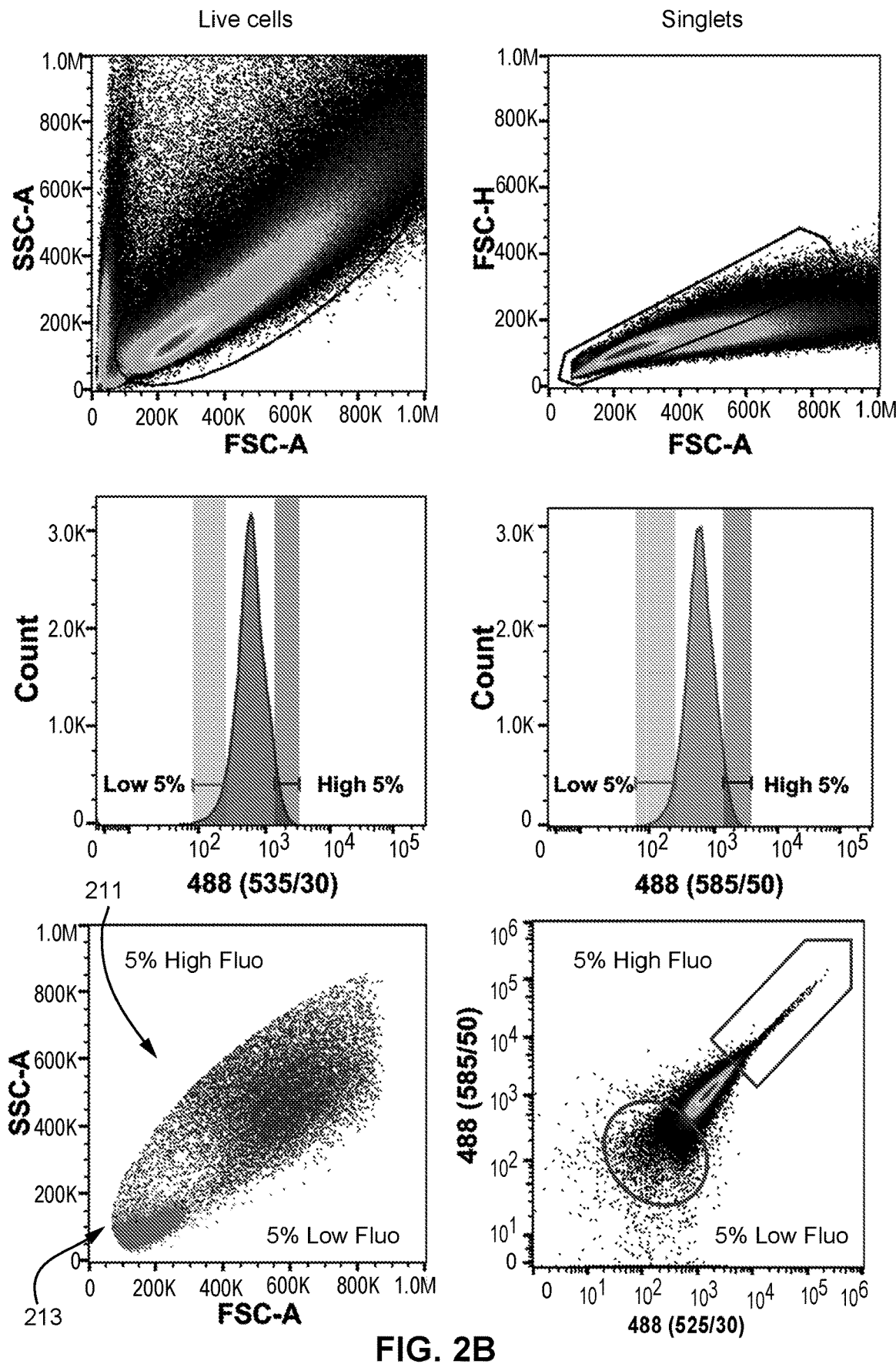
Figure 2C:
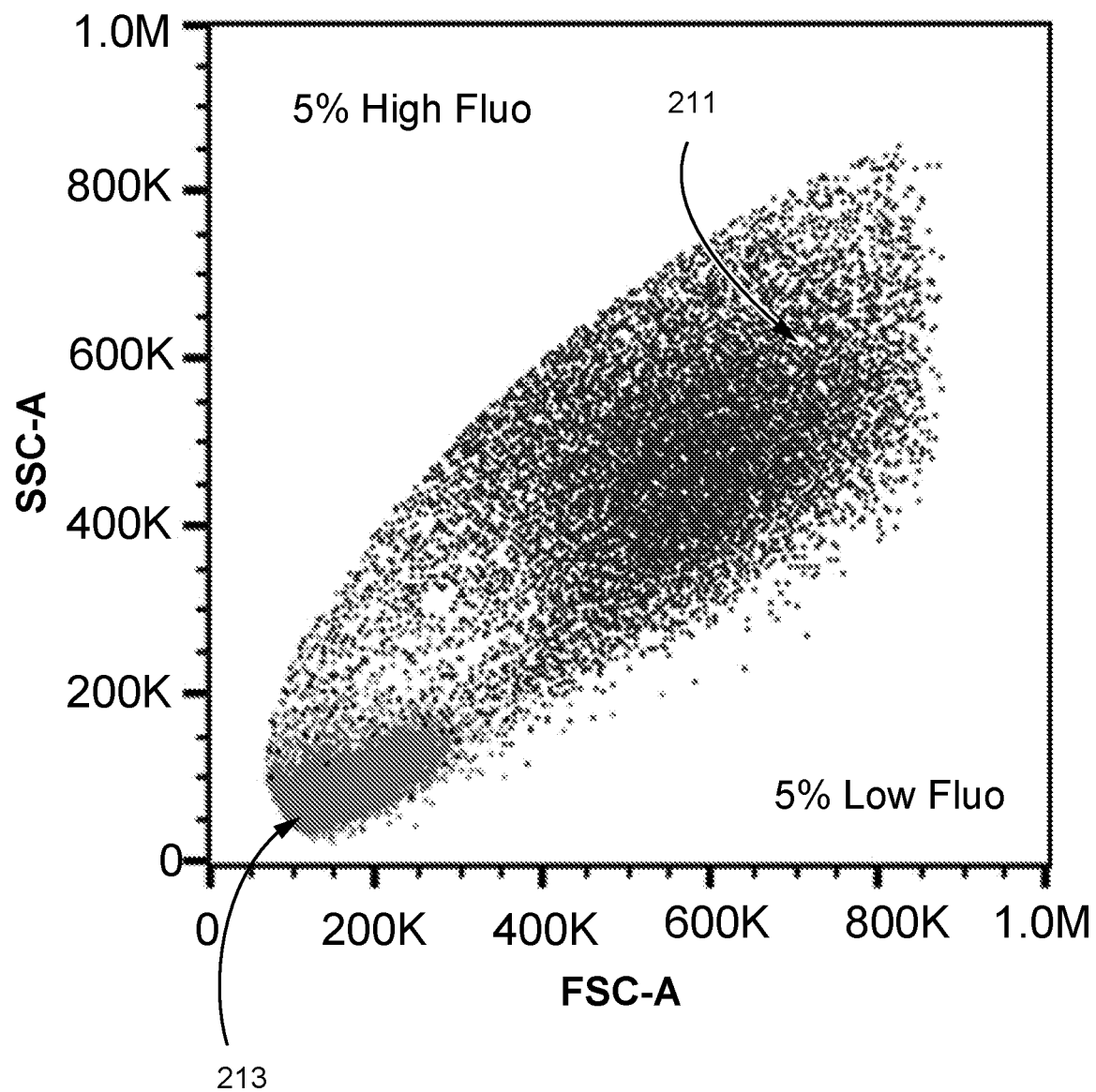

FIG. 2A shows an example of further e-CSC separation and purification method of the present approach. For the data discussed below, both MCF7 cells and MDA-MB-468 cells were used. In this illustration, the cells grown as 2D monolayer attached cells 201 and 3D spheroid non-attached cells 203 were collected and dissociated into a single-cell suspension before flow-cytometry sorting through a SONY SH800 cell sorter 205. The flow-cytometry results are shown in FIG. 2B; the left column shows live cells, and the right column shows singlets. FIG. 2C is an enlargement of the forward-scatter and side-scatter data, and was originally in color but has been reduced to gray-scale for this application. Based on the forward-scatter and side-scatter analysis of single cells, highly auto-fluorescent cells 211 were clearly larger in size, than cells with low auto-fluorescence 213.

Figure 3A:
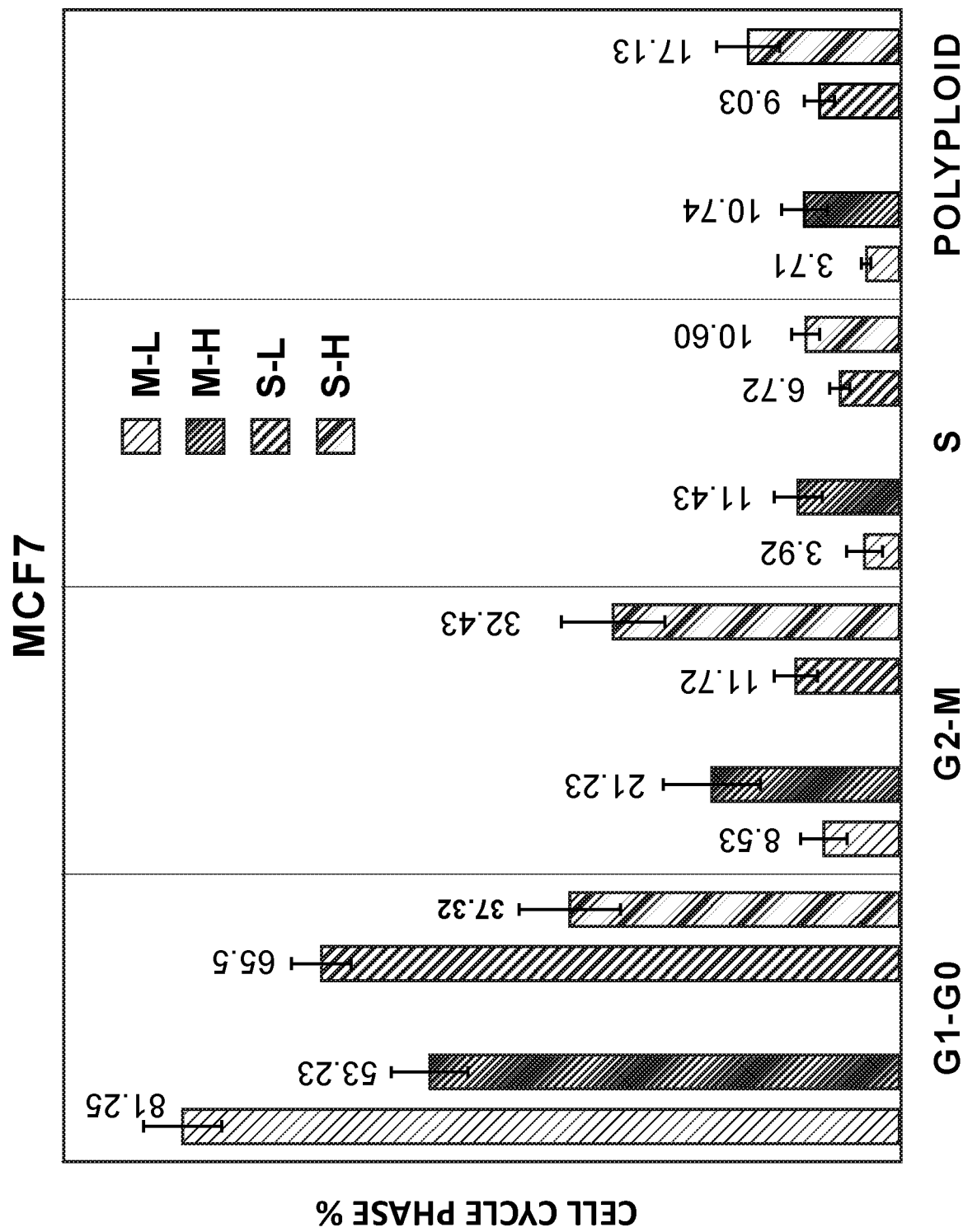
FIG. 3A shows cell cycle profiles for different cell sub-populations of MCF7.
Figure 3B:
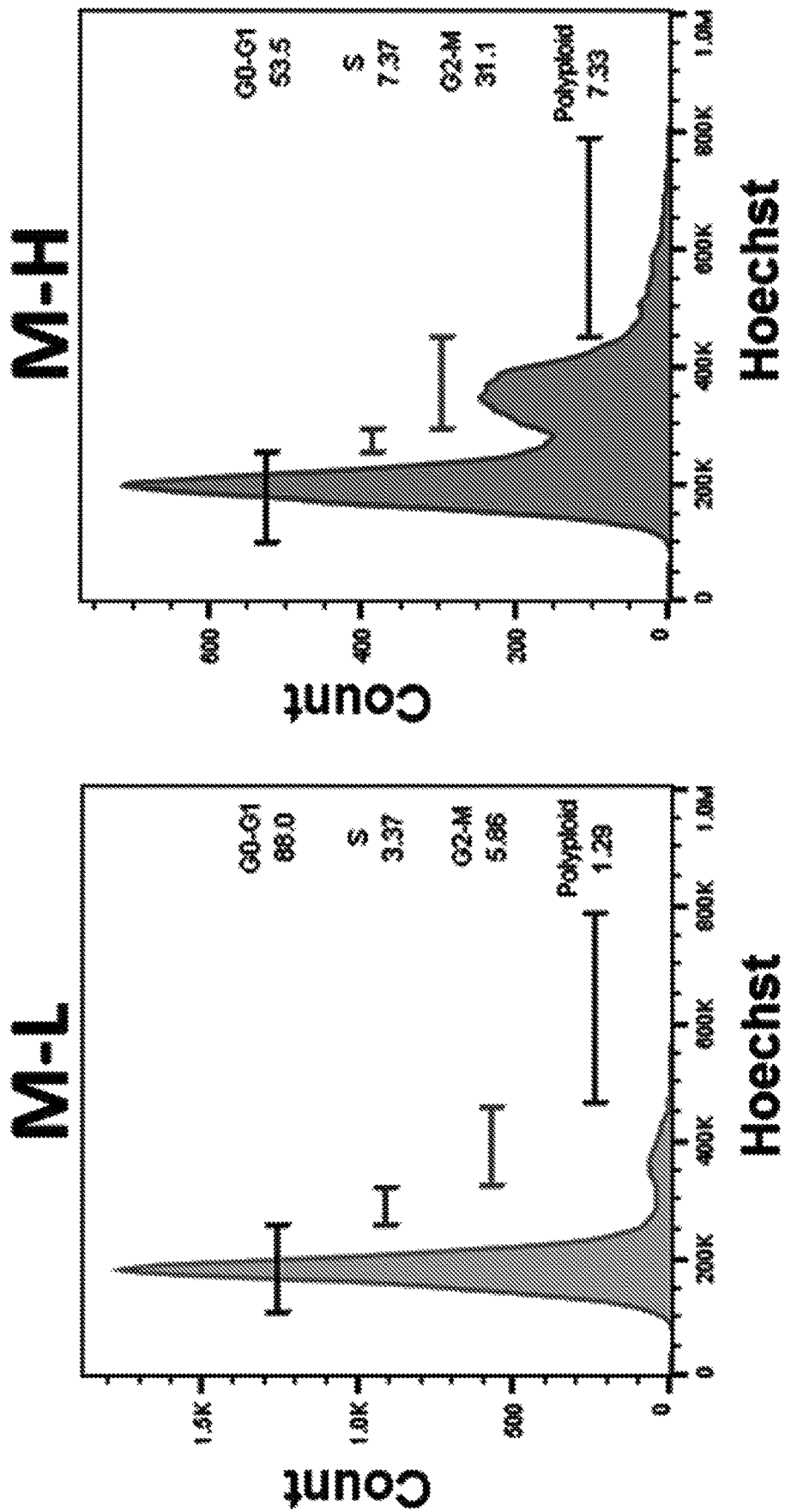
FIG. 3B shows Hoechst staining results for MCF7-monolyaer M-L and M-H cells.
Figure 3C:
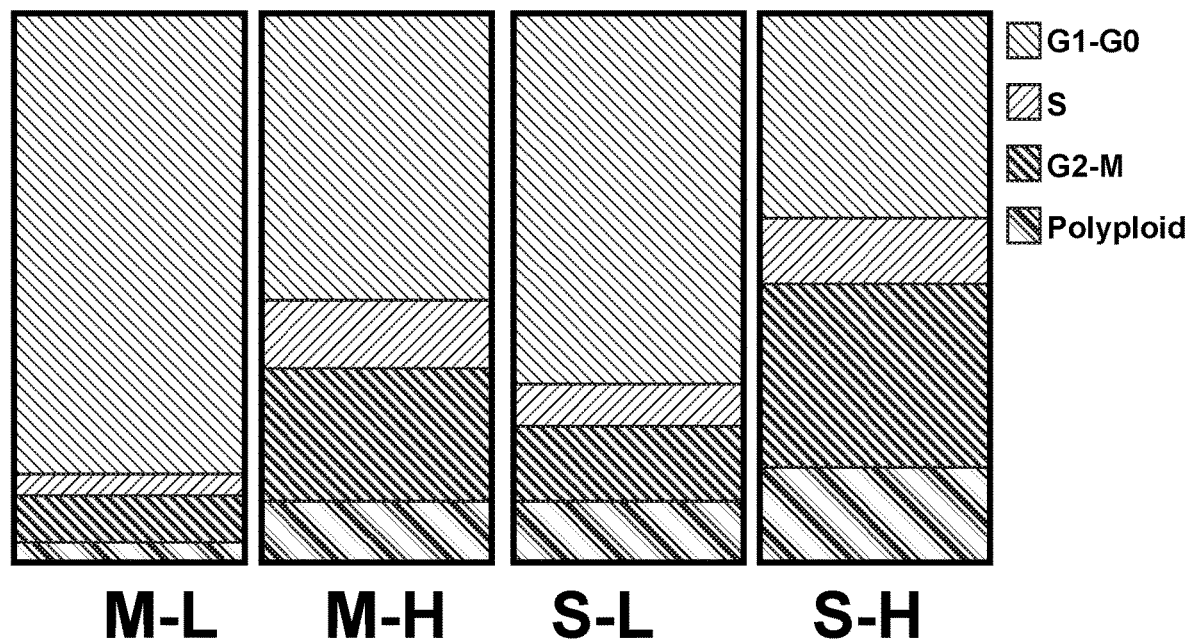
FIG. 3C is a cell cycle bar graph.

The next several paragraphs describe the characterization of the e-CSC phenotype, particularly with respect to proliferation, stemness, and bioenergetics. The e-CSC capacity for cell proliferation was assessed via cell cycle progression analysis. Representative cell cycle profiles (for different cell sub-populations of MCF7 are shown in FIG. 3A. The cell sub-populations in each phase are, from left to right, M-L, M-H, S-L, and S-H. FIG. 3B shows the results of Hoechst staining for MCF7-monolyaer M-L and M-H cells, and FIG. 3C shows a cell cycle bar graph.

The M-H cell and S-H cell sub-populations were exceedingly hyper-proliferative, with a reduction of cells in the G0/G1-phase and dramatic increases in both the S-phase and the G2/M-phase. Also, the number of polyploid cells (DNA>2N) was increased considerably in both the M-H and S-H populations. Overall, S-H cells were the most hyper-proliferative, with >40% of the cells in S-phase and/or G2/M, and <40% of the cells in the G0/G1-phase of the cell cycle. S-H cells also had the largest number of polyploid cells, reaching approximately 12-17%, probably due to mitotic catastrophe. In contrast, M-L cells had the highest number of cells in the G0/G1-phase of the cell cycle (~80%) and the lowest number of polyploid cells (~3-5%). Also, M-L cells showed the lowest number of cells in S-phase (~3-4%). These hyper-proliferative results with MCF7 cells (see Table 1, above) and MDA-MB-468 cells (see Table 2, above) are also consistent with a high-energy phenotype. Given this phenotype, the M-H and S-H cells were designated as "energetic" CSCs, also referred to as e-CSCs in this disclosure.

Figure 4A:
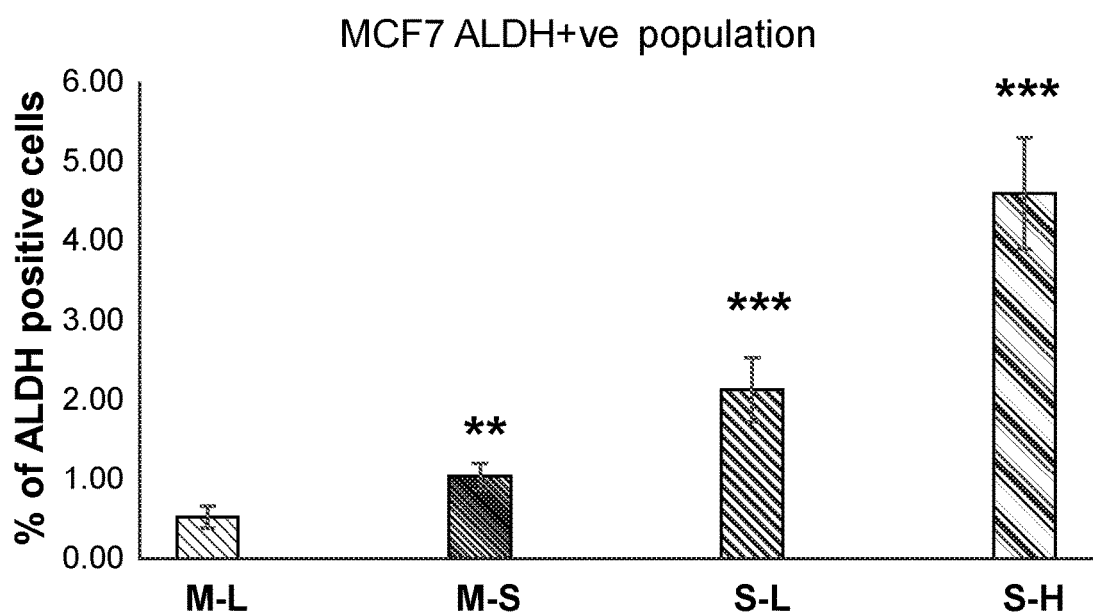
FIG. 4A shows ALDH activity for MCF7 cell sub-populations.
Figure 4B:
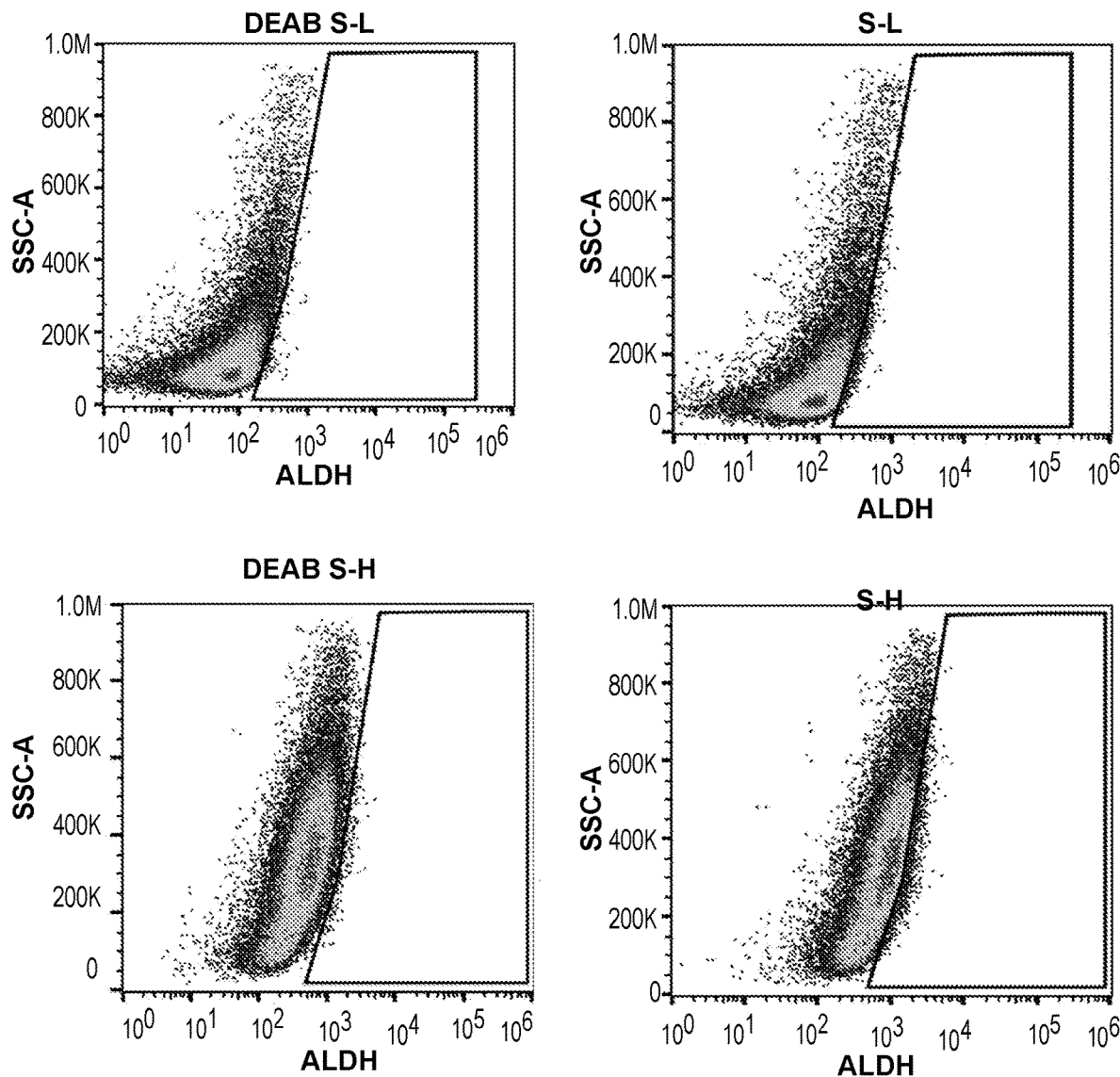
FIG. 4B shows the side scatter analysis for the sub-populations.

The stem cell characteristics of the M-H and S-H cells were then assessed. Specifically, ALDH was used as a marker of "stemness" activity to carefully monitor the progressive enrichment of CSCs. The results are shown in FIGS. 4A-4D, and show that e-CSCs have increased "stem-like" features. First, FIG. 4A shows the percentage of ALDH-positive cells for each of M-L, M-S, S-L, and S-H cell sub-populations. FIG. 4B shows the side scatter analysis results for the cell populations. FIGS. 4A and 4B show that relative to the cells with the least flavin (M-L), all the other cells showed the progressive enrichment of ALDH activity. With respect to ALDH activity, the MCF7 cells with the highest flavin-content also have the highest ALDH activity. More specifically, M-H cells (from 2D-monolayers) and S-H cells (from 3D-spheroids) showed the largest increases in ALDH activity, as seen by flow-cytometry analysis. Remarkably, M-H cells and S-H cells showed a 2-fold and a near 9-fold enrichment of ALDH-activity, respectively (see Table 3, above). The stem-like phenotype of M-H and S-H cells were further validated by using the mammosphere assay to measure anchorage-independent growth and by quantitatively measuring their mitochondrial mass, with MitoTracker Deep Red.

Figure 4C:
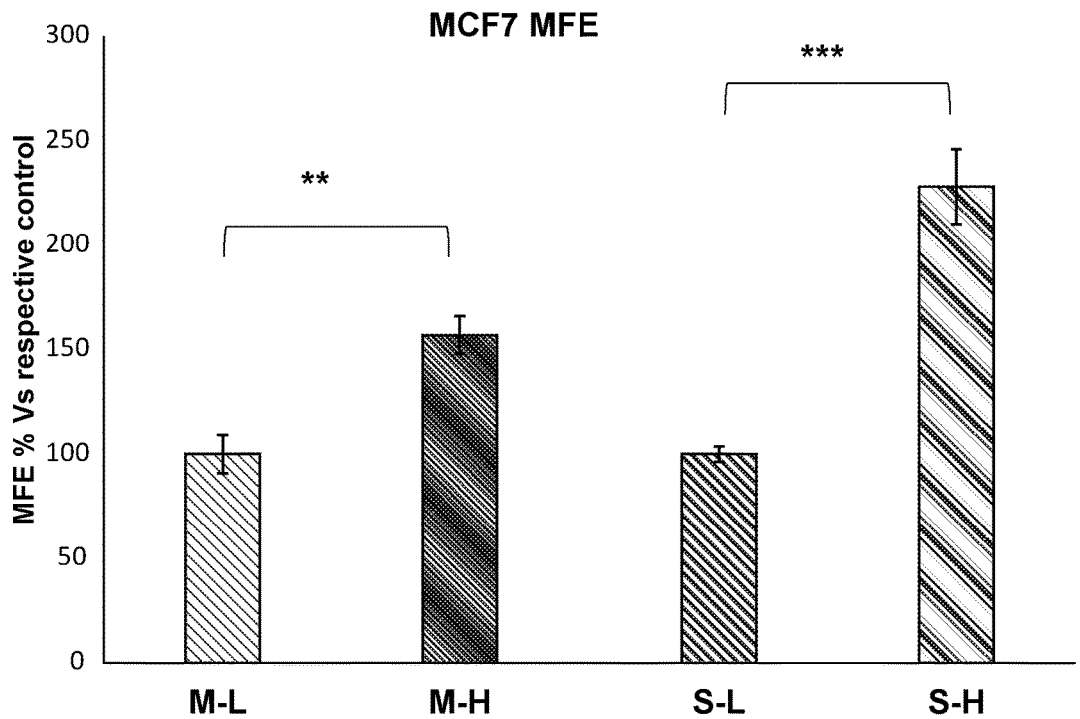
FIG. 4C shows mammosphere assay results.

The mammosphere assay allows for the quantitative measurement of anchorage-independent growth, which is a functional read-out for "stemness" activity. High mammosphere formation in MCF7 cells directly correlates with high-flavin content. For example, M-H cells (from 2D-monolayers) and S-H cells (from 3D-spheroids) show the highest rates of mammosphere formation, as compared to the M-L and S-L sub-populations. FIG. 4C shows the mammospheres assay results, and illustrates that relative to control cells, the M-H and S-H cell sub-populations formed mammospheres with greater efficiency, ~1.6-fold and 2.3-fold, respectively.

Figure 4D:
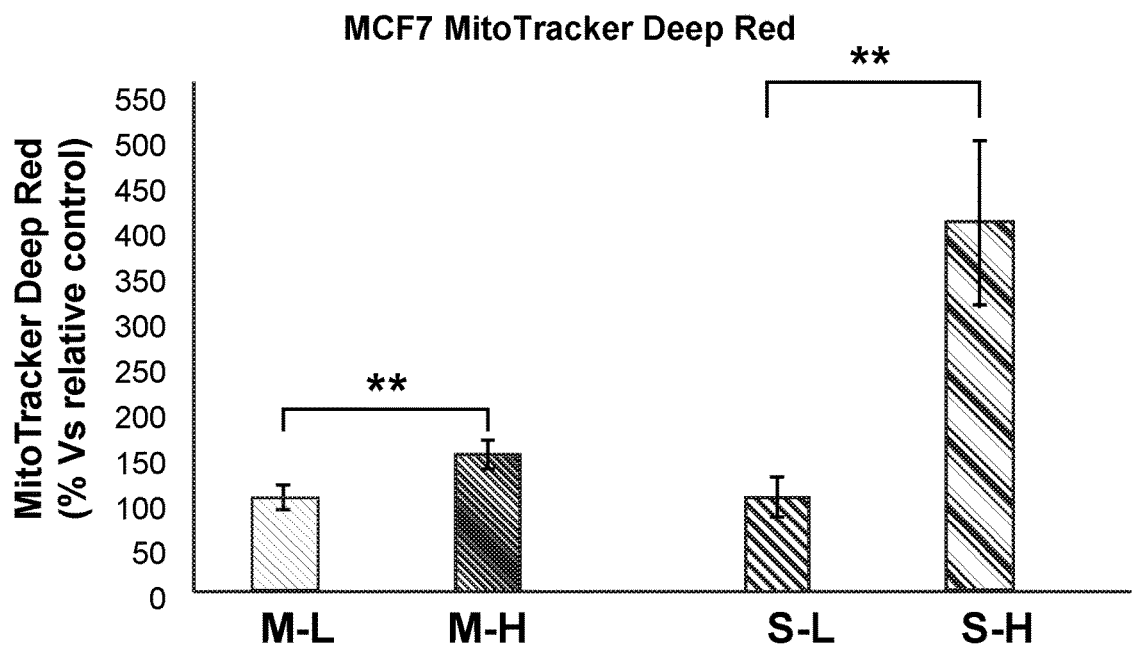
FIG. 4D shows MitoTracker Deep Red results.

Mitochondrial mass was assessed using MitoTracker Deep Red vital staining. The mitochondrial mass in MCF7 cells correlates with high-flavin content. In particular, S-H cells (from 3D-spheroids) show that largest increases in mitochondrial mass, as seen by flow-cytometry with MitoTracker Deep Red vital staining. FIG. 4D shows the MitoTracker Deep Red results, which is synonymous with their mitochondrial status. Relative to M-L cells, M-H cells showed a clear ~1.45-fold increase in mitochondrial mass. Relative to S-L cells, S-H cells demonstrated a remarkable ~4-fold increase in mitochondrial mass.

Therefore, e-CSCs derived from 3D-spheroids were i) the most hyper-proliferative, ii) showed the largest increases in stemness characteristics (ALDH activity and anchorage-independent growth), and iii) had the highest mitochondrial mass. These phenotypic changes are highly suggestive of metabolic re-programming, especially towards more oxidative mitochondrial metabolism.

Figure 5A:
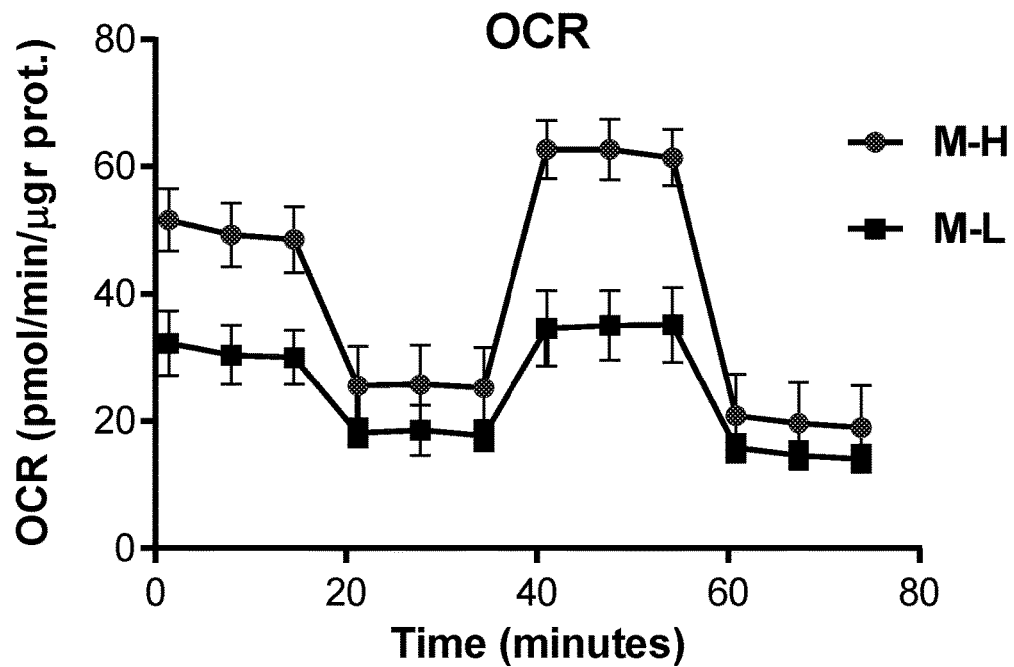
FIGS. 5A-5D show OCR data for MCF7 cell sub-populations.
Figure 5B:
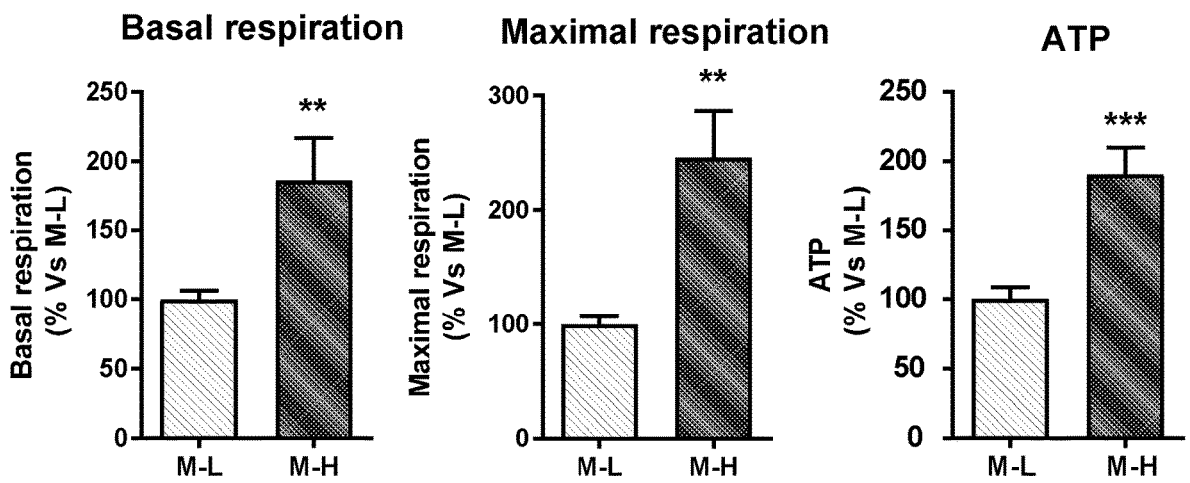
Figure 5C:
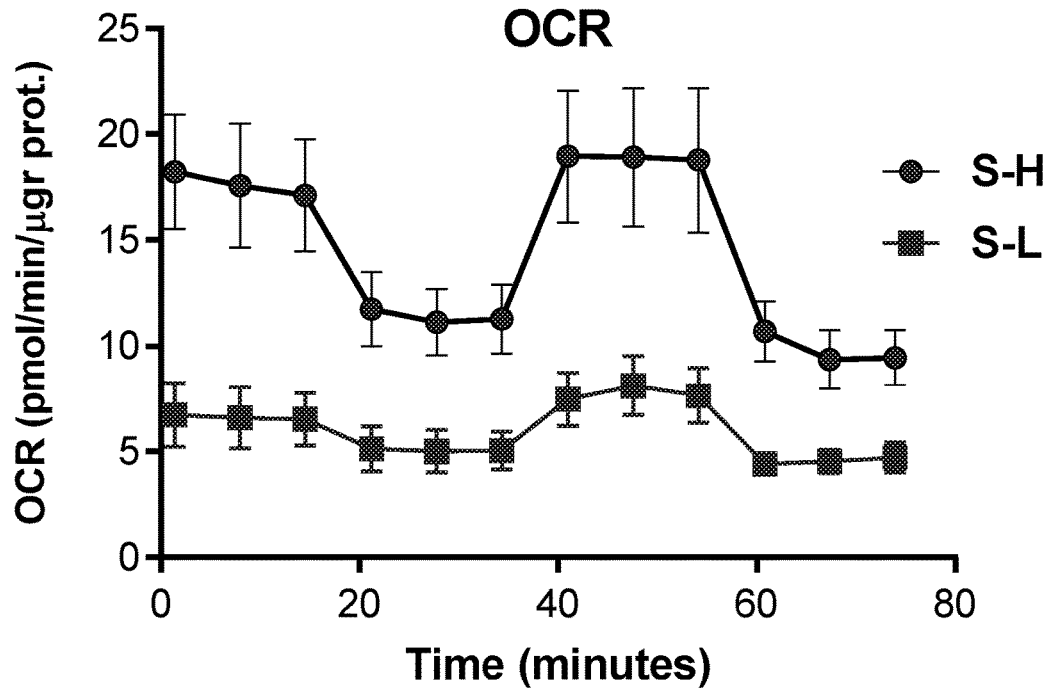
Figure 5D:
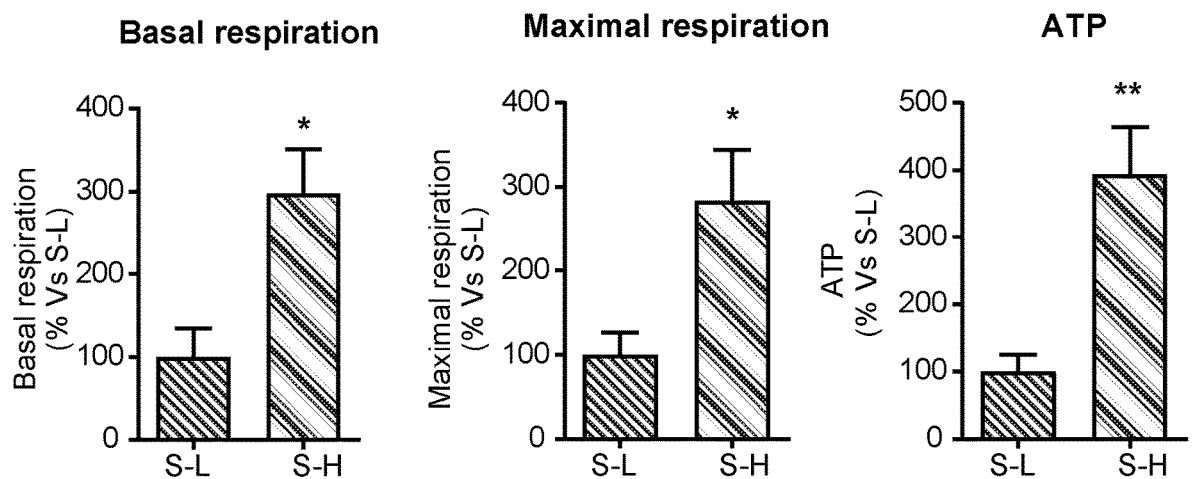

To characterize the bioenergetic phenotype of e-CSCs, the cell populations were subjected to metabolic flux analysis, using the Seahorse XFe96. Mitochondrial oxygen consumption rate (OCR) and extracellular acidification rate (ECAR) were the measured properties. OCR results include basal respiration, maximal respiration, and ATP. ECAR results include glycolysis, glycolytic reserve, and glycolytic reserve capacity. FIGS. 5A and 5B show OCR results for M-H and M-L cells, and FIGS. 5C and 5D show the OCR results for S-H and S-L cells. High OCR in MCF7 cells directly correlates with high-flavin content. For example, M-H cells (from 2D-monolayers) and S-H cells (from 3D-spheroids) have the highest levels of OCR, as compared to the M-L and S-L sub-populations.

Figure 6A:
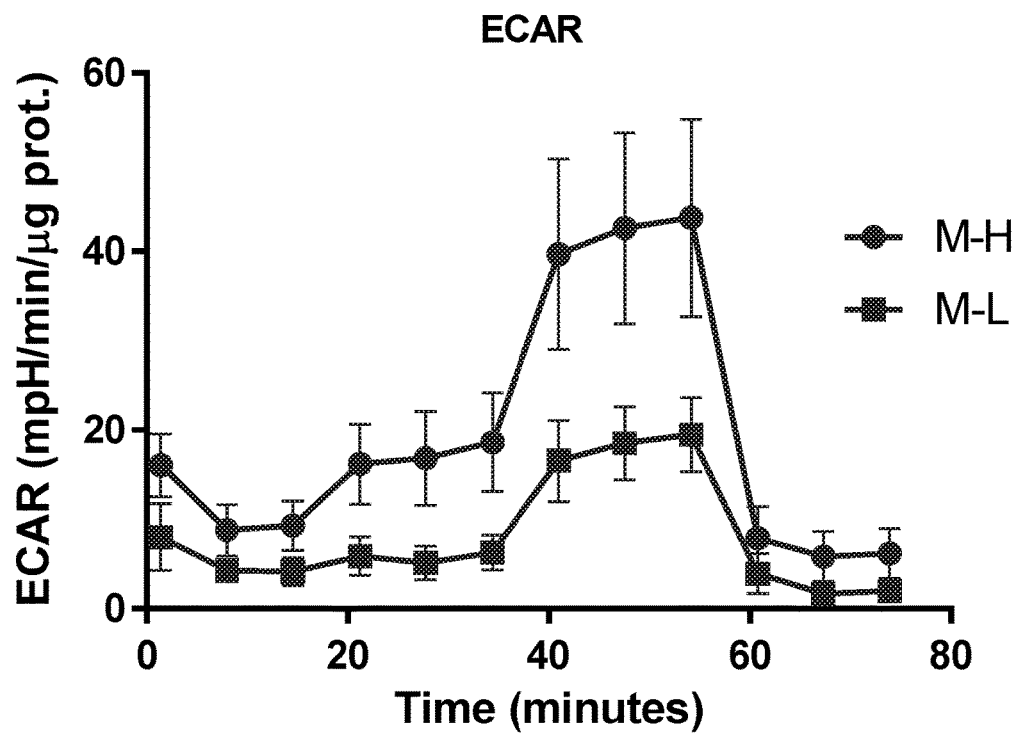
FIGS. 6A-6D show ECAR data for same MCF7 cell sub-populations.
Figure 6B:
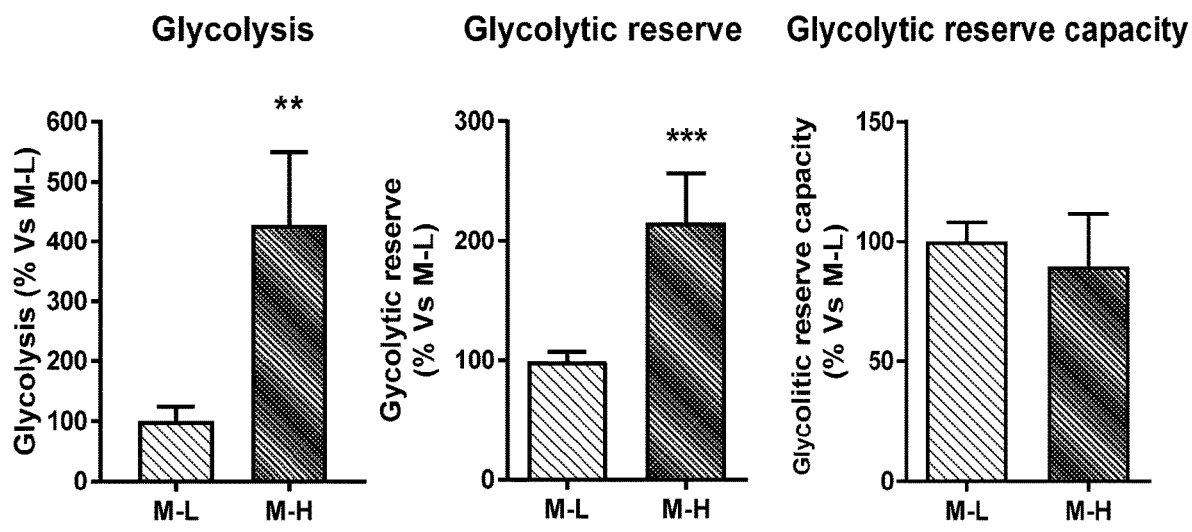
Figure 6C:
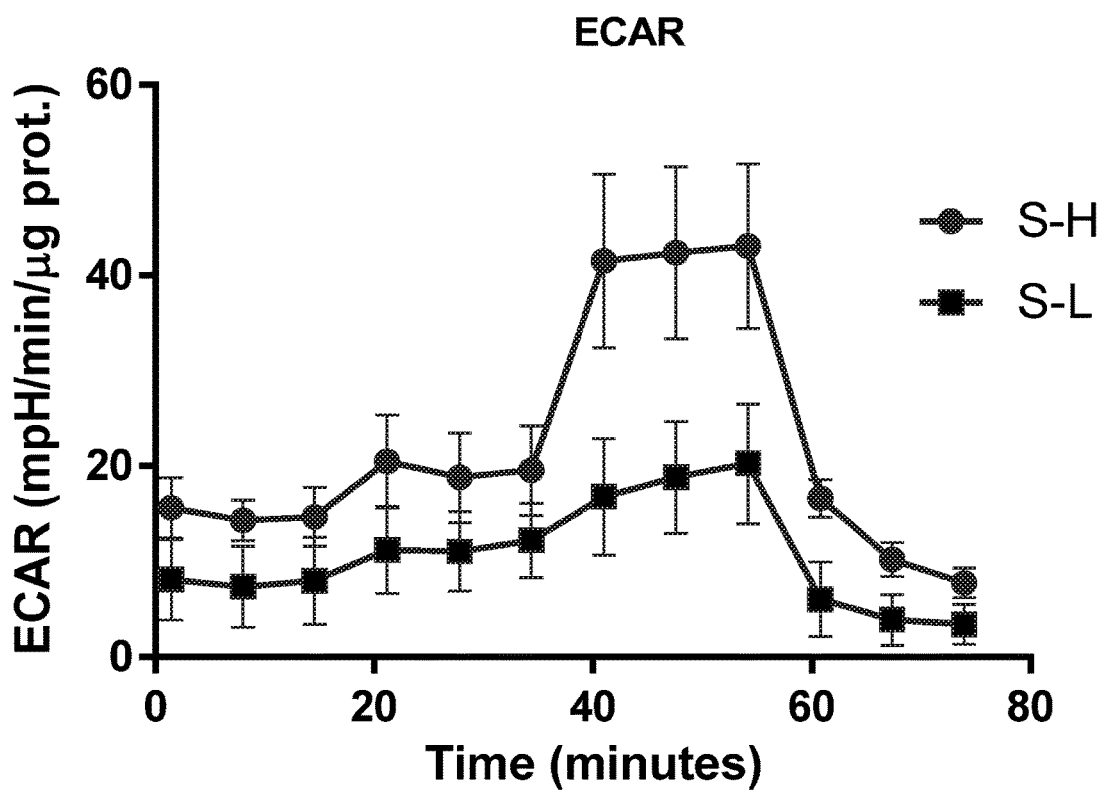
Figure 6D:
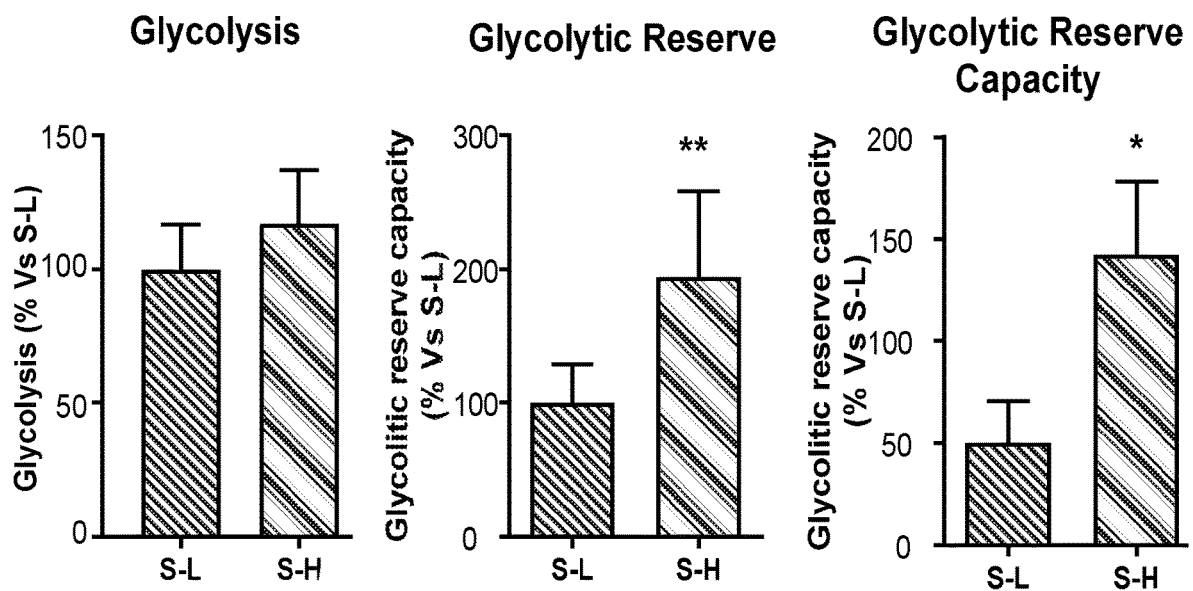

The data also demonstrates that e-CSCs have elevated levels of aerobic glycolysis. The extracellular acidification rate (ECAR) was measured, using the Seahorse XFe96 metabolic-flux analyzer. FIGS. 6A and 6B show ECAR results for M-H and M-L cells, and FIGS. 6C and 6D show the ECAR results for S-H and S-L cells. Note that high ECAR in MCF7 cells directly correlates with high-flavin content. For example, M-H cells (from 2D-monolayers) and S-H cells (from 3D-spheroids) have the highest levels of ECAR, as compared to the M-L and S-L sub-populations. It can be seen from FIGS. 5A and 5B that M-H cells are highly oxidative, with an almost 2-fold increase in OCR, mitochondrial respiration and ATP-production. However, the largest changes can be seen in FIG. 6A, in glycolytic phenotype, with about a 4-fold increase in glycolytic activity for M-H cells. As such, M-H cells are highly glycolytic, and have an enhanced mitochondrial metabolism.

In contrast, S-H cells demonstrated the highest increases in OCR, with a near 3-fold increase in basal respiration and a 4-fold increase in ATP production as seen in FIG. 5C.

However, FIG. 6D shows that the S-H cells' basal glycolytic rate remained unchanged, suggestive of a greater dependence on mitochondrial OXPHOS metabolism. As a consequence, S-H cells are expected to be more sensitive to mitochondrial OXPHOS inhibitors, highlighting a weak point in e-CSCs derived from 3D-spheroids.

The e-CSC phenotype allows for developing new therapeutics that target the metabolic nature of the sub-population. For example, it should be appreciated that e-CSCs may be targeted using OXPHOS inhibitors and/or CDK4/6 inhibitors. They may also be targeted with mitochondrial inhibitors. The following paragraphs describe examples of such therapeutic agents for targeting and eradicating e-CSCs, as an anti-cancer therapy. It should be appreciated that in some embodiments, these therapeutics may be used in conjunction with other anti-cancer therapies.

The first example therapeutic is DPI (Diphenyleneiodonium chloride), an OXPHOS inhibitor that specifically targets flavin-containing enzymes, especially those associated with FMN/FAD and mitochondrial complex I and II. DPI inhibits 3D-spheroid formation in MCF7 cells, and DPI selectively inhibits mitochondrial function without any toxic side effects. In prior studies, DPI did not induce changes in cell viability or apoptosis, but instead shifted the cells towards a more glycolytic phenotype.

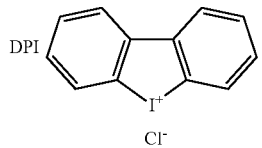 [SMILES: "DPI" ; c1ccc2c(c1)[I+]c1ccccc1-2 ; [Cl-]]

Figure 7A:
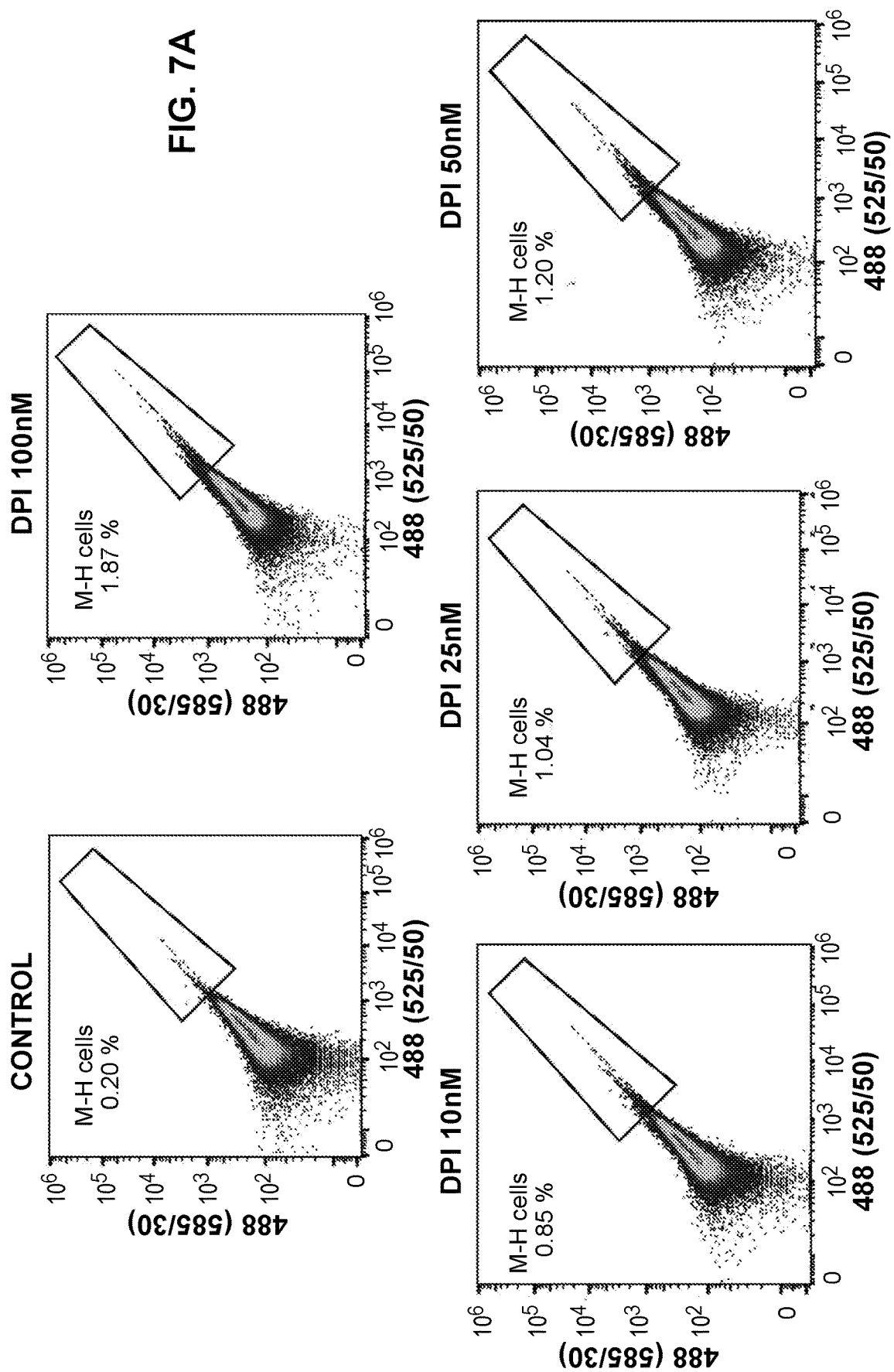
FIGS. 7A-C show the results of DPI treatment at various concentrations on M-H cells from MCF7 monolayers.
Figure 7B:
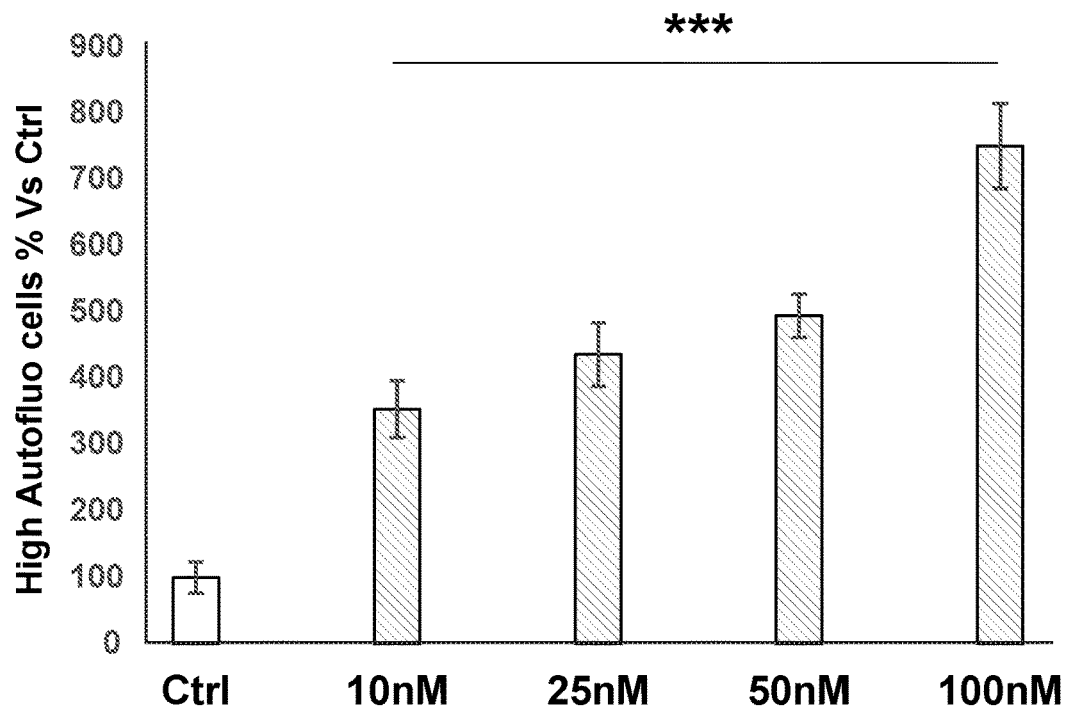
Figure 7C:
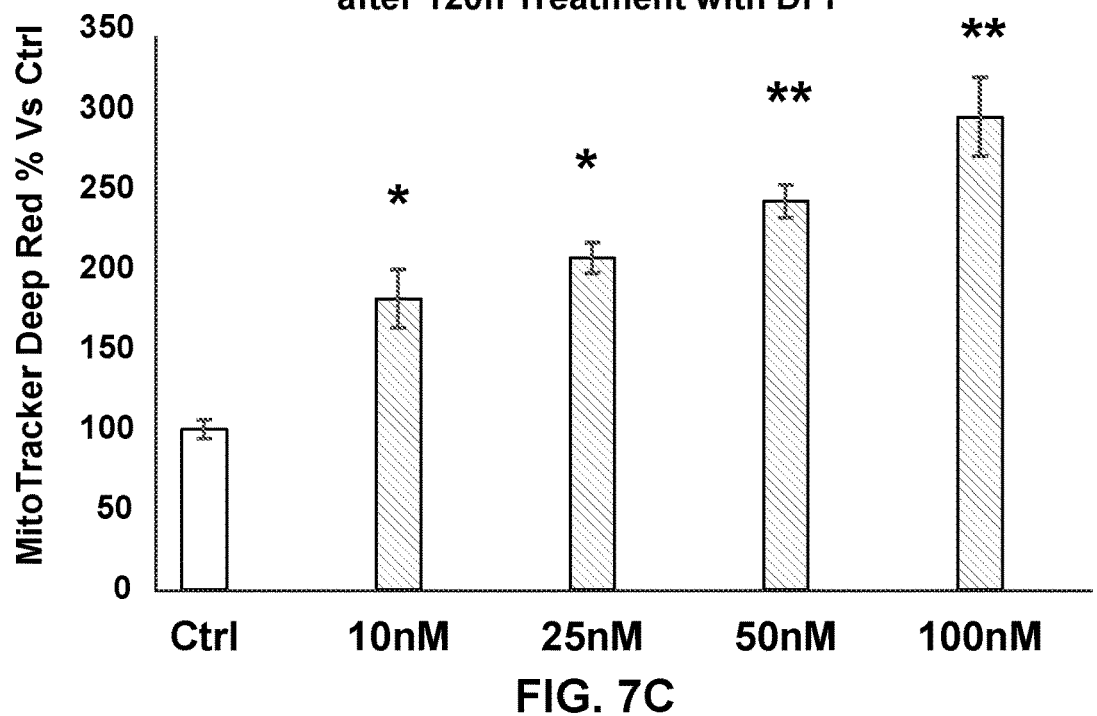

FIGS. 7A-C show the results of DPI treatment at various concentrations on M-H cells from MCF7 monolayers. The data represents 100,000 cells after 120 hours of DPI treatment. First, FIG. 7A shows a series of flow cytometry tracings, each at a different concentration of DPI, and shows an increase in M-H cells as DPI concentration increases. FIG. 7B is a bar graph showing the change in M-H cells after treatment, also confirming the increase in M-H cells. The bar graph shows that the percentage of M-H cells are increased after treatment with DPI, a mitochondrial OXPHOS inhibitor, over a 5-day period, in a concentration dependent manner. FIG. 7C shows MitoTracker Deep Red results after 130 hours of DPI treatment, which indicates an increase in mitochondrial mass. The bar graph shows that the mitochondrial mass (MitoTracker) is increased after treatment with DPI, over the same time-frame. The increase in M-H cell propagation and mitochondrial mass with increasing concentration of DPI treatment is consistent with the high basal glycolytic rate for M-H cells, discussed above.

Figure 8A:
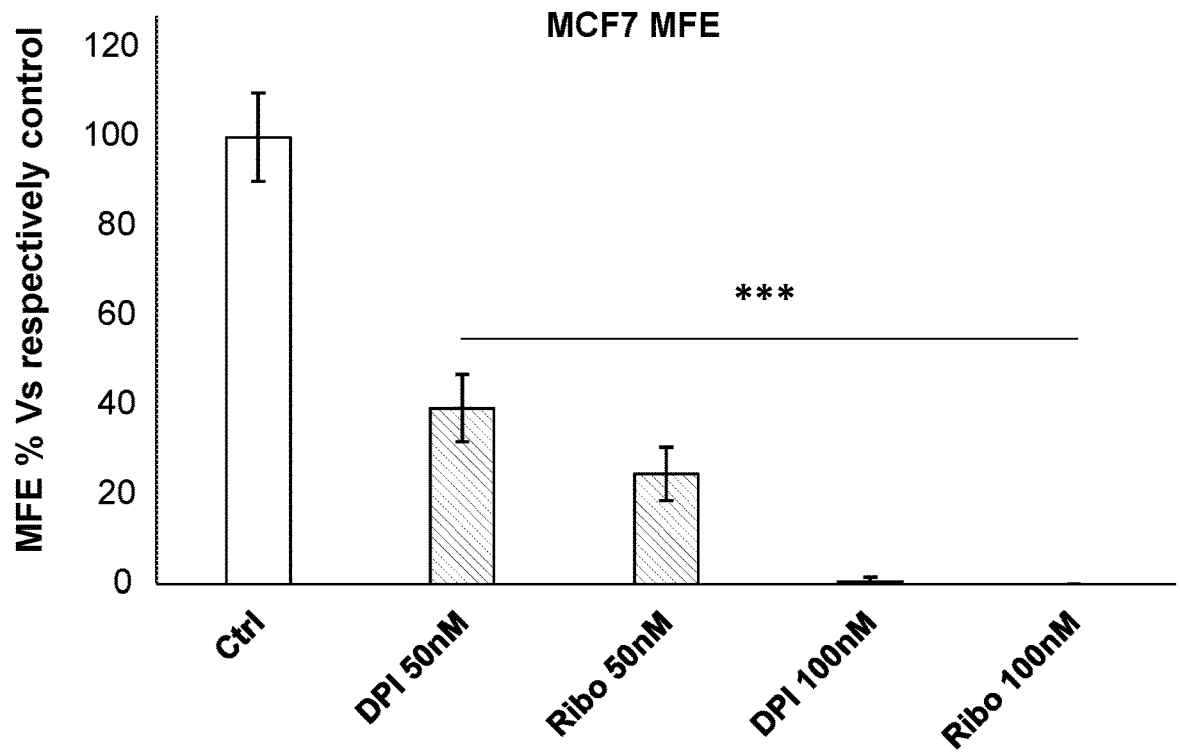
FIGS. 8A-8C show data demonstrating that e-CSCs (3D) are susceptible to targeting with DPI or Ribociclib.
Figure 8B:
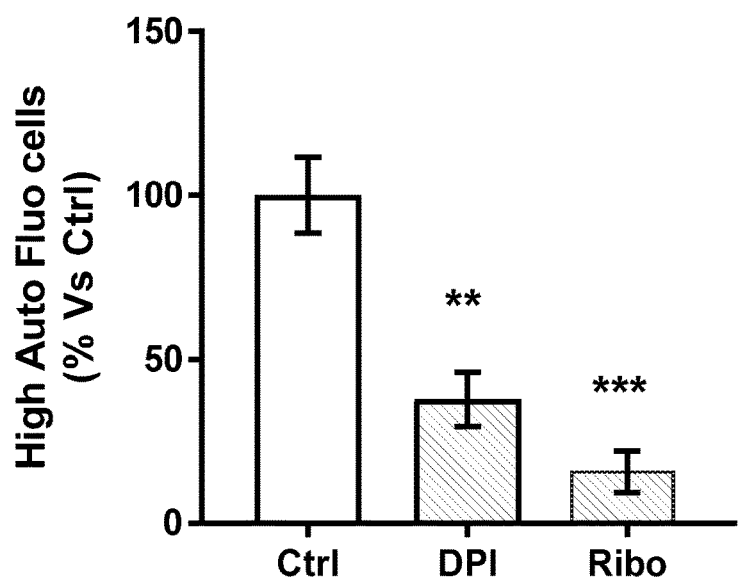
Figure 8C:
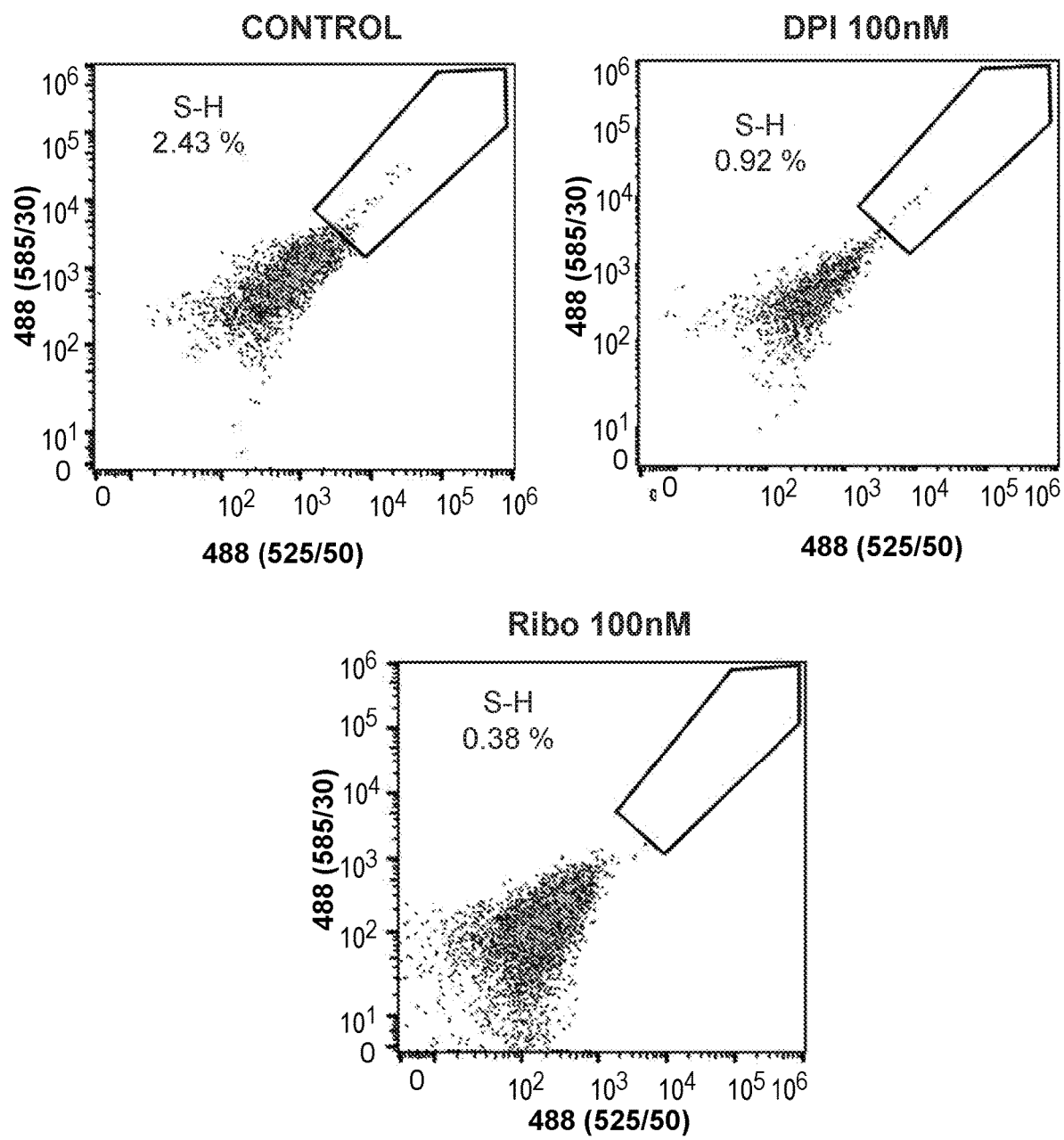

The S-H cells, on the other hand, are sensitive to DPI, as can be seen in FIGS. 8A-C. FIG. 8A is a bar graph showing mammosphere formation in MCF7 cells at various concentrations of DPI, and including Ribociclib at 100 nM. FIG. 8B shows the change in S-H cells decreasing from control to 100 nM of DPI and Ribociclib. The bar graph shows that mammosphere formation in MCF7 cells is inhibited in response to DPI or Ribociclib treatment, in a dose-dependent manner (0, 50 and 100 nM). FIG. 8C shows a series of flow cytometry tracings for S-H cells after treatment with 100 nM DPI (showing a reduction in S-H cells). As can be seen, DPI has opposite effects on M-H and S-H cells, namely, DPI selectively targets the S-H sub-population of e-CSCs. This demonstrates that e-CSCs are metabolically-wired differently, depending on whether the cell is proliferating in a 2D-monolayer or a 3D-spheroid micro-environment. Most importantly, e-CSCs derived from 3D-spheroids are highly oxidative and can be effectively targeted with an OXPHOS inhibitor. Non-limiting examples of other OXPHOS inhibitors that may be used in the present approach include atovaquone, irinotecan, sorafenib, niclosamide, and berberine chloride.

Complementary experiments were carried out with Ribociclib, a clinically-approved CDK4/6 inhibitor. Ribociclib is normally used to treat female breast cancer patients, in combination with letrozole (an aromatase inhibitor). Ribociclib was first developed by Astex Pharmaceuticals (Cambridge, UK) and Novartis. In 2017, Ribociclib was approved by the FDA and the European Medicines Agency, for the treatment of HR-positive, HER2-negative advanced or metastatic breast cancers. The drug's most common side-effects are: neutropenia, anemia and GI-distress. The data for treatment with Ribociclib in FIGS. 8A-C illustrate that treatment with Ribociclib effectively inhibits the propagation of S-H cells. Therefore, anchorage-independent proliferation by S-H cells is critically-dependent on CDK4/6 function, as well as mitochondrial metabolism. The Ribociclib structure is shown below:

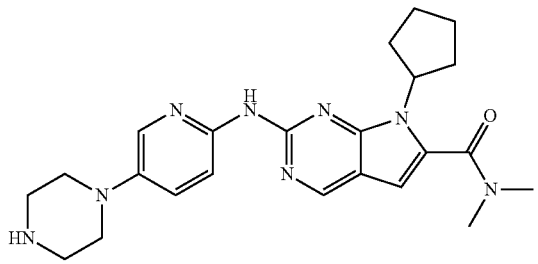 [SMILES: CN(C)C(=O)c1cc2cnc(Nc3ccc(N4CCNCC4)cn3)nc2n1C1CCCC1]

It should be appreciated that Ribociclib is one example of a CDK4/6 inhibitor, and that other CDK4/6 inhibitors may be used under the present approach. Other non-limiting examples of CDK4/6 inhibitors include, but are not limited to, abemaciclib (Verzenio) and palbociclib (Ibrance).

Mitochondrial inhibitors may be used to eradicate e-CSCs. In the present approach, the mitochondrial inhibitors may be or include one or more of: a mitoriboscin, the combination of an oxidative metabolism inhibitor and a glycolytic metabolism inhibitor, a repurposcin, an antimitoscin, a mitoketoscin, a mitoflavoscin, a mitoflavin, a TPP-derivative, an MDIVI-1 derivative, chloramphenicol, puromycin and other inhibitors of protein synthesis (including, e.g., aminoglycosides and rapamycin analogues), anti-parasitic drugs (such as, e.g., pyrvinium pamoate, and niclosamide), chloroquine, stiripentol, caffeic acid phenyl ester (CAPE), Vitamin C, 2-Deoxy-Glucose (2-DG), MCT1 inhibitors (AZD3965 and AR-C155858), D-Glucosamine, quercetin, and carvedilol. It should be appreciated that a therapeutic compound may fall under more than one category. The following paragraphs describe certain categories of mitochondrial biogenesis inhibitor therapeutics. For brevity, the related co-pending applications are incorporated by reference as if fully set forth herein.

A first category of therapeutics are mitoriboscins, as described in International Application No. PCT/US2018/022403, filed Mar. 14, 2018, and incorporated by reference in its entirety. The incorporated reference includes data for select mitoriboscin compounds. Generally, mitoriboscins are mitochondrial inhibitor compounds that have anti-cancer and often antimicrobial activity, chemotherapy-sensitizing, radiosensitizing, and photosensitizing effects, as well as anti-aging effects. These compounds bind to either the large sub-unit or the small sub-unit of the mitoribosome (or in some instances, both) and inhibit mitochondrial biogenesis. Examples of mitoriboscin groups, along with generic chemical structures and specific compounds, are described in the incorporated application, and include mitoribocyclines, mitoribomycins, mitoribosporins, and mitoribofloxins.

A second category of mitochondrial biogenesis inhibitor therapeutics include combination therapies involving oxidative metabolism inhibitors and glycolytic metabolism inhibitors. e-CSCs in a mass may be reduced targeted and eradicated by administering a pharmaceutically effective amount of at least one oxidative metabolism inhibitor, and at least one glycolytic metabolism inhibitor. Inhibitors of oxidative metabolism may include members of the tetracycline family and the erythromycin family. Members of the tetracycline family include tetracycline, doxycycline, tigecycline, minocycline, chlortetracycline, oxytetracycline, demeclocycline, lymecycline, meclocycline, methacycline, rolitetracycline, chlortetracycline, omadacycline, and sarecycline. Members of the erythromycin family include erythromycin, azithromycin, and clarithromycin. Glycolytic metabolism inhibitors may be selected from inhibitors of glycolysis, inhibitors of OXPHOS, and inhibitors of autophagy. Examples of glycolysis inhibitors include 2-deoxy-glucose, ascorbic acid, and stiripentol. OXPHOS inhibitors include atoravaquone, irinotecan, sorafenib, niclosamide, and berberine chloride. Autophagy inhibitors include chloroquine. Data and further examples are described in International Application No. PCT/US2018/028587, filed Apr. 20, 2018, which is incorporated by reference in its entirety.

Some embodiments of combination therapies may take the form of a triple combination. For example, in some embodiments of the present approach, a first antibiotic inhibiting the large mitochondrial ribosome (such as, for example, members of the erythromycin family), and a second antibiotic inhibiting the small mitochondrial ribosome (such as, for example, members of the tetracycline family), may be administered with a pro-oxidant or an agent inducing mitochondrial oxidative stress (e.g., low concentrations of Vitamin C, radiation therapy, among other examples). As a specific example, FDA-approved antibiotics doxycycline and azithromycin may be used in connection with one or more common dietary supplements (e.g., Vitamin C). In an example embodiment, treatment with a combination of doxycycline (at 1 µM), azithromycin (at 1 µM), and Vitamin C (at 250 µM) may be used as the mitochondrial biogenesis inhibitor. The pro-oxidant may be, in some embodiments, a therapeutic agent having a pro-oxidant effect. For example, the pro-oxidant may be a therapeutic agent at a concentration that causes the therapeutic agent to act as a reducing agent. U.S. Provisional Patent Application 62/780,488, filed Dec. 17, 2018 and incorporated by reference in its entirety, provides further description of triple combination therapies.

Antimitoscins are a third category of mitochondrial biogenesis inhibitors, described more fully in International Patent Application PCT/US2018/033466, filed May 18, 2018 and incorporated by reference in its entirety. Existing antibiotics having intrinsic anti-mitochondrial properties can be chemically modified to target the mitochondria and inhibit mitochondrial biogenesis. The term "antimitoscin" broadly refers to an antibiotic having intrinsic anti-mitochondrial properties that is chemically modified to target the antibiotic to mitochondria. Previously, intrinsic anti-mitochondrial activity in antibiotics was considered to be an unwanted side-effect. Indeed, some potential antibiotics have been excluded from trials due to excessive anti-mitochondrial properties, and researchers have viewed anti-mitochondrial activity as a potential drawback. However, under the present approach, an antibiotic's intrinsic anti-mitochondrial activity can become the basis for an entirely new therapeutic. The antimitoscin may be an antibiotic having intrinsic anti-mitochondrial properties chemically modified with a mitochondrial targeting signal (e.g., a chemical moiety). Chemical modification may be, for example, through covalent or non-covalent bonds. In some embodiments, the antibiotic is one of a member of the tetracycline family, the erthyromycin family, chloramphenicol, pyrvinium pamoate, atovaquone, and bedaquiline. The mitochondria-targeting signal may be at least one compound or moiety selected from the group comprising a membrane targeting signal and a mitochondrial ribosome-targeting signal. Examples of membrane targeting signals include short-chain (e.g., fewer than 6 carbon atoms in the chain) fatty acids and medium-chain (e.g., 6-12 carbon atoms in the chain) fatty acids, palmitic acid, stearic acid, myristic acid, and oleic acid. Examples of mitochondrial ribosome-targeting signals include tri-phenyl-phosphonium (TPP) and guanidinium-based moieties. TPP and guanidinium are non-toxic chemical moieties that functionally behave as a mitochondrial targeting signal (MTS) in living cells. Either may be bonded to an antibiotic, often through the use of a carbon spacer-arm or linking chain.

A fourth category of mitochondrial biogenesis inhibitors are mitoketoscins, non-carcinogenic compounds that bind to at least one of ACAT1/2 and OXCT1/2 and inhibit mitochondrial ATP production. These compounds are described more fully in International Application PCT/US2018/039354, filed Jun. 25, 2018, and incorporated by reference in its entirety. Generally, a mitoketoscin targets the mitochondrial enzymes responsible for ketone re-utilization and that have anti-cancer and antibiotic properties. These compounds bind to either or both active catalytic sites of OXCT1/2 and ACAT1/2 to inhibit mitochondrial function.

Mitoflavoscins and mitoflavins are a fifth category of mitochondrial biogenesis inhibitors that may be used under the present approach. These compounds are described more fully in International Patent Application PCT/US2018/057093, filed Oct. 23, 2018 and incorporated by reference in its entirety. Mitoflavoscins are compounds that bind to flavin-containing enzymes and inhibit mitochondrial ATP production. Diphenyleneiodonium chloride (DPI) is an example of a mitoflavoscin. It should be appreciated that a mitoflavoscin may be modified with a mitochondrial targeting signal, such as discussed above with respect to antimitoscins. Mitoflavins, derivatives of riboflavin that inhibit mitochondrial function, may also be chemically modified with a mitochondrial targeting signal. For example, roseoflavin [8-Demethyl-8-(dimethylamino)-riboflavin or 8-Dimethylaminoriboflavin] is a naturally occurring anti-bacterial compound that is a derivative of riboflavin, which can be chemically modified to optimize its potential for targeting CSCs and inhibiting mitochondrial biogenesis. Lumichrome (7,8-Dimethylalloxazine) is a fluorescent photoproduct of riboflavin degradation, which also can be chemically modified to optimize its potential for targeting CSCs. Other common derivatives of riboflavin include: Alloxazine, Lumiflavine, 1,5-dihydroriboflavin and 1,5-dihydroflavin. Each of these riboflavin derivatives may be chemically modified with a mitochondrial targeting signal to form a mitoflavin, and may be used as a mitochondrial biogenesis inhibitor according to the present approach.

A sixth category of mitochondrial biogenesis inhibitors is TPP-derivative compounds that show not only a strong preference for uptake in cancer cells (bulk cancer cells, cancer stem cells, and energetic cancer stem cells), but also disrupt mitochondrial biogenesis in these cells. These TPP-derivative compounds are described more fully in International Patent Application PCT/US2018/062174, filed Nov. 21, 2018 and incorporated by reference in its entirety. As used with respect to TPP-derivatives, a derivative as known in the art is a compound that can be synthesized from a parent compound by replacing an atom with another atom or group of atoms. For example, a derivative of TPP is 2-butene-1,4-bis-TPP, which includes two phosphonium groups joined by butene. A derivative of 2-butene-1,4-bis-TPP, then, could include replacement of one or more phenyl groups with another compound, such as a halogen or an organic compound. For the sake of brevity, this disclosure does not identify all of the potential derivatives, as the description should be adequate for a person of ordinary skill in the art. Other examples of TPP-derivative compounds that may be used as mitochondrial biogenesis inhibitors according to the present approach include 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. Of course, it should be appreciated that the foregoing list is not an exhaustive list of TPP-derivatives.

Repurposcins are a seventh category of mitochondrial biogenesis inhibitors that may be used in embodiments of the present approach. International Patent Application PCT/US2018/062956, filed Nov. 29, 2018 and incorporated by reference in its entirety, describes these compounds more fully. Generally, "repurposcins" are compounds having intrinsic anti-mitochondrial properties that are chemically modified to target the compounds to mitochondria. Such compounds may include, for example, FDA-approved pharmaceuticals, nutraceuticals, and supplements, among others. Compounds having intrinsic anti-mitochondrial properties may be chemically modified with one or more mitochondrial targeting signals as described above. Examples of compounds having intrinsic anti-mitochondrial properties include berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, and fenofibrate. In some embodiments, the compound may be one or more of neomycin, puromycin, rapamycin (and its derivatives, such as everolimus), G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, a member of the tetracycline family, a member the erthyromycin family, clindamycin, metronidazole, linezolid, mupirocin, vancomycin, clindamycin, cephalosporin, ciprofolxacin, streptomycin, amoxicillin, and azelaic acid. It should be noted that a repurposcin formed from an antibiotic may also be referred to as an antimitoscin.

An eighth category of mitochondrial biogenesis inhibitors that may be used in the present approach is MDIVI-1 derivatives, as described in International Patent Application PCT/US2018/066247, filed Dec. 18, 2018 and incorporated by reference in its entirety. Mitochondrial division inhibitor-1 (mDIVI-1) is a small molecule that selectively and reversibly inhibits DRP1. MDIVI-1 has been shown to target DRP1 by binding and suppressing both the DRP1 self-assembly into ring-like structures around the mitochondria and its capacity to catalyze GTP hydrolysis. The present approach may take the form of a mitochondrial fission inhibitor 1 (mDIVI-1) derivative having the general formula:

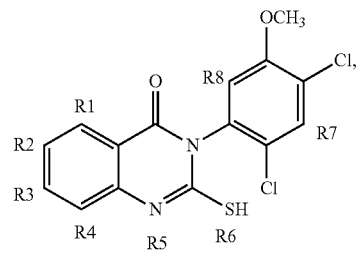

or a pharmaceutically acceptable salt thereof, wherein each of R1 through R8 may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and a mitochondrial targeting signal. In some embodiments, at least one R-group is a mitochondrial targeting signal, such as palmitic acid, stearic acid, myristic acid, and oleic acid, a short-chain fatty acid, a medium-chain fatty acid, tri-phenyl-phosphonium (TPP), a TPP-derivative, a lipophilic cation, and 10-N-nonyl acridine orange. In some embodiments, at least one R-group is a mitochondrial targeting signal, such as one of 2-butene-1, 4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. It should be appreciated that MDIVI-1 derivatives may be used as mitochondrial inhibitors under the present approach, with one or more of the chemical modifications described in this paragraph.

Figure 9A:
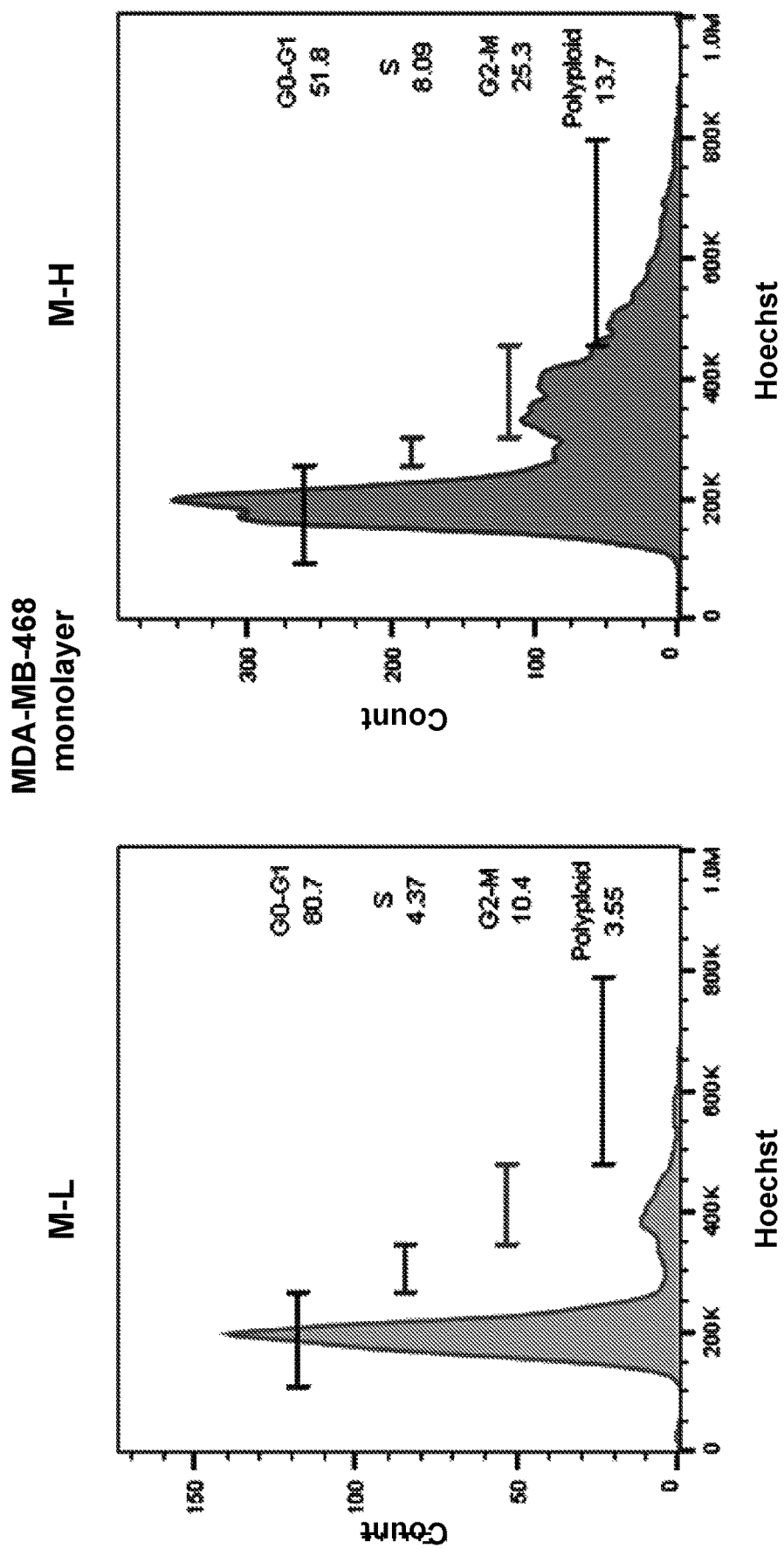
FIGS. 9A-9D show cell cycle progression data for MDA-MB-468 e-CSCs.
Figure 9B:
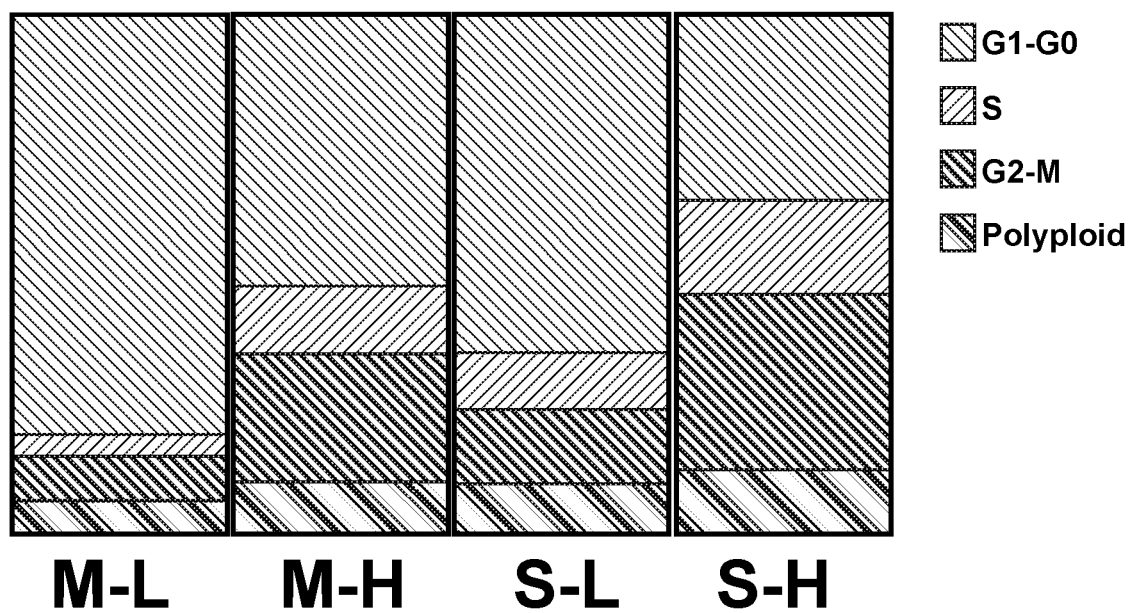
Figure 9C:
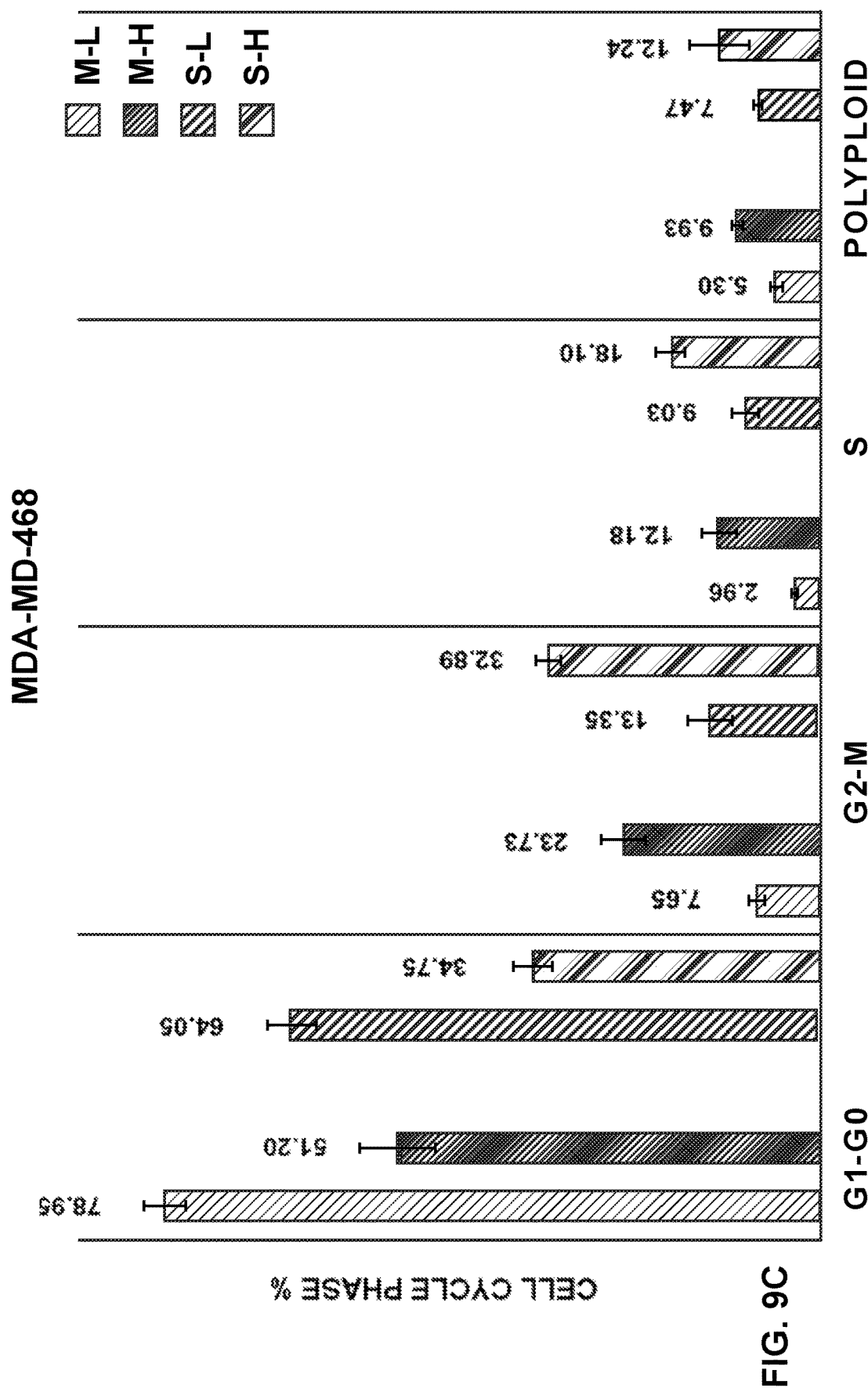
Figure 9D:
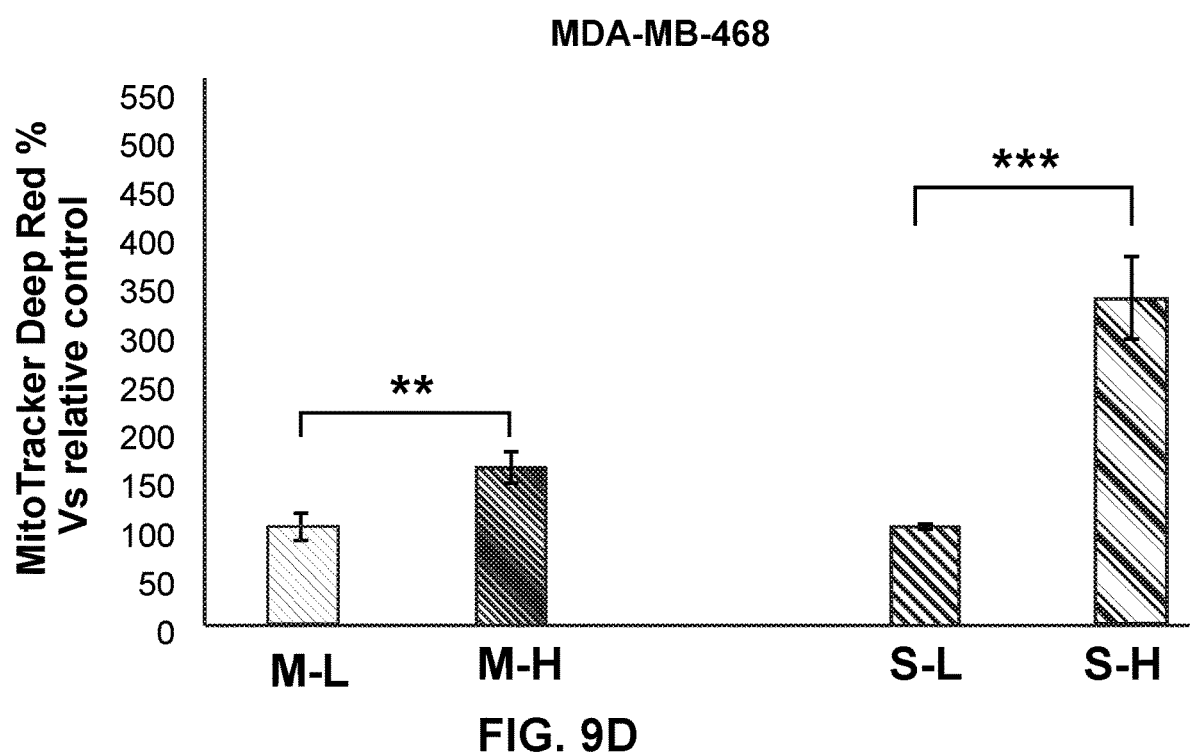
Figure 10A:
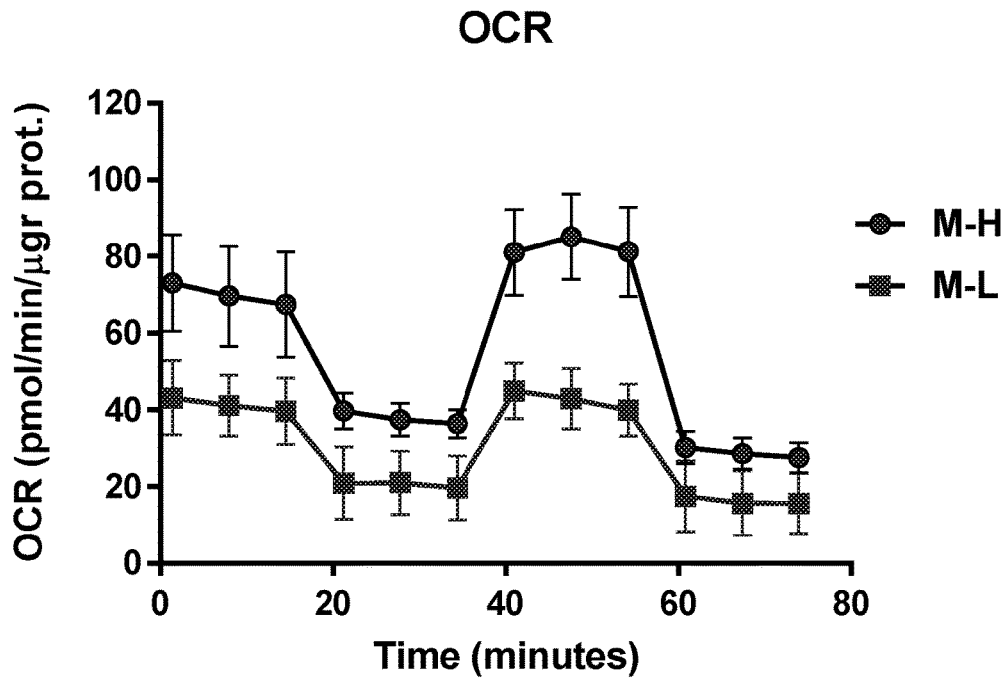
FIGS. 10A-10D show OCR data for MDA-MB-468 cell sub-populations.
Figure 10B:
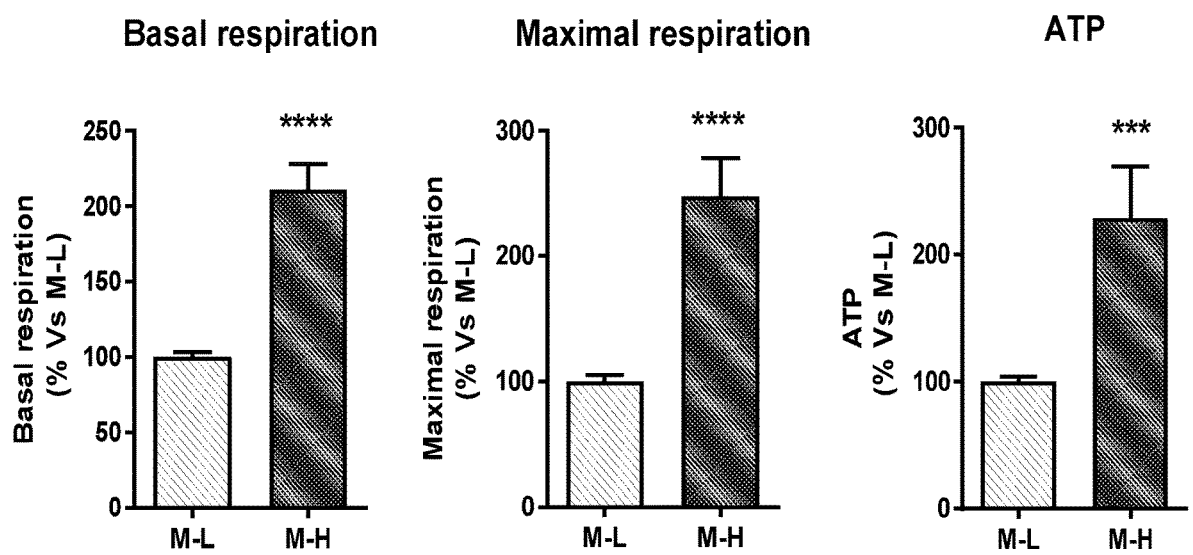
Figure 10C:
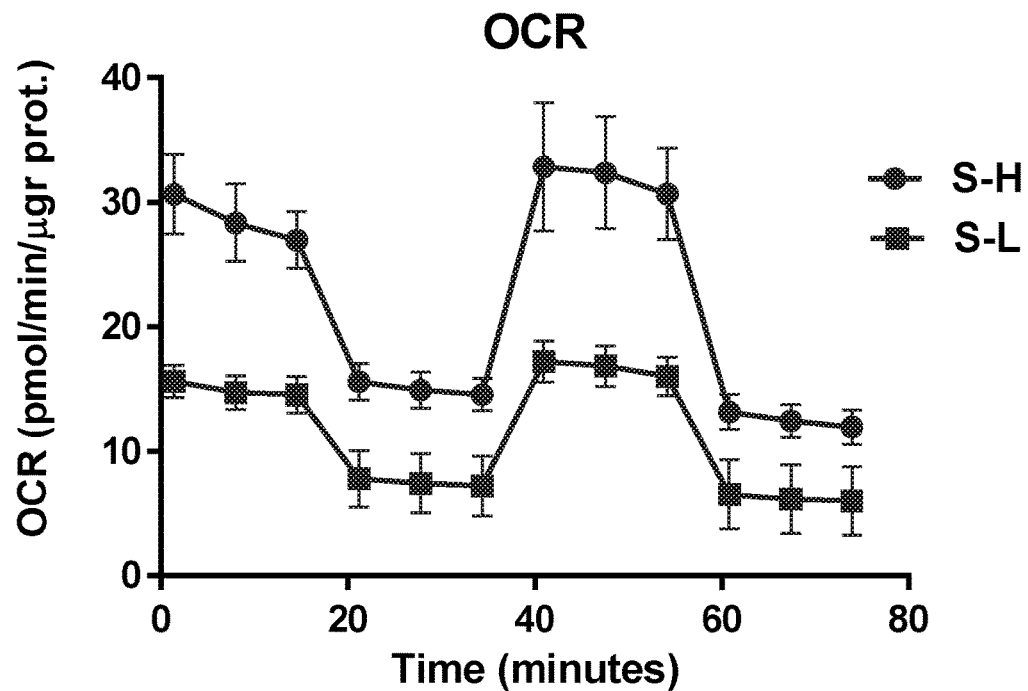
Figure 10D:
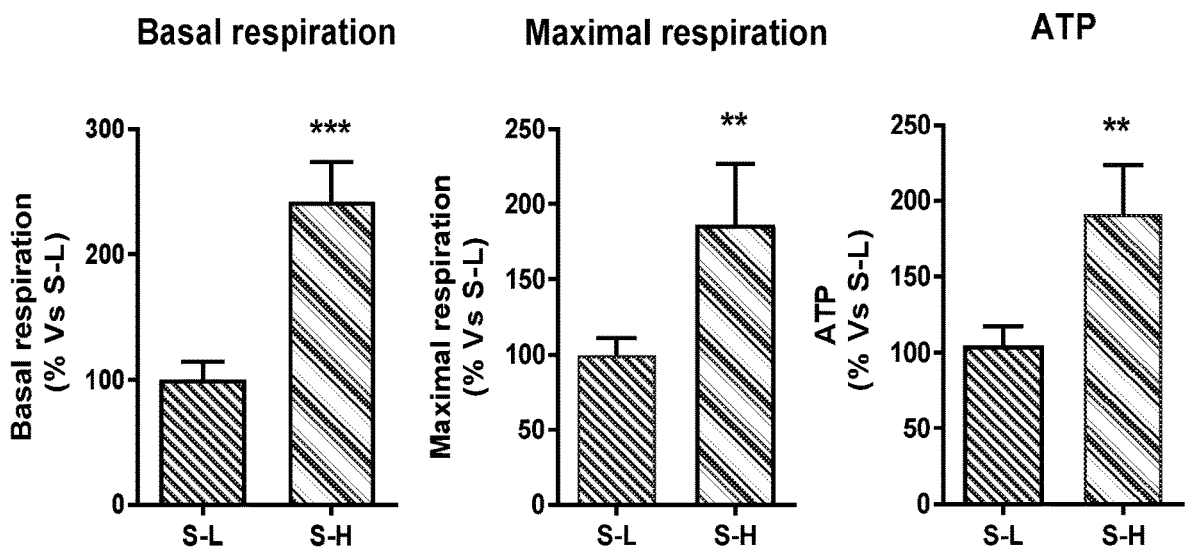

Although the data described above relates to breast cancer cells, it should be appreciated that the e-CSC phenotype is not limited to MCF7 cells. Data for MDA-MB-468 cell subpopulations shows that e-CSCs have common characteristics across different cancer types. FIGS. 9A-9D show cell cycle progression data for MDA-MB-468 e-CSCs. The e-CSCs were separated as described above, with respect to MCF7 cells. Representative images of the cell cycle analysis for M-L and M-H sub-populations of MDA-MB-468 cells grown in a monolayer are shown in FIG. 9A. The cell cycle progression for M-L, M-H, S-L, and S-H sub-populations is summarized the bar graphs in FIGS. 9B and 9C. Mitotracker Deep Red data is presented in FIG. 9D. The S-H cell sub-population derived from MDA-MB-468 cells shows the largest increases in cell cycle progression and mitochondrial mass. Virtually identical results were obtained with MCF7 cells, as discussed above.

FIGS. 10A-10D show OCR data for MDA-MB-468 cell sub-populations. Data for the M-L and M-H sub-populations are in FIGS. 10A and 10B, and data for the S-L and S-H sub-populations are in FIGS. 10C and 10D. As with the MCF7 data discussed above, the oxygen consumption rate (OCR) for these sub-populations was measured using the Seahorse XFe96 metabolic-flux analyzer. The high OCR in MDA-MB-468 cells directly correlates with high-flavin content. For example, M-H cells (from 2D-monolayers) and S-H cells (from 3D-spheroids) have the highest levels of OCR, as compared to the M-L and S-L sub-populations.

Figure 11A:
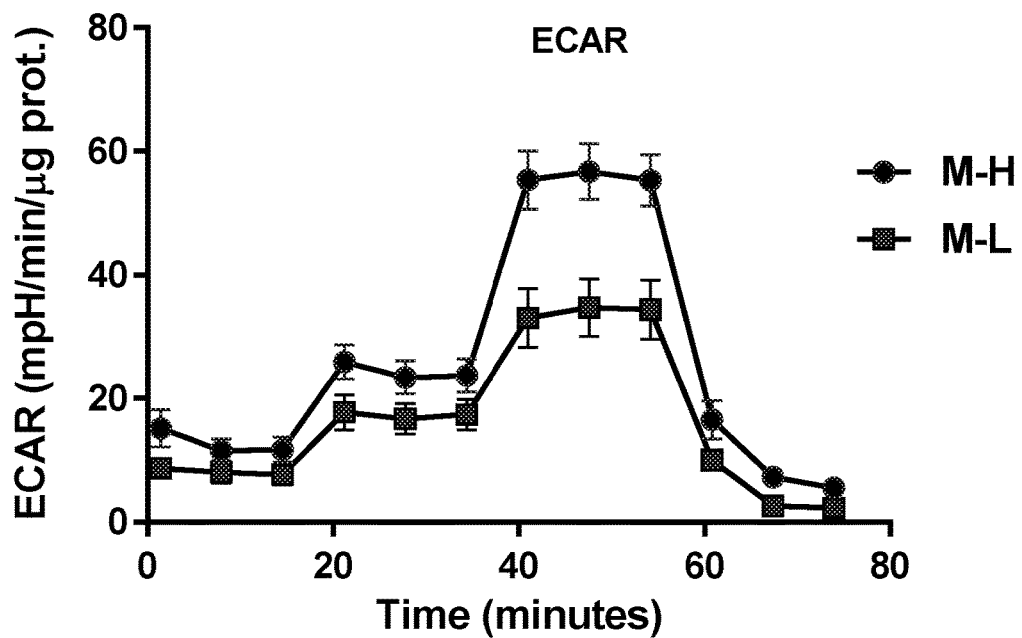
FIGS. 11A-11D show ECAR data for same MCF7 cell sub-populations
Figure 11B:
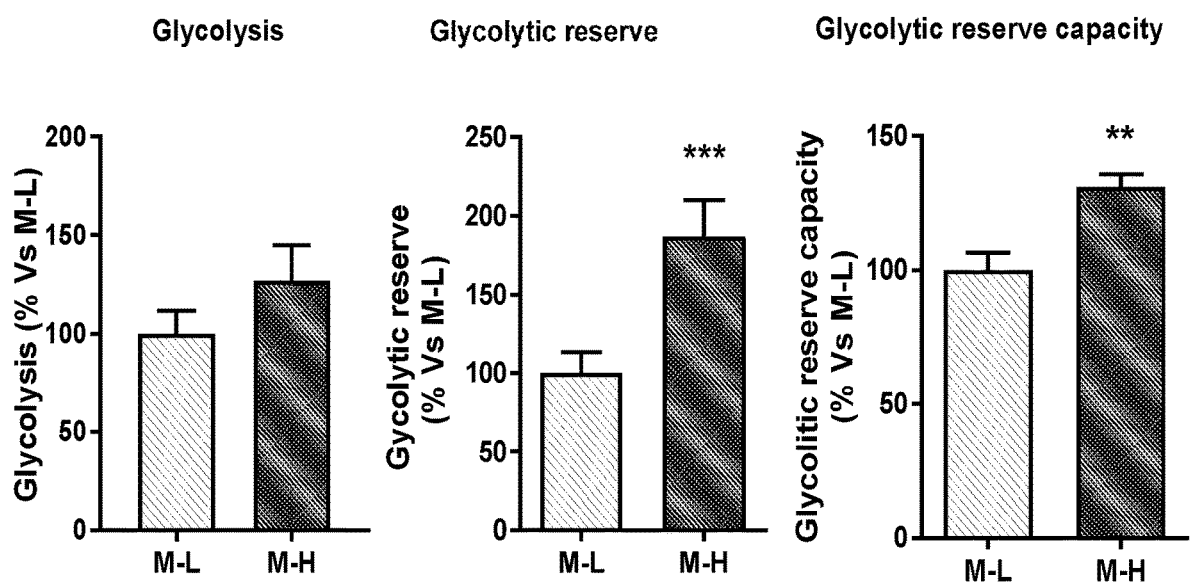
Figure 11C:
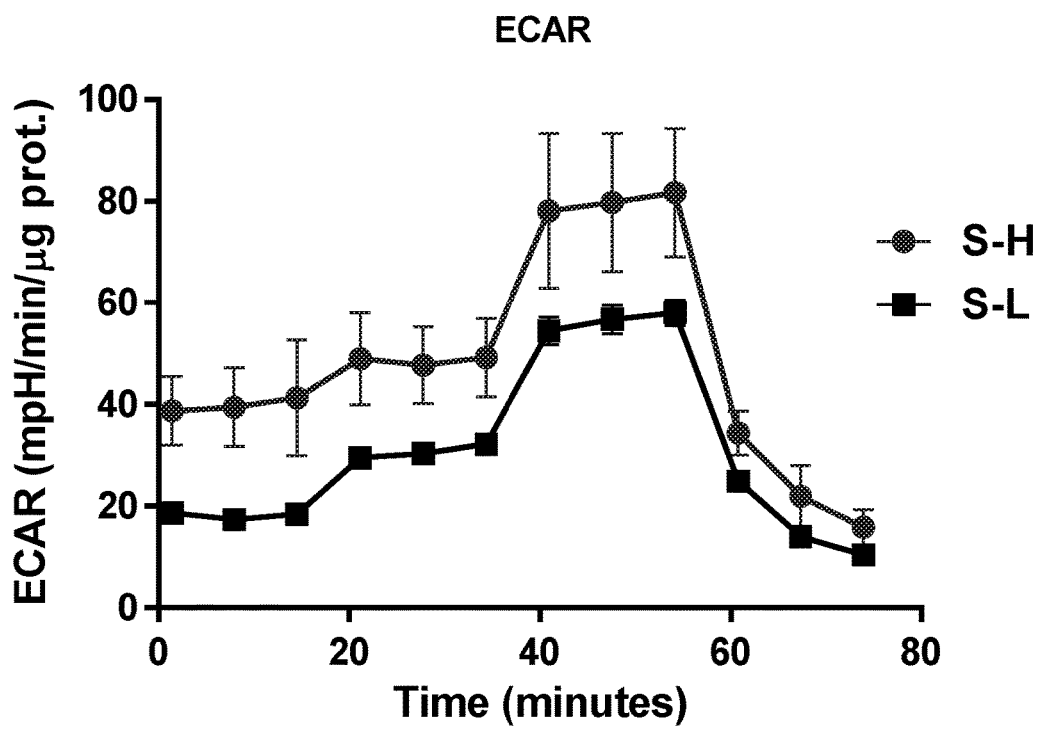
Figure 11D:
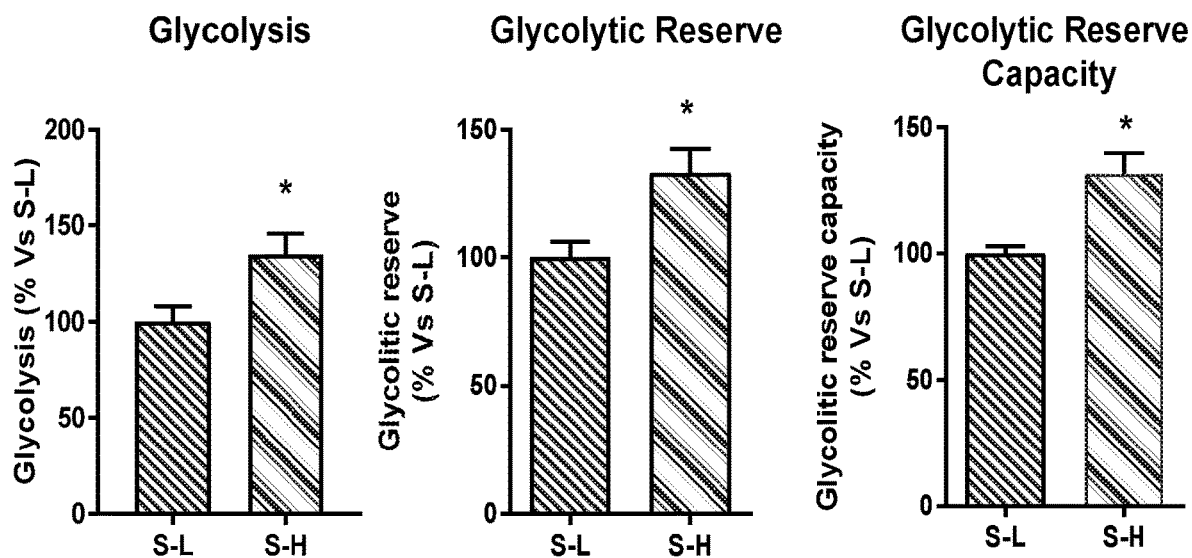

FIGS. 11A-11D show ECAR data for same MCF7 cell sub-populations measured using the Seahorse XFe96 metabolic-flux analyzer. FIGS. 11A and 11B show ECAR data for M-L vs. M-H sub-populations. FIGS. 11C and 11D show ECAR data for S-L vs. S-H sub-populations. The high ECAR in MDA-MD-468 cells directly correlates with high-flavin content. For example, M-H cells (from 2D-monolayers) and S-H cells (from 3D-spheroids) have the highest levels of ECAR, as compared to the M-L and S-L sub-populations.

The following paragraphs describe the proteomics analysis of e-CSCs derived from MCF7 3D-spheroid cells. Label-free unbiased proteomics analysis was used to describe the mechanistic basis for the biogenesis of e-CSCs. As a consequence, 225 proteins were identified that were significantly up-regulated by ≥1.5-fold. Conversely, 187 proteins were significantly down-regulated. For simplicity, the analysis focused on the specific protein products that were up-regulated and these are shown in Table 4, below. Interestingly, 48 of these proteins (representing ~20% of the total number) were specifically related to mitochondrial energy production and/or mitochondrial biogenesis. These 48 proteins are identified in Table 5, below. This is consistent with the functional observations described above, that e-CSCs demonstrate a near 4-fold increase in both mitochondrial mass and mitochondrial ATP production.

Table 6 shows further bioinformatics analysis, assembling the proteins into distinct functional groups. These functional classes include senescence, the anti-oxidant response, "stemness," cytoskeletal proteins (suggestive of an EMT), glutamine metabolism, NADH/NADPH synthesis, flavin-containing enzymes, autophagy/lysosomes, peroxisomes, and various cellular markers (epithelial, cell surface, S100 family proteins, RABs, annexins, PARP, calcium signaling). Interestingly, CDKN1A (p21 WAF), which is a CDK-inhibitor and senescence marker, is highly up-regulated by 17.22-fold in e-CSCs. This finding is consistent with the idea that CSCs originate from senescent cells.

However, e-CSCs are hyper-proliferative, so they likely escaped from senescence. This may have occurred through the over-expression of anti-oxidant enzymes or the over-production of NADH/NADPH. Loss of glutaredoxin expression is known to be sufficient to induce a senescence phenotype in cells, in a p21-dependent manner. Therefore, the observed over-expression of glutaredoxin (by 10.79-fold) may be sufficient to actually overcome senescence, allowing the creation of e-CSCs.

Importantly, glutaredoxin expression is known to drive mitochondrial biogenesis by directly regulating the activation state of two key mitochondrial proteins, namely HSP60 and DJ-1 (Park7) (35). HSP60 is a mitochondrial chaperone, which facilitates the proper folding of newly synthesized or imported mitochondrial proteins, while DJ-1 functionally maintains the activity of mitochondrial complex I and SOD2. As a consequence, glutaredoxin expression specifically maintains the integrity of mitochondria and elevates ATP synthesis. Glutaredoxin's ability to regulate mitochondrial energy production is also linked to cell cycle progression. As such, glutaredoxin allows cells to successfully pass through the G1/S transition, in a CDK4-dependent manner, thereby avoiding the cell-cycle arrest associated with senescence.

The 10.24-fold up-regulation of ALDH3A1 also provides significant anti-oxidant power, as ALDH isoforms are known to functionally increase the cellular levels of NADH/NADPH. Also, the main isoform up-regulated in e-CSCs, namely ALDH3A1, is known to be associated with tumorigenesis, metastasis and drug-resistance. Ingenuity Pathway Analysis (IPA) of the proteomics data sets referenced above confirmed the up-regulation of the anti-oxidant response and cell cycle progression in e-CSCs, as well as the changes in mitochondrial function IPA analysis of the proteomics data sets showed the activation of upstream regulator PPARGC-1-Alpha 1301, also known as PGC-1-Alpha, the major mitochondrial transcription factor. Also, a canonical pathway assessment identified the NRF2-mediated oxidative stress response pathway, and the cell cycle G2/M DNA damage checkpoint regulation pathway as significantly up-regulated.

In vivo data demonstrates that e-CSC proteins are transcriptionally up-regulated in human breast cancer patients. Pre-existing mRNA profiling data, obtained from the laser-capture analysis of N=28 human breast cancer patient tumor samples were used to determine if e-CSCs proteins were also transcriptionally up-regulated in human breast cancer cells in vivo. In this data set, breast cancer cells were physically separated from adjacent tumor stromal cells, using laser-captured mediated micro-dissection. The results of this intersection are presented in Table 7. The results indicate that out of the 225 proteins that were up-regulated in e-CSCs, nearly one-third of these gene products were transcriptionally up-regulated in human breast cancer cells (70/225=31.11%). In addition, many of these gene products were shared, including 20 mitochondrial related genes (20/70=28.57%). These results provide genetic evidence that demonstrates the clinical relevance of e-CSCs in the study of human breast cancers.

In connection with the prior work, a short anti-oxidant response signature in e-CSCs has been developed that predicts poor clinical outcome in breast cancer patients. The next paragraphs describe identifying subsets of e-CSCs proteins that have prognostic value in terms of predicting clinical outcome in human breast cancer patients. A well-defined set of high-risk ER(+) patients (luminal A) that received hormone-therapy (mostly-tamoxifen), with local Lymph-Node (LN) metastasis at diagnosis, as well as >150 months (12.5 years) of follow-up data were used for this assessment. In all of these cancer patients, their breast tumor tissues also underwent genomic transcriptional profiling.

Kaplan-Meier (K-M) analysis was used to specifically determine whether these e-CSCs proteins listed in Table 7 had prognostic value by determining their effects on the Hazard-Ratio (HR), by employing the Log-Rank test to determine statistical significance. Based on this analysis, a four-gene signature consisting of members of the anti-oxidant response and NAD(P)H metabolism, namely NQO1, ALDH5A1, TXNR and RRM2, was developed.

Table 8, below, summarizes the results. The other 66 gene products tested did not show this prognostic ability.

Figure 12A:
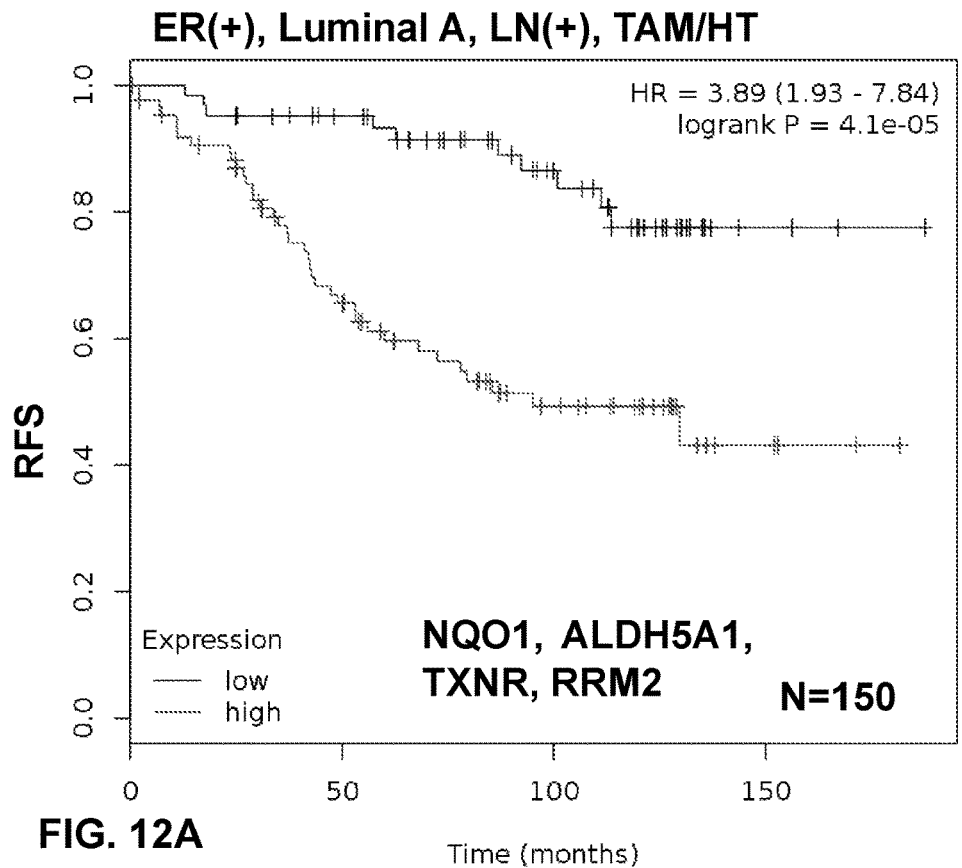
FIGS. 12A-12I show Kaplan-Meier curves for e-CSCs.
Figure 12B:
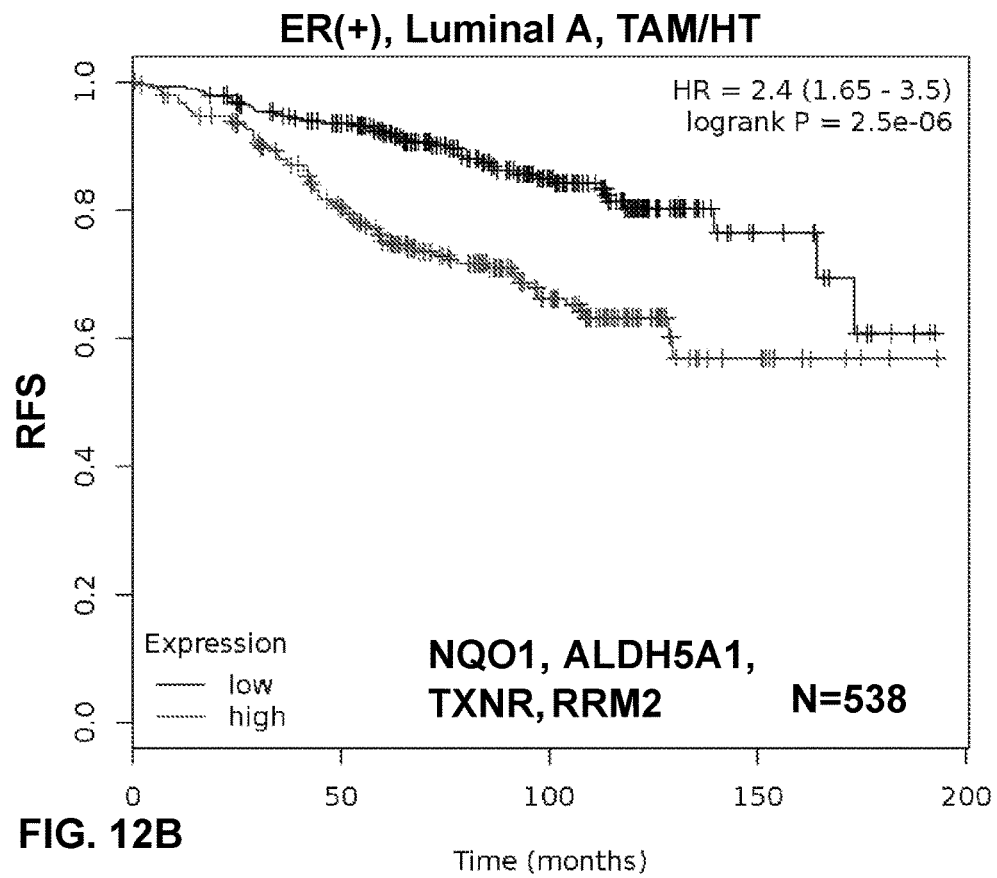
Figure 12C:
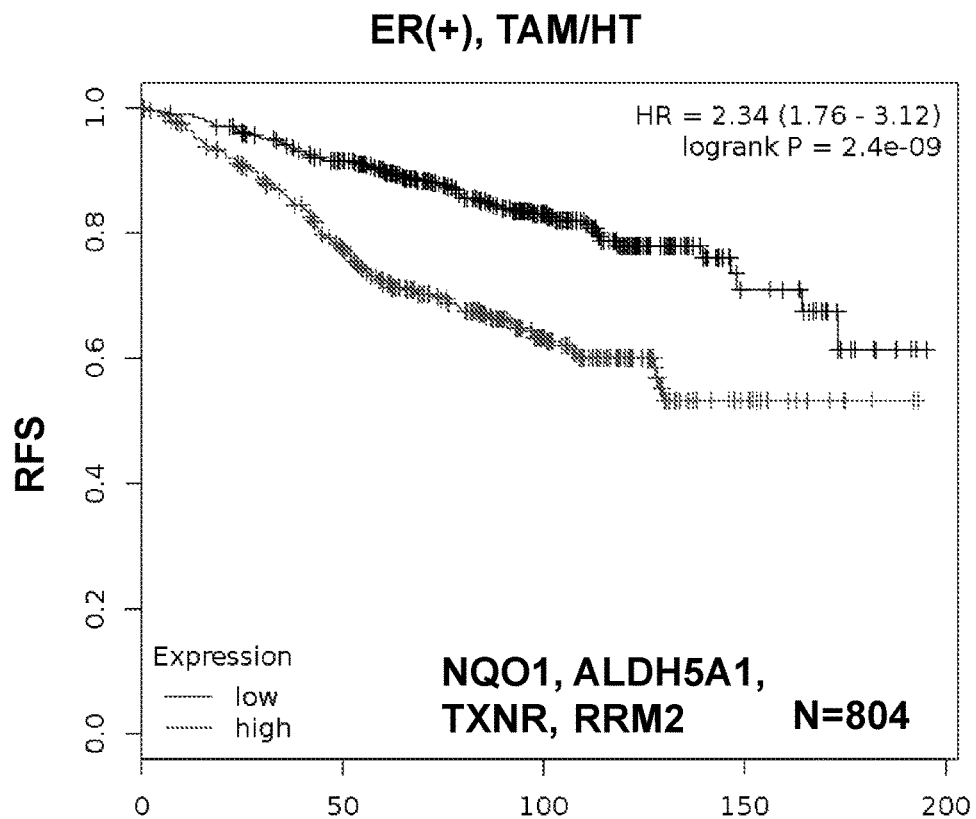
Figure 12D:
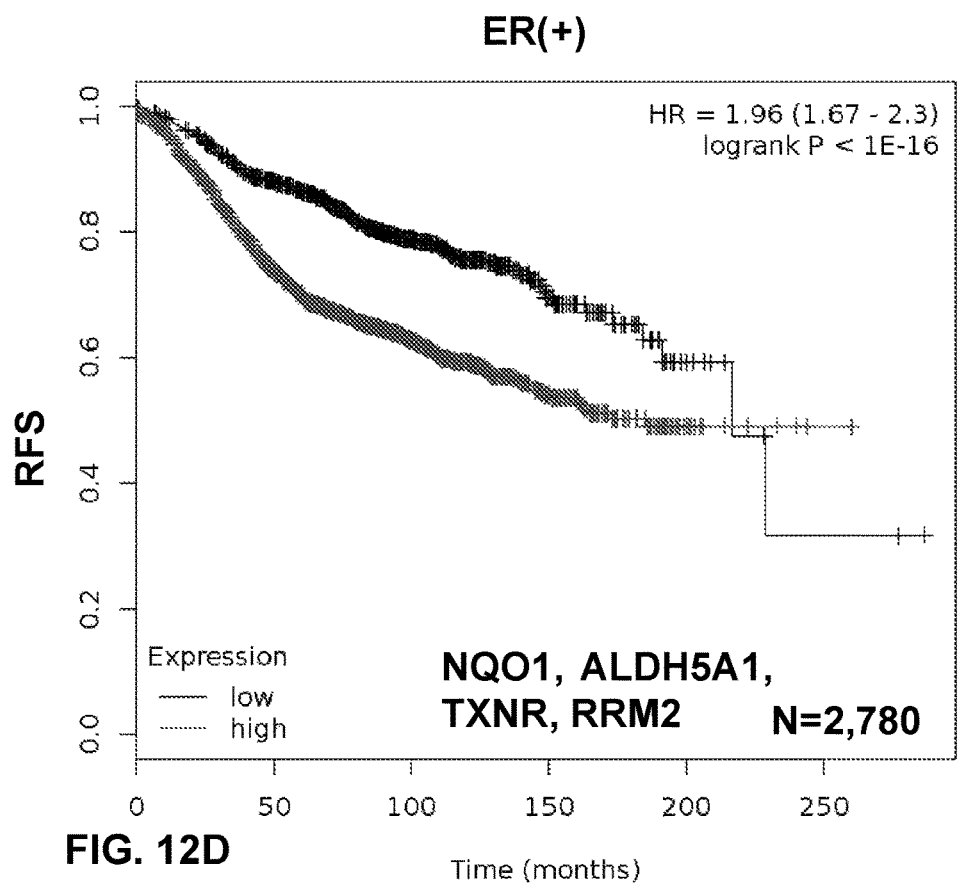
Figure 12E:
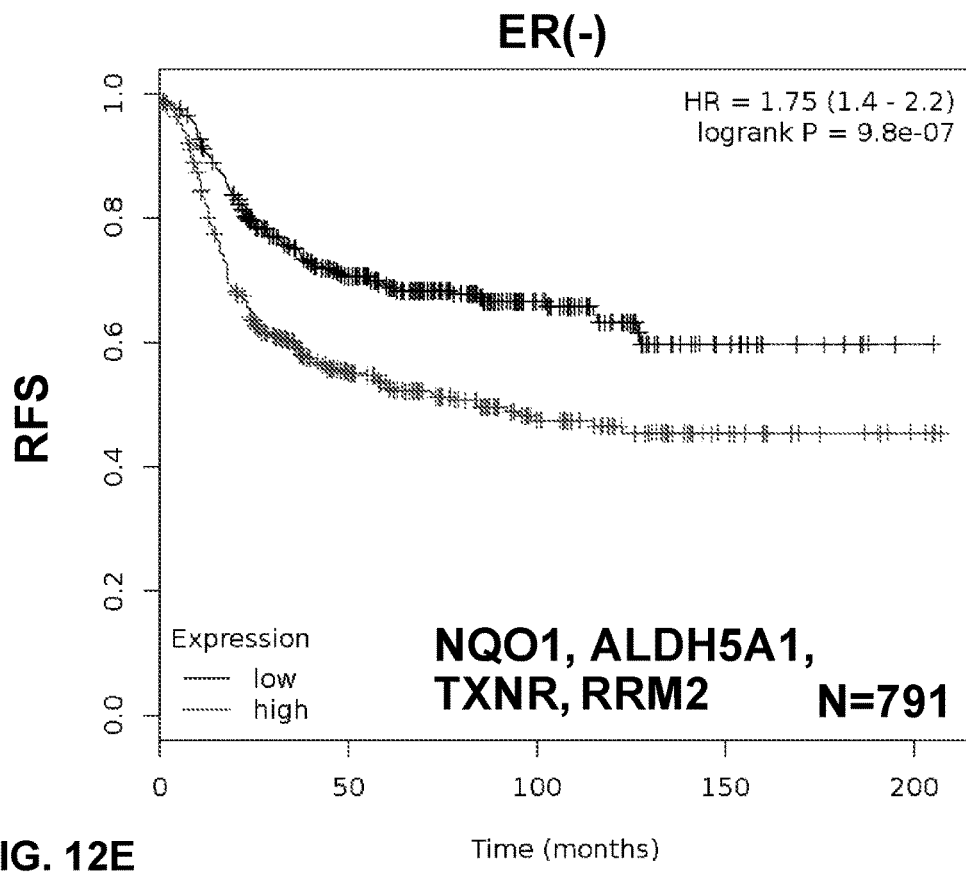
Figure 12F:
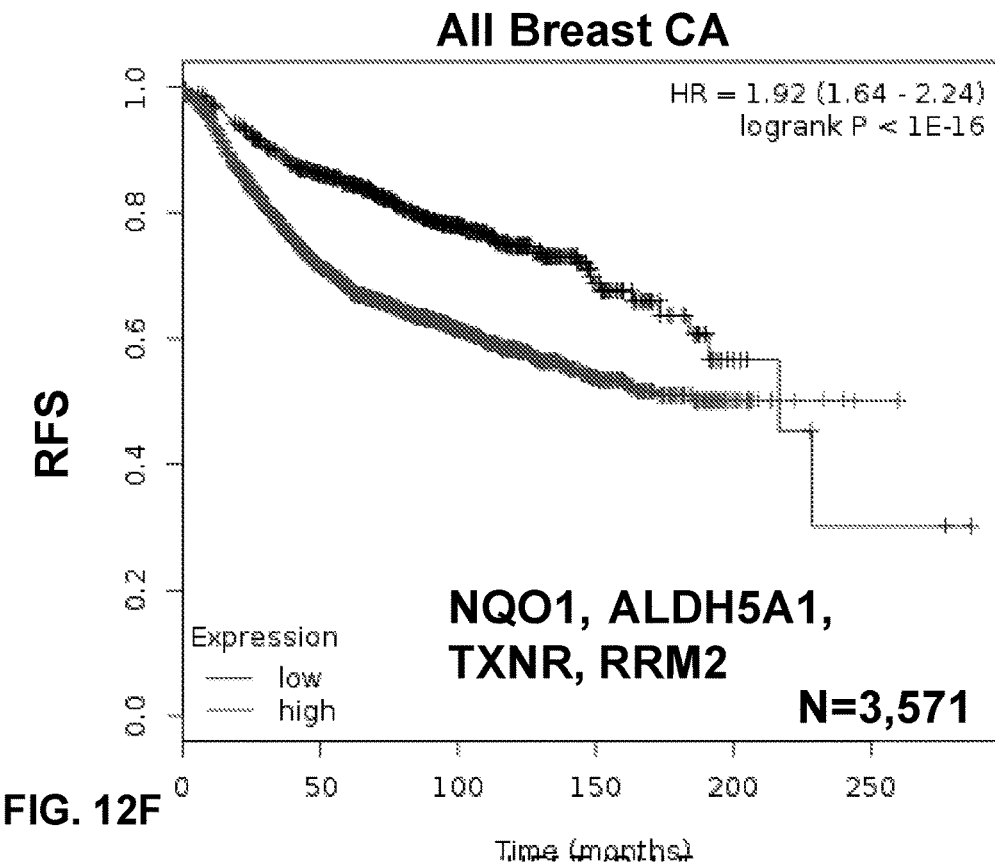
Figure 12G:
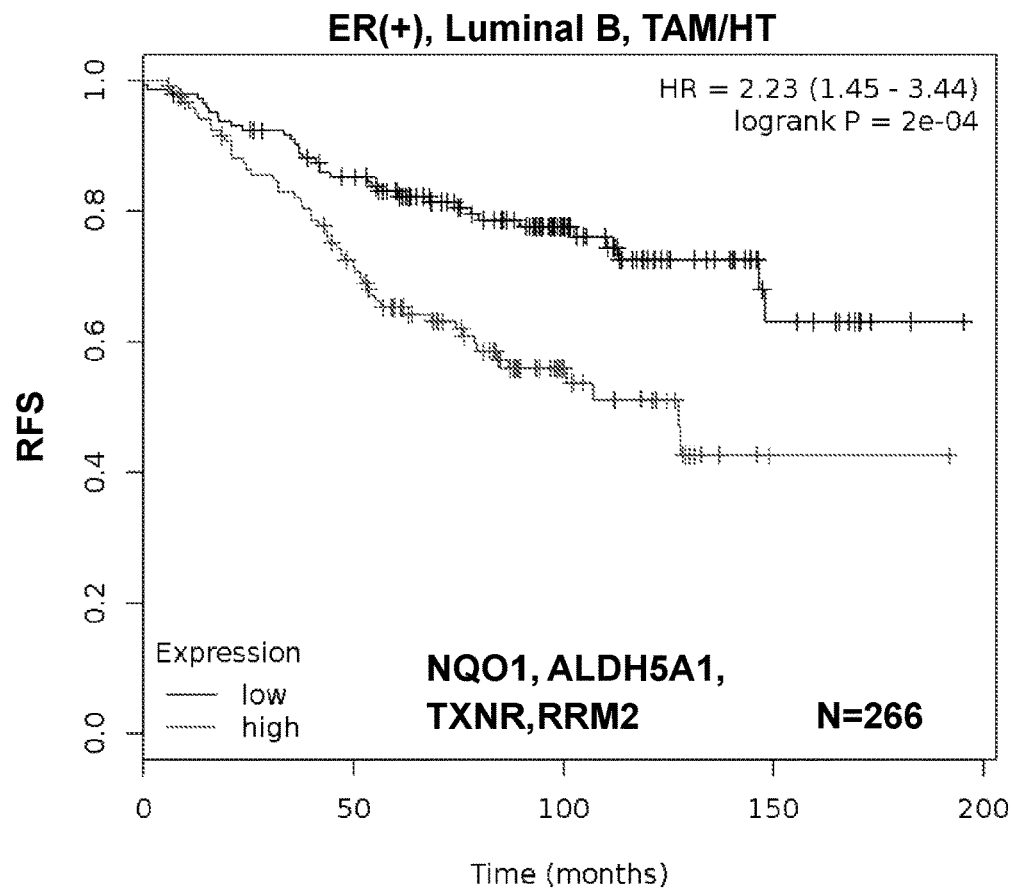
Figure 12H:
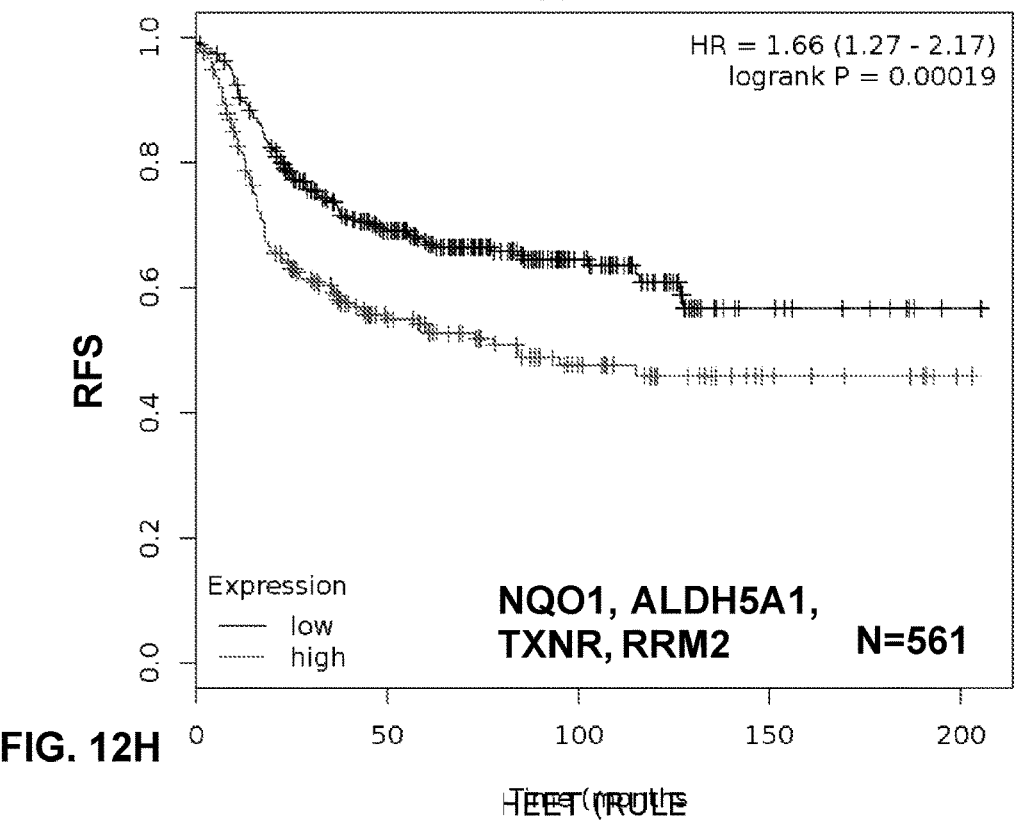
Figure 12I:
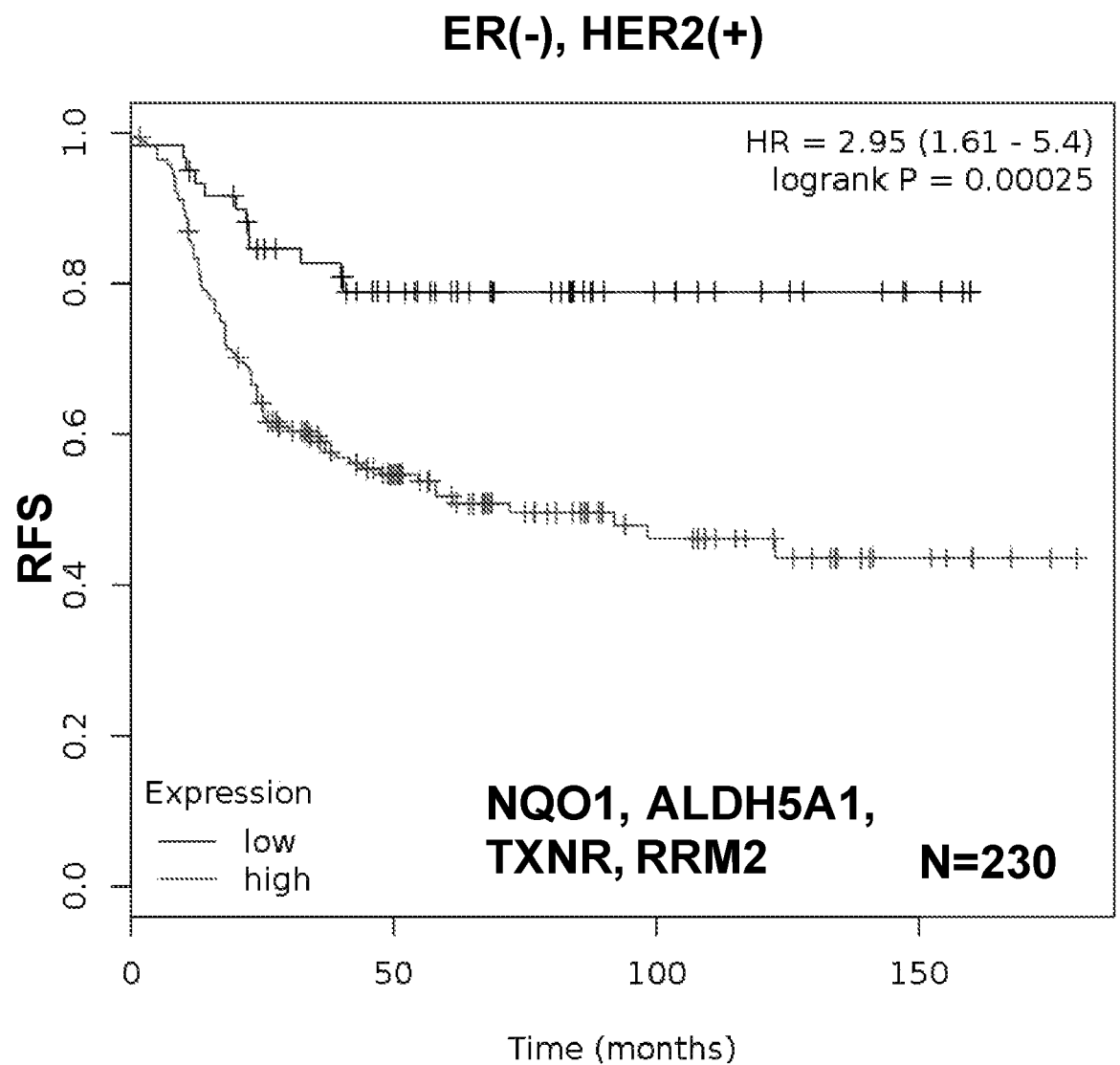

The K-M curves shown in FIGS. 12A-12I show that the anti-oxidant signature from e-CSCs of the present approach, NQO1, ALDH5A1, TXNR, and RRM2, effectively predicts tumor recurrence in all of the breast cancer sub-types tested. The patient groups examined were as follows: FIG. 12A shows ER(+), Luminal A sub-type, with Lymph-Node metastasis (LN(+)) at diagnosis, and treated with hormonal therapy (TAM/HT) (N=150). FIG. 12B shows ER(+), Luminal A sub-type, and treated with hormonal therapy (TAM/HT) (N=538). FIG. 12C shows ER(+) and treated with hormonal therapy (TAM/HT) (N=804). FIG. 12D shows all ER(+) (N=2,780). FIG. 12E shows all ER(−) (N=791). FIG. 12F shows all Breast Cancer (N=3,571). FIG. 12G shows ER(+), with the Luminal B sub-type (N=266). FIG. 12H shows ER(−), with the Basal sub-type (N=561). Finally, FIG. 12I shows ER(−) and HER2(+) (N=230).

These four gene products (NQO1, ALDH5A1, TXNR, and RRM2) were tested individually and all showed a >2-fold increase in the HR. In addition, when combined into a short signature, this resulted in a HR of nearly 4, with a p-value of 4.1e-05. As a consequence, under the present approach this anti-oxidant signature may be used to predict tumor recurrence (RFS) in patients receiving hormonal therapy.

Similarly, the inventors also recognized that the transcriptional elevation of 3 out of 4 of these gene products (ALDH5A1, TXNR and RRM2) was effectively able to predict distant metastasis (DMFS), with HRs of 2.86 to 3.64, and p-values of 0.003 to 0.00035. Table 9, below, shows these results. Thus, under the present approach a three-gene signature of ALDH5A1, TXNR and RRM2 may be used to identify a risk of distant metastasis.

It should be appreciated that the anti-oxidant response in e-CSCs allowed the inventors to successfully identify gene products with predictive value, for anticipating the onset of recurrence and/or metastasis, in breast cancer patients that ultimately underwent treatment failure, in response to hormonal therapy. K-M curves for larger groups of breast cancer patients are also shown FIGS. 12A-12I, which all showed significant prognostic value. These included patients that were ER(+) (N=2,780), shown in FIG. 12D, and ER(−) (N=791), shown in FIG. 12E, as well as all breast cancer sub-types, taken together (N=3,571), FIG. 12F. Therefore, this signature should have broad applicability in breast cancer, and other cancer types.

Embodiments of the present approach may involve measuring or determining the expression level of one or more genes in the e-CSC gene signature (NQO1, ALDH5A1, TXNR, and RRM2). The e-CSC gene signature has prognostic value with respect to the presence of e-CSCs, tumor recurrence due (at least in part) to e-CSCs, and distant metastasis due (at least in part) to e-CSCs. Up-regulation of one or more of the genes in the e-CSC gene signature may be used as a biomarker indicating that treatment for e-CSCs may be beneficial. Treatment for e-CSCs includes administering a pharmaceutically effective amount of at least one of an OXPHOS inhibitor and a CDK4/6 inhibitor. Additionally, e-CSCs may be treated with at least one mitochondrial biogenesis inhibitor. The treatment for e-CSCs may reduce or eliminate the likelihood of distant metastasis and/or tumor recurrence, and also may improve the effectiveness of other cancer therapies. It should be appreciated that gene expression levels may be measured using assays known to those having ordinary skill in the art. Gene expression may be measured based on the protein gene product, and common techniques include expression proteomics, Western blotting, and enzyme-linked immunosorbent assay (sometimes referred to as the ELISA assay). Gene expression may also be measured based on mRNA levels, and common techniques for mRNA level measurement include Northern blotting and reverse transcription then quantitative polymerase chain reaction (also called RT-qPCR). The threshold or baseline level(s) may be obtained from available literature and/or databases known in the art. Also, the threshold or baseline level(s) may be obtained from using an assay on a biologic sample representing a normal, healthy cell line. As those having at least an ordinary level of skill in the art will appreciate, the threshold or baseline level(s) may also be determined from in vivo data of patients having the same cancer, but no symptoms of tumor recurrence and/or distant metastasis. For example, in some embodiments the threshold data may be derived from the K-M-plotter source referenced above. In such embodiments, overexpression of one or more genes from the e-CSC gene signature in a mass, relative to the threshold data, indicates the presence of e-CSCs, and is prognostic of a likelihood of tumor recurrence and/or metastasis. The overexpression may be quantified as a ratio, and the ratio for determining overexpression depends on the embodiment. For example, in some embodiments overexpression may be determined if the quotient of the determined level divided by the threshold level is greater than 1.2. As further examples, in some embodiments the ratio may be 1.4, and in some embodiments is may be 1.6. It should be appreciated that the present approach is not limited to a particular threshold or metric for indicating overexpression—the person of ordinary skill in the art may identify a threshold data source for a particular cancer, and select the ratio for diagnosing overexpression of one or more genes of the e-CSC gene signature. This gene signature has prognostic value, as discussed above, and may be used as a biomarker of e-CSCs and the risk of tumor recurrence and/or metastasis due (at least in part) to e-CSCs. In turn, the e-CSC gene signature may be used to identify instances in which a pharmaceutically effective amount of at least one of an OXPHOS inhibitor, a CDK4/6 inhibitor, and/or a mitochondrial biogenesis inhibitor, may be administered to target e-CSCs in a mass, treat (i.e., reduce the likelihood of) distant metastasis and/or tumor recurrence, and treat cancer.

One explanation for the prognostic value of this compact gene signature is that an adaptive anti-oxidant response drives resistance to both chemotherapy and radiotherapy in cancer patients. In addition, TXNR and RRM2 both are key enzymes that provide the required precursors for nucleotide biosynthesis and, hence, cell cycle progression. The anti-oxidant response signatures of the present approach may also be useful for identifying breast cancer patients that could benefit from treatment with i) mitochondrial inhibitors or ii) CDK inhibitors, especially in the context of preventing tumor recurrence and/or distant metastasis. In some embodiments, these treatments may be used individually, or in combination with other therapies, such as (but not limited to) chemotherapy and radiation therapy. Thus, in the future, ROS production in e-CSCs, under both 2D and 3D microenvironmental conditions, will be used to validate that ROS production is driving this anti-oxidant response signature and contributes to their overall energetic phenotype.

The following paragraphs describe the methodologies and materials used in connection with the foregoing. It should be appreciated by those of ordinary skill in the art that variations may be made without departing from the present approach. With respect to the breast cancer cell models and other reagents, human breast cancer cell lines, MCF7 (ER (+)) and MDA-MB-468 (triple-negative), were obtained commercially from the ATCC. Both cell lines were maintained in Dulbecco's Modified Eagle Medium (DMEM; GIBCO), supplemented with 10% FBS, 1% Glutamax and 1% Penicillin-Streptomycin. All cell lines were maintained at 37° C. in 5% CO2. DPI and Ribociclib were purchased from Sigma-Aldrich, Inc.

Cell sorting: Flow-cytometry and collection of auto-fluorescent cells: MCF7 and MDA-MB-468 cells were first grown either as a 2D-monolayer or as 3D-spheroids. Then, they were collected and dissociated into a single-cell suspension, prior to analysis or sorting by flow-cytometry with the SONY SH800 Cell Sorter. Briefly, auto-fluorescent cells were excited with a 488 nm blue laser and selected at the intersection with filters 525/50 and 585/30. The "Low" and "High" auto-fluorescent cell sub-populations were selected by gating, within the auto-fluorescence signal. Only cells with the least (bottom 5%) or the most (top 5%) auto-fluorescence signal were collected. The cells outside the gates were discarded during sorting, due to the gate settings. However, such settings are required, to ensure high-purity during sorting. To better characterize the auto-fluorescent cell sub-populations, the following flow-cytometry markers were used: ALDEFLUOR-assay (StemCell technologies, Durham, N.C., USA); and MitoTracker Deep Red (Thermo Fisher Scientific). Hoescht (Thermo Fisher Scientific) was used for cell cycle analysis. Data were analyzed with FlowJo 10.1 software.

Preparing cells for auto-fluorescent cell sorting by flow-cytometry: The following protocol was used to acquire and sort auto-fluorescent cells from 2D-monolayers or 3D-spheroid cell suspensions. For 2D-monolayers, MCF7 and MDA-MB-468 were seeded in a 225 cm2 flask and when ~70% confluence was reached, 5 ml of 0.025% trypsin was added to the flasks and incubated at 37° C. for 5 minutes. After that the cells were re-suspended in media and centrifuged at 300 g for 5 min. After centrifugation, the cell pellets were adjusted to a concentration of 106 cells/ml in in PBS Ca/Mg for acquisition or in sorting buffer (1×PBS containing 3% (v/v) FBS and 2 mM EDTA) for FACS.

For 3D-spheroid suspensions, after 5 days of growth under low-attachment condition, the spheres were collected from six 225 cm2 flasks pre-coated with poly-HEMA and gently centrifuged at 100 g for 5 min. After centrifugation, 1 ml of 0.025% of trypsin was added to the "sphere-pellet" and incubated them at 37° C. for 5 minutes. Using a 25-gauge needle, the sphere-suspension was passed through the syringe 4 times. The sphere suspension was then centrifuged again at 100 g for 5 min, and the sphere-pellet was re-suspended in i) PBS Ca/Mg for acquisition or ii) in sorting buffer (1×PBS containing 3% (v/v) FBS and 2 mM EDTA) for FACS and the suspension was "syringed" again 4 times. After creating these single-cell suspensions, they were subjected to standard flow-cytometry (using the SONY SH800 Cell Sorter) to isolate the auto-fluorescent cell sub-populations, as indicated above. Examples of flow-cytometry plots are included in the figures, and the gating strategy is shown.

Mammosphere formation assay (for generating 3D-spheroids): A single-cell suspension was prepared using enzymatic, and manual disaggregation (25 gauge needle). Then, cells were plated at a density of 500 cells/cm2 in mammosphere medium (DMEM-F12+B27+20 ng/ml EGF+Pen-Strep) under non-adherent conditions, in culture dishes pre-coated with (2-hydroxyethylmethacrylate) (poly-HEMA, Sigma, #P3932), called "mammosphere plates." Cells were grown for 5 days and maintained in a humidified incubator at 37° C. After 5 days of culture, 3D-spheres >50 µm were counted using an eye piece ("graticule"), and the percentage of cells plated which formed spheres was calculated and is referred to as percent mammosphere formation, and was normalized to one (1=100% MSF). Mammosphere formation efficiency was analyzed in both the "low" and "high" sub-populations of auto-fluorescent cells, generated from either 2D-monolayers (M-L vs. M-H) or 3D-spheroids (S-L vs. S-H). All mammosphere experiments were performed in triplicate, at least 3 times independently.

ALDEFLUOR assay: The level of ALDH activity was assessed, by using the fluorescent reagent ALDEFLUOR. The ALDEFLUOR kit (StemCell technologies, Durham, N.C., USA) was used to detect the cell sub-populations with various amounts of ALDH enzymatic activity by FACS (Attune NxT Flow Cytometer). Briefly, 1×105 were incubated in 1 ml ALDEFLUOR assay buffer containing ALDH substrate (5 µl/ml) for 40 minutes at 37° C. In each experiment a sample of cells was stained under identical conditions with 30 µM of diethylaminobenzaldehyde (DEAB), a specific ALDH inhibitor, as a negative control The ALDH-positive population was established, according to the manufacturer's instructions and was evaluated using 50,000 cells. All the ALDH experiments were performed three times independently.

Seahorse XFe96 metabolic flux analysis: Real-time oxygen consumption rates (OCR) and extracellular acidification rates (ECAR) rates were determined using the Seahorse Extracellular Flux (XFe96) analyzer (Seahorse Bioscience, USA). Briefly, 2×104 cells per well were seeded into XFe96 well cell culture plates after sorting, and incubated for 12 h to allow cell attachment. After 12 hours of incubation, cells were washed in pre-warmed XF assay media (or for OCR measurement, XF assay media supplemented with 10 mM glucose, 1 mM Pyruvate, 2 mM L-glutamine and adjusted at 7.4 pH). Cells were then maintained in 175 µL/well of XF assay media at 37° C., in a non-CO2 incubator for 1 hour. During the incubation time, 25 µL of 80 mM glucose, 9 µM oligomycin, and 1M 2-deoxyglucose (for ECAR measurement) or 10 µM oligomycin, 9 µM FCCP, 10 µM rotenone, 10 µM antimycin A (for OCR measurement), was loaded in XF assay media into the injection ports in the XFe96 sensor cartridge (20, 21). Measurements were normalized by protein content (SRB assay) and Hoechst 33342 content. Data sets were analyzed using XFe96 software and GraphPad Prism software, using one-way ANOVA and Student's t-test calculations. All experiments were performed in quintuplicate, three times independently.

Vital mitochondrial staining: Cells were trypsinized and re-suspended into a 1×106 cell/ml solution in PBS. 10 nM of MitoTracker Deep-Red (Thermo Fisher Scientific) was added for 30 minutes at 37° C. before centrifugation and re-suspension in PBS Ca/Mg for FACS analysis (ATTUNE NxT) or Cell Sorting (SONY SH 800). All subsequent steps were performed in the dark. Data analysis was performed using FlowJo software.

Cell cycle analysis: The cell-cycle analysis was performed on the auto-fluorescent cell sub-populations, by FACS analysis using the SONY Cell Sorter. Briefly, after trypsinization, the re-suspended cells were incubated with 10 ng/ml of Hoescht solution (Thermo Fisher Scientific) for 40 minutes at 37° C. under dark conditions. Following a 40 minute period, the cells were washed and re-suspended in PBS Ca/Mg for acquisition or in sorting buffer (1×PBS containing 3% (v/v) FBS and 2 mM EDTA) for FACS. We analyzed 50,000 events per condition. Gated cells were manually-categorized into cell-cycle stages.

Statistical analysis: All analyses were performed with GraphPad Prism 6. Data were represented as mean±SD (or ±SEM where indicated). All experiments were conducted at least 3 times independently, with >3 technical replicates for each experimental condition tested (unless stated otherwise, e.g., when representative data is shown). Statistically significant differences were determined using the Student's t test or the analysis of variance (ANOVA) test. For the comparison among multiple groups, one-way ANOVA were used to determine statistical significance. $P<0.05$ was considered significant and all statistical tests were two-sided. In the drawings, * indicates $P<0.05$;  indicates $P<0.005$; and * indicates $P<0.0005$.

Proteomics analysis: Label-free unbiased proteomics and Ingenuity pathway analysis (IPA) were carried out, essentially as previously described, using standard protocols, with relatively minor modifications. For IPA, unbiased interrogation and analysis of the proteomic data sets was carried out by employing the IPA bioinformatics platform (Ingenuity systems, http://www.ingenuity.com). IPA assists with data interpretation, via the grouping of differentially expressed genes or proteins into known functions and pathways. Pathways with a z score of >+2 were considered as significantly activated, while pathways with a z score of <−2 were considered as significantly inhibited.

Clinical relevance of e-CSC marker proteins: To validate the clinical relevance of our findings, the inventors first assessed whether the identified e-CSC targets in MCF7 cells were also transcriptionally upregulated in human breast cancer cells in vivo. For this purpose, the inventors employed a published clinical data set of N=28 breast cancer patients in which their tumor samples were subjected to laser-capture micro-dissection (26), to physically separate epithelial cancer cells from their adjacent tumor stroma.

Kaplan-Meier (K-M) analyses: To perform K-M analysis on mRNA transcripts, the inventors used an open-access online survival analysis tool to interrogate publically available microarray data from up to 3,455 breast cancer patients. This allowed us to determine their prognostic value (27). For this purpose, the inventors primarily analyzed data from ER(+) patients that were LN(+) at diagnosis and were of the luminal A sub-type, that were primarily treated with tamoxifen and not other chemotherapy (N=150 patients). In this group, 100% the patients received some form of hormonal therapy and ~95% of them received tamoxifen. Biased and outlier array data were excluded from the analysis. This allowed us to identify metabolic gene transcripts, with significant prognostic value. Hazard-ratios were calculated, at the best auto-selected cut-off, and p-values were calculated using the log-rank test and plotted in R. K-M curves were also generated online using the K-M-plotter (as high-resolution TIFF files), using univariate analysis: http://kmplot.com/analysis/index.php?p=service&cancer=breast. This allowed us to directly perform in silico validation of these metabolic biomarker candidates. The 2017 version of the database was utilized for all these analyses, while virtually identical results were also obtained with the 2014 and 2012 versions.

The terminology used herein is for the purpose of describing particular embodiments only and is not intended to be limiting of the approach. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

TABLE 4

Proteomic analysis of e-CSCs, derived from MCF7 3D-Spheroids

| Symbol | Gene Description | Fold-Change (Up-regulation) |
|---|---|---|
| BCAS1 | Breast carcinoma-amplified sequence 1 | 119.37 |
| CDKN1A | Cyclin-dependent kinase inhibitor 1 (p21-WAF/CDK-inhibitor) | 17.22 |
| GLRX | Glutaredoxin-1 | 10.79 |
| ALDH3A1 | Aldehyde dehydrogenase, dimeric NADP-preferring | 10.24 |
| CEACAM6 | Carcinoembryonic antigen-related cell adhesion molecule 6 | 9.66 |
| CYP1A1 | Cytochrome P450 1A1 | 6.60 |
| ELMOD2 | ELMO domain-containing protein 2 | 4.73 |
| MAOA | Amine oxidase [flavin-containing] A | 4.73 |
| KRT10 | Keratin, type I cytoskeletal 10 | 4.59 |
| IGFBP2 | Insulin-like growth factor-binding protein 2 | 4.20 |
| QPRT | Nicotinate-nucleotide pyrophosphorylase [carboxylating] | 3.72 |
| MVP | Major vault protein | 3.61 |
| CEACAM5 | Carcinoembryonic antigen-related cell adhesion molecule 5 | 3.38 |
| CLU | Clusterin | 3.13 |
| QSOX1 | Sulfhydryl oxidase 1 | 2.93 |
| CIB1 | Calcium and integrin-binding protein 1 | 2.90 |
| VGF | Neurosecretory protein VGF | 2.90 |
| ANXA1 | Annexin A1 | 2.87 |
| AKR1C3 | Aldo-keto reductase family 1 member C3 | 2.79 |
| LAMA5 | Laminin subunit alpha-5 | 2.72 |
| CDC42BPG | Serine/threonine-protein kinase MRCK gamma | 2.69 |
| RAB27B | Ras-related protein Rab-27B | 2.69 |
| CHMP6 | Charged multivesicular body protein 6 | 2.62 |
| TUBA4A | Tubulin alpha-4A chain | 2.60 |
| PARP4 | Poly [ADP-ribose] polymerase 4 | 2.55 |
| RAB27A | Ras-related protein Rab-27A | 2.54 |
| EVPL | Envoplakin | 2.48 |
| KLK11 | Kallikrein-11 | 2.46 |
| MAOB | Amine oxidase [flavin-containing] B | 2.45 |
| DPP7 | Dipeptidyl peptidase 2 | 2.43 |
| AKR1C2 | Aldo-keto reductase family 1 member C2 | 2.41 |
| SFXN3 | Sideroflexin-3 | 2.40 |
| MIC13 | MICOS complex subunit MIC13, mitochondrial | 2.36 |
| GM2A | Ganglioside GM2 activator | 2.36 |
| SCRN2 | Secernin-2 | 2.34 |
| SULT1A1 | Sulfotransferase 1A1 | 2.34 |
| RRM2 | Ribonucleoside-diphosphate reductase subunit M2 | 2.34 |
| SERPINA3 | Alpha-1-antichymotrypsin | 2.33 |
| SLC6A14 | Sodium-and chloride-dependent neutral and basic amino acid transporter B(0+) | 2.30 |
| AGA | N(4)-(beta-N-acetylglucosaminyl)-L-asparaginase | 2.30 |
| SYTL2 | Synaptotagmin-like protein 2 | 2.30 |
| MPV17 | Protein Mpv17 | 2.28 |
| KIAA0319L | Dyslexia-associated protein KIAA0319-like protein | 2.25 |
| B3GAT3 | Galactosylgalactosylxylosylprotein 3-beta-glucuronosyltransferase 3 | 2.22 |
| PON2 | Serum paraoxonase/arylesterase 2 | 2.22 |
| OXSM | 3-oxoacyl-[acyl-carrier-protein] synthase, mitochondrial | 2.22 |
| TOM1L2 | TOM1-like protein 2 | 2.22 |
| STOM | Erythrocyte band 7 integral membrane protein | 2.18 |

TABLE 4-continued

Proteomic analysis of e-CSCs, derived from MCF7 3D-Spheroids

| Symbol | Gene Description | Fold-Change (Up-regulation) |
|---|---|---|
| MROH1 | Maestro heat-like repeat-containing protein family member 1 | 2.17 |
| PI4K2A | Phosphatidylinositol 4-kinase type 2-alpha | 2.17 |
| FECH | Ferrochelatase, mitochondrial | 2.16 |
| MCU | Calcium uniporter protein, mitochondrial | 2.13 |
| S100P | Protein S100-P | 2.11 |
| RDH13 | Retinol dehydrogenase 13 | 2.08 |
| PPL | Periplakin | 2.08 |
| TSPAN31 | Tetraspanin-31 | 2.03 |
| TIMP1 | Metalloproteinase inhibitor 1 | 2.02 |
| GCLC | Glutamate--cysteine ligase catalytic subunit | 2.01 |
| NEBL | Nebulette | 2.01 |
| MUC5B | Mucin-5B | 1.98 |
| CTSH | Cathepsin H | 1.98 |
| GNS | N-acetylglucosamine-6-sulfatase | 1.97 |
| S100A10 | Protein S100-A10 | 1.96 |
| INPP4B | Type II inositol 3,4-bisphosphate 4-phosphatase | 1.96 |
| PHYKPL | 5-phosphohydroxy-L-lysine phospho-lyase | 1.95 |
| ASAH1 | Acid ceramidase | 1.94 |
| DHRS1 | Dehydrogenase/reductase SDR family member 1 | 1.93 |
| PEX14 | Peroxisomal membrane protein PEX14 | 1.91 |
| PTGR1 | Prostaglandin reductase | 1.91 |
| NQO2 | Ribosyldihydronicotinamide dehydrogenase [quinone] | 1.90 |
| STARD3NL | STARD3 N-terminal-like protein | 1.88 |
| MGST1 | Microsomal glutathione S-transferase | 1.88 |
| CMC1 | COX assembly mitochondrial protein homolog | 1.87 |
| DGAT1 | Diacylglycerol O-acyltransferase 1 | 1.87 |
| RAB24 | Ras-related protein Rab-24 | 1.87 |
| GDPD3 | Lysophospholipase D GDPD3 | 1.86 |
| DCLK1 | Serine/threonine-protein kinase DCLK1 | 1.85 |
| PSAP | Prosaposin | 1.85 |
| MGST3 | Microsomal glutathione S-transferase 3 | 1.84 |
| ANO10 | Anoctamin-10 | 1.84 |
| CASK | Peripheral plasma membrane protein CASK | 1.84 |
| LGALS3BP | Galectin-3-binding protein | 1.83 |
| GAA | Lysosomal alpha-glucosidase | 1.83 |
| ISCU | Iron-sulfur cluster assembly enzyme ISCU, mitochondrial | 1.83 |
| GALNS | N-acetylgalactosamine-6-sulfatase | 1.82 |
| DECR2 | Peroxisomal 2,4-dienoyl-CoA reductase | 1.81 |
| ABAT | 4-aminobutyrate aminotransferase, mitochondrial | 1.81 |
| PALM3 | Paralemmin-3 | 1.81 |
| ABCB6 | ATP-binding cassette sub-family B member 6, mitochondrial | 1.80 |
| GFER | FAD-linked sulfhydryl oxidase ALR | 1.80 |
| CD59 | CD59 glycoprotein | 1.80 |
| SLC39A11 | Zinc transporter ZIP11 | 1.80 |
| CAPN2 | Calpain-2 catalytic subunit | 1.79 |
| FAM174B | Membrane protein FAM174B | 1.79 |
| TMEM160 | Transmembrane protein 160 | 1.79 |
| ACADSB | Short/branched chain specific acyl-CoA dehydrogenase, mitochondrial | 1.79 |
| FAM8A1 | Protein FAM8A1 | 1.79 |
| CAPS | Calcyphosin | 1.79 |
| ARMC10 | Armadillo repeat-containing protein 10 | 1.78 |
| TMTC3 | Transmembrane and TPR repeat-containing protein 3 | 1.78 |
| SCFD2 | Sec1 family domain-containing protein 2 | 1.78 |
| HDHD3 | Haloacid dehalogenase-like hydrolase domain-containing protein 3 | 1.78 |
| RETSAT | All-trans-retinol 13,14-reductase | 1.77 |
| COQ9 | Ubiquinone biosynthesis protein COQ9, mitochondrial | 1.77 |
| SPATA20 | Spermatogenesis-associated protein 20 | 1.77 |
| EML2 | Echinoderm microtubule-associated protein-like 2 | 1.77 |
| ALDH5A1 | Succinate-semialdehyde dehydrogenase, mitochondrial | 1.76 |
| GRN | Granulins | 1.76 |
| CPT2 | Carnitine O-palmitoyltransferase 2, mitochondrial | 1.76 |
| PEX11B | Peroxisomal membrane protein PEX11B | 1.76 |
| HMGCL | Hydroxymethylglutaryl-CoA lyase, mitochondrial | 1.75 |
| GSTK1 | Glutathione S-transferase kappa 1 | 1.75 |
| DHRS7B | Dehydrogenase/reductase SDR family member 7B | 1.75 |
| FDXR | NADPH:adrenodoxin oxidoreductase, mitochondrial | 1.75 |
| EPS8L1 | Epidermal growth factor receptor kinase substrate 8-like protein 1 | 1.74 |
| SLC22A18 | Solute carrier family 22 member 18 | 1.74 |
| CYCS | Cytochrome c | 1.74 |
| MAPRE3 | Microtubule-associated protein RP/EB family member 3 | 1.74 |
| SQOR | Sulfide:quinone oxidoreductase, mitochondrial | 1.73 |
| PDIA5 | Protein disulfide-isomerase A5 | 1.73 |
| HIGD1C | HIG1 domain family member 1C | 1.72 |
| EML3 | Echinoderm microtubule-associated protein-like 3 | 1.72 |
| PCLAF | PCNA-associated factor | 1.72 |
| ATP6V0A1 | V-type proton ATPase 116 kDa subunit a isoform 1 | 1.71 |
| TAOK3 | Serine/threonine-protein kinase TAO3 | 1.71 |
| ITGAV | Integrin alpha-V | 1.71 |
| CAMK2D | Calcium/calmodulin-dependent protein kinase type II subunit delta | 1.70 |
| SLC9A1 | Sodium/hydrogen exchanger 1 | 1.69 |
| CALML5 | Calmodulin-like protein 5 | 1.69 |
| HMOX1 | Heme oxygenase 1 | 1.69 |
| RNASET2 | Ribonuclease T2 | 1.69 |
| SELENBP1 | Methanethiol oxidase | 1.68 |
| ACAA1 | 3-ketoacyl-CoA thiolase, peroxisomal | 1.68 |
| FKBP11 | Peptidyl-prolyl cis-trans isomerase FKBP11 | 1.68 |
| RRM2B | Ribonucleoside-diphosphate reductase subunit M2 B | 1.68 |
| MLYCD | Malonyl-CoA decarboxylase, mitochondrial | 1.67 |
| ENDOG | Endonuclease G, mitochondrial | 1.67 |
| HPDL | 4-hydroxyphenylpyruvate dioxygenase-like protein | 1.67 |
| CYB5R1 | NADH-cytochrome b5 reductase 1 | 1.66 |
| KIF1A | Kinesin-like protein KIF1A | 1.66 |
| ENTPD8 | Ectonucleoside triphosphate diphosphohydrolase 8 | 1.66 |
| DLGAP4 | Disks large-associated protein 4 | 1.66 |
| IVD | Isovaleryl-CoA dehydrogenase, mitochondrial | 1.66 |
| MRPS18C | 28S ribosomal protein S18c, mitochondrial | 1.66 |
| CTSD | Cathepsin D | 1.66 |
| HIBCH | 3-hydroxyisobutyryl-CoA hydrolase, mitochondrial | 1.66 |
| HS1BP3 | HCLS1-binding protein 3 | 1.66 |
| MISP | Mitotic interactor and substrate of PLK1 | 1.66 |
| ANXA2 | Annexin A2 | 1.65 |
| CD44 | CD44 antigen | 1.65 |
| MSRB2 | Methionine-R-sulfoxide reductase B2, mitochondrial | 1.65 |
| GLB1 | Beta-galactosidase | 1.64 |
| CPD | Carboxypeptidase D | 1.64 |
| TACSTD2 | Tumor-associated calcium signal transducer 2 | 1.64 |
| COMTD1 | Catechol O-methyltransferase domain-containing protein 1 | 1.64 |
| RIN1 | Ras and Rab interactor 1 | 1.63 |
| CMAS | N-acylneuraminate cytidylyltransferase | 1.63 |
| NQO1 | NAD(P)H dehydrogenase [quinone] 1 | 1.63 |
| ERLEC1 | Endoplasmic reticulum lectin 1 | 1.63 |
| CDS2 | Phosphatidate cytidylyltransferase 2 | 1.63 |
| GLUD2 | Glutamate dehydrogenase 2, mitochondrial | 1.62 |
| VDAC1 | Voltage-dependent anion-selective channel protein 1 | 1.61 |
| TTC19 | Tetratricopeptide repeat protein 19, mitochondrial | 1.61 |
| SEMA3C | Semaphorin-3C | 1.61 |
| LRSAM1 | E3 ubiquitin-protein ligase LRSAM1 | 1.60 |
| ACOT13 | Acyl-coenzyme A thioesterase 13 | 1.60 |
| LXN | Latexin | 1.60 |
| GSN | Gelsolin | 1.60 |
| CHP1 | Calcineurin B homologous protein 1 | 1.60 |
| GALNT2 | N-acetylgalactosaminyltransferase 2 | 1.60 |
| RARS2 | Arginine-tRNA ligase, mitochondrial | 1.60 |
| PACS1 | Phosphofurin acidic cluster sorting protein 1 | 1.60 |
| RMDN3 | Regulator of microtubule dynamics protein 3 | 1.60 |
| PANK4 | Pantothenate kinase 4 | 1.59 |

TABLE 4-continued

Proteomic analysis of e-CSCs, derived from MCF7 3D-Spheroids

| Symbol | Gene Description | Fold-Change (Up-regulation) |
|---|---|---|
| KTN1 | Kinectin | 1.59 |
| CTSB | Cathepsin B | 1.58 |
| BCKDHA | 2-oxoisovalerate dehydrogenase subunit alpha, mitochondrial | 1.58 |
| EBAG9 | Receptor-binding cancer antigen expressed on SiSo cells | 1.58 |
| TMEM214 | Transmembrane protein 214 | 1.58 |
| UQCC2 | Ubiquinol-cytochrome-c reductase complex assembly factor 2, mitochondrial | 1.58 |
| TM9SF4 | Transmembrane 9 superfamily member 4 | 1.58 |
| HDHD2 | Haloacid dehalogenase-like hydrolase domain-containing protein 2 | 1.58 |
| EPHX1 | Epoxide hydrolase 1 | 1.58 |
| TMF1 | TATA element modulatory factor | 1.58 |
| CDIPT | CDP-diacylglycerol--inositol 3-phosphatidyltransferase | 1.57 |
| CD81 | CD81 antigen | 1.57 |
| SRXN1 | Sulfiredoxin-1 | 1.57 |
| ME1 | NADP-dependent malic enzyme | 1.57 |
| ACOT8 | Acyl-coenzyme A thioesterase 8, peroxisomal | 1.57 |
| SMDT1 | Essential MCU regulator, mitochondrial | 1.56 |
| ALG1 | Chitobiosyldiphosphodolichol beta-mannosyltransferase | 1.56 |
| DNAJC5 | DnaJ homolog subfamily C member 5 | 1.55 |
| DBT | Lipoamide acyltransferase component of branched-chain alpha-keto acid dehydrogenase complex, mitochondrial | 1.55 |
| LAMTOR2 | Ragulator complex protein LAMTOR2 | 1.54 |
| TIGAR | Fructose-2,6-bisphosphatase TIGAR | 1.54 |
| IDUA | Alpha-L-iduronidase | 1.54 |
| TMEM87B | Transmembrane protein 87B | 1.54 |
| TNKS1BP1 | 182 kDa tankyrase-1-binding protein | 1.54 |
| MIA3 | Transport and Golgi organization protein 1 homolog | 1.54 |
| TXNRD1 | Thioredoxin reductase 1, cytoplasmic | 1.54 |
| MYOF | Myoferlin | 1.54 |
| RABEP2 | Rab GTPase-binding effector protein 2 | 1.53 |
| GLUD1 | Glutamate dehydrogenase 1, mitochondrial | 1.53 |
| PDF | Peptide deformylase, mitochondrial | 1.53 |
| TAPBP | Tapasin | 1.53 |
| NDUFS7 | NADH dehydrogenase [ubiquinone] iron-sulfur protein 7, mitochondrial | 1.53 |
| ATP2C1 | Calcium-transporting ATPase type 2C member 1 | 1.53 |
| ANK3 | Ankyrin-3 | 1.53 |
| ABHD11 | Protein ABHD11 | 1.53 |
| AGO3 | Protein argonaute-3 | 1.53 |
| S100A16 | Protein S100-A16 | 1.53 |
| TM7SF2 | Delta(14)-sterol reductase | 1.53 |
| MRPL21 | 39S ribosomal protein L21, mitochondrial | 1.53 |
| RAB9A | Ras-related protein Rab-9A | 1.53 |
| TOM1 | Target of Myb protein 1 | 1.53 |
| C21orf33 | ES1 protein homolog, mitochondrial | 1.52 |
| SURF1 | Surfeit locus 1 (cytochrome c oxidase assembly protein), mitochondrial | 1.52 |
| NAMPT | Nicotinamide phosphoribosyltransferase | 1.51 |
| METTL7B | Methyltransferase-like protein 7B | 1.51 |
| CTSA | Cathepsin A | 1.51 |
| TTC37 | Tetratricopeptide repeat protein 37 | 1.51 |
| RIDA | 2-iminobutanoate/2-iminopropanoate deaminase | 1.50 |
| ARPC1A | Actin-related protein 2/3 complex subunit 1A | 1.50 |
| OS9 | Protein OS-9 | 1.50 |
| FUCA1 | Tissue alpha-L-fucosidase | 1.50 |

TABLE 5

Mitochondrial-related Proteins Up-regulated in e-CSCs, derived from MCF7 3D-Spheroids

| Symbol | Gene Description | Fold-Change (Up-regulation) |
|---|---|---|
| GLRX | Glutaredoxin-1 | 10.79 |
| ALDH3A1 | Aldehyde dehydrogenase, dimeric NADP-preferring | 10.24 |
| QPRT | Nicotinate-nucleotide pyrophosphorylase [carboxylating] | 3.72 |
| MIC13 | MICOS complex subunit MIC13, mitochondrial | 2.36 |
| OXSM | 3-oxoacyl-[acyl-carrier-protein] synthase, mitochondria | 2.22 |
| FECH | Ferrochelatase, mitochondrial | 2.16 |
| MCU | Calcium uniporter protein, mitochondrial | 2.13 |
| GCLC | Glutamate--cysteine ligase catalytic subunit | 2.01 |
| NQO2 | Ribosyldihydronicotinamide dehydrogenase [quinone] | 1.90 |
| CMC1 | COX assembly mitochondrial protein homolog | 1.87 |
| ISCU | Iron-sulfur cluster assembly enzyme ISCU, mitochondrial | 1.83 |
| ABAT | 4-aminobutyrate aminotransferase, mitochondrial | 1.81 |
| ABCB6 | ATP-binding cassette sub-family B member 6, mitochondrial | 1.80 |
| ACADSB | Short/branched chain specific acyl-CoA dehydrogenase, mitochondrial | 1.79 |
| COQ9 | Ubiquinone biosynthesis protein COQ9, mitochondrial | 1.77 |
| ALDH5A1 | Succinate-semialdehyde dehydrogenase, mitochondrial | 1.76 |
| CPT2 | Carnitine O-palmitoyltransferase 2, mitochondrial | 1.76 |
| HMGCL | Hydroxymethylglutaryl-CoA lyase, mitochondrial | 1.75 |
| FDXR | NADPH:adrenodoxin oxidoreductase, mitochondrial | 1.75 |
| CYCS | Cytochrome c | 1.74 |
| SQOR | Sulfide:quinone oxidoreductase, mitochondrial | 1.73 |
| HMOX1 | Heme oxygenase 1 | 1.69 |
| MLYCD | Malonyl-CoA decarboxylase, mitochondrial | 1.67 |
| ENDOG | Endonuclease G, mitochondrial | 1.67 |
| IVD | Isovaleryl-CoA dehydrogenase, mitochondrial | 1.66 |
| MRPS18C | 28S ribosomal protein S18c, mitochondrial | 1.66 |
| HIBCH | 3-hydroxyisobutyryl-CoA hydrolase, mitochondrial | 1.66 |
| MSRB2 | Methionine-R-sulfoxide reductase B2, mitochondrial | 1.64 |
| NQO1 | NAD(P)H dehydrogenase [quinone] 1 | 1.63 |
| GLUD2 | Glutamate dehydrogenase 2, mitochondrial | 1.62 |
| VDAC1 | Voltage-dependent anion-selective channel protein 1 | 1.61 |
| TTC19 | Tetratricopeptide repeat protein 19, mitochondrial | 1.61 |
| ACOT13 | Acyl-coenzyme A thioesterase 13, mitochondrial | 1.60 |
| RARS2 | Arginine-tRNA ligase, mitochondrial | 1.60 |
| BCKDHA | 2-oxoisovalerate dehydrogenase subunit alpha, mitochondrial | 1.58 |
| UQCC2 | Ubiquinol-cytochrome-c reductase complex assembly factor 2, Mitochondrial | 1.58 |
| ME1 | NADP-dependent malic enzyme | 1.57 |
| SMDT1 | Essential MCU regulator, mitochondrial | 1.56 |
| DNAJC5 | DnaJ homolog subfamily C member 5 | 1.55 |
| DBT | Lipoamide acyltransferase/branched-chain α-keto dehydrogenase, mitochondrial | 1.55 |
| TIGAR | Fructose-2,6-bisphosphatase TIGAR | 1.54 |
| GLUD1 | Glutamate dehydrogenase 1, mitochondrial | 1.53 |
| PDF | Peptide deformylase, mitochondrial | 1.53 |
| NDUFS7 | NADH dehydrogenase [ubiquinone] iron-sulfur protein 7, mitochondrial | 1.53 |
| MRPL21 | 39S ribosomal protein L21, mitochondrial | 1.53 |
| C21orf33 | ES1 protein homolog, mitochondrial | 1.52 |
| SURF1 | Surfeit locus 1 (cytochrome c oxidase assembly protein),Mitochondrial | 1.52 |
| NAMPT | Nicotinamide phosphoribosyltransferase | 1.51 |

TABLE 6

Functional Markers of the e-CSC Phenotype (from MCF7 3D-Spheroids)

| Symbol | Gene Description | Fold-Change (Up-regulation) |
|---|---|---|
| Senescence Markers | | |
| CDKN1A | Cyclin-dependent kinase inhibitor 1 (p21-WAF/CDK-inhibitor) | 17.22 |
| GLB1 | Beta-galactosidase | 1.64 |
| Anti-Oxidant Response to ROS/Oxidative Stress | | |
| GLRX | Glutaredoxin-1 | 10.79 |
| GCLC | Glutamate--cysteine ligase catalytic subunit | 2.01 |
| NQO2 | Ribosyldihydronicotinamide dehydrogenase [quinone] | 1.90 |
| MGST1 | Microsomal glutathione S-transferase 1 | 1.88 |
| MGST3 | Microsomal glutathione S-transferase 3 | 1.84 |
| SPATA20 | Spermatogenesis-associated protein 20 (thioredoxin-like) | 1.77 |
| GSTK1 | Glutathione S-transferase kappa 1 | 1.75 |
| NQO1 | NAD(P)H dehydrogenase [quinone] 1 | 1.63 |
| Stemness & Drug-Resistance/Radio-Resistance | | |
| BCAS1 | Breast carcinoma-amplified sequence 1 | 119.37 |
| ALDH3A1 | Aldehyde dehydrogenase, dimeric NADP-preferring | 10.24 |
| CEACAM6 | Carcinoembryonic antigen-related cell adhesion molecule 6 | 9.66 |
| CEACAM5 | Carcinoembryonic antigen-related cell adhesion molecule 5 | 3.38 |
| LAMA5 | Laminin subunit alpha-5 | 2.72 |
| ALDH5A1 | Succinate-semialdehyde dehydrogenase, mitochondrial | 1.76 |
| CD44 | CD44 antigen | 1.65 |
| Cytoskeletal Proteins (indicative of an EMT in CSCs) | | |
| TUBA4A | Tubulin alpha-4A chain | 2.60 |
| STOM | Erythrocyte band 7 integral membrane protein | 2.18 |
| MAPRE3 | Microtubule-associated protein RP/EB family member 3 | 1.74 |
| KIF1A | Kinesin-like protein KIF1A | 1.66 |
| RMDN3 | Regulator of microtubule dynamics protein 3 | 1.60 |
| GSN | Gelsolin | 1.60 |
| MYOF | Myoferlin | 1.54 |
| ANK3 | Ankyrin-3 | 1.53 |
| ARPC1A | Actin-related protein 2/3 complex subunit 1A | 1.50 |
| Spindle Orientation and Mitotic Progression | | |
| MISP | Mitotic interactor and substrate of PLK1 | 1.66 |
| Mitochondrial Biogenesis | | |
| GLRX | Glutaredoxin-1 | 10.79 |
| MIC13 | MICOS complex subunit MIC13, mitochondrial | 2.36 |
| OXSM | 3-oxoacyl-[acyl-carrier-protein] synthase, mitochondrial | 2.22 |
| FECH | Ferrochelatase, mitochondrial | 2.16 |
| CMC1 | COX assembly mitochondrial protein homolog | 1.87 |
| ISCU | Iron-sulfur cluster assembly enzyme ISCU, mitochondrial | 1.83 |
| COQ9 | Ubiquinone biosynthesis protein COQ9, mitochondrial | 1.77 |
| HMOX1 | Heme oxygenase 1 | 1.69 |
| UQCC2 | Ubiquinol-cytochrome-c reductase complex assembly factor 2, Mitochondrial | 1.58 |
| MRPS18C | 28S ribosomal protein S18c, mitochondrial | 1.66 |
| RARS2 | Arginine-tRNA ligase, mitochondrial | 1.60 |
| MRPL21 | 39S ribosomal protein L21, mitochondrial | 1.53 |
| PDF | Peptide deformylase, mitochondrial | 1.53 |
| Glutamine/Asparagine Metabolism | | |
| AGA | N(4)-(beta-N-acetylgluco saminyl)-L-asparaginase | 2.30 |
| GLUD2 | Glutamate dehydrogenase 2, mitochondrial | 1.62 |
| GLUD1 | Glutamate dehydrogenase 1, mitochondrial | 1.53 |
| NADH/NADPH: Synthesis & Salvage Pathway | | |
| ALDH3A1 | Aldehyde dehydrogenase, dimeric NADP-preferring | 10.24 |
| QPRT | Nicotinate-nucleotide pyrophosphorylase [carboxylating] | 3.72 |
| RRM2 | Ribonucleoside-diphosphate reductase subunit M2 | 2.34 |
| ALDH5A1 | Succinate-semialdehyde dehydrogenase, mitochondrial | 1.76 |
| FDXR | NADPH:adrenodoxin oxidoreductase, mitochondrial | 1.75 |
| RRM2B | Ribonucleoside-diphosphate reductase subunit M2 B | 1.68 |
| ME1 | NADP-dependent malic enzyme | 1.57 |
| TIGAR | Fructose-2,6-bisphosphatase TIGAR | 1.54 |
| TNKS1BP1 | 182 kDa tankyrase-1-binding protein | 1.54 |
| NDUFS7 | NADH dehydrogenase [ubiquinone] iron-sulfur protein 7, mitochondrial | 1.53 |
| NAMPT | Nicotinamide phosphoribosyltransferase | 1.51 |
| Flavin-containing Enzymes | | |
| CYP1A1 | Cytochrome P450 1A1 | 6.60 |
| MAOA | Amine oxidase [flavin-containing] A | 4.73 |
| MAOB | Amine oxidase [flavin-containing] B | 2.45 |
| GFER | FAD-linked sulfhydryl oxidase ALR | 1.80 |
| CYB5R1 | NADH-cytochrome b5 reductase 1 | 1.66 |
| TXNRD1 | Thioredoxin reductase 1, cytoplasmic (Glutaredoxin activity; flavin-dependent) | 1.54 |
| Epithelial Markers | | |
| KRT10 | Keratin, type I cytoskeletal 10 | 4.59 |
| DPP7 | Dipeptidyl peptidase 2 | 2.43 |
| MUC5B | Mucin-5B | 1.98 |
| Cell Surface Markers | | |
| GM2A | Ganglioside GM2 activator | 2.36 |
| CD59 | CD59 glycoprotein | 1.80 |
| ENTPD8 | Ectonucleoside triphosphate diphosphohydrolase 8 | 1.66 |
| CD81 | CD81 antigen | 1.57 |
| S100 Proteins | | |
| S100P | Protein S100-P | 2.11 |
| S100A10 | Protein S100-A10 | 1.96 |
| S100A16 | Protein S100-A16 | 1.53 |
| Autophagy/Lysosomes | | |
| CHMP6 | Charged multivesicular body protein 6 | 2.62 |
| SERPINA3 | Alpha-1-antichymotrypsin | 2.33 |
| CTSH | Cathepsin H | 1.98 |
| GNS | N-acetylglucosamine-6-sulfatase | 1.97 |
| GAA | Lysosomal alpha-glucosidase | 1.83 |
| GALNS | N-acetylgalactosamine-6-sulfatase | 1.82 |
| ATP6V0A1 | V-type proton ATPase 116 kDa subunit a isoform 1 | 1.71 |
| CTSD | Cathepsin D | 1.66 |
| CPD | Carboxypeptidase D | 1.64 |
| GALNT2 | N-acetylgalactosaminyltransferase 2 | 1.60 |
| CTSB | Cathepsin B | 1.58 |
| CTSA | Cathepsin A | 1.51 |
| Peroxisomes | | |
| PEX14 | Peroxisomal membrane protein PEX14 | 1.91 |
| DECR2 | Peroxisomal 2,4-dienoyl-CoA reductase | 1.81 |
| PEX11B | Peroxisomal membrane protein PEX11B | 1.76 |
| ACOT8 | Acyl-coenzyme A thioesterase 8, peroxisomal | 1.57 |
| RABs | | |
| RAB27B | Ras-related protein Rab-27B | 2.69 |
| RAB27A | Ras-related protein Rab-27A | 2.54 |
| RAB24 | Ras-related protein Rab-24 | 1.87 |

TABLE 6-continued

Functional Markers of the e-CSC Phenotype (from MCF7 3D-Spheroids)

| Symbol | Gene Description | Fold-Change (Up-regulation) |
|---|---|---|
| RIN1 | Ras and Rab interactor 1 | 1.63 |
| RABEP2 | Rab GTPase-binding effector protein 2 | 1.53 |
| RAB9A | Ras-related protein Rab-9A | 1.53 |
| Annexins and PARP | | |
| ANXA1 | Annexin A1 | 2.87 |
| PARP4 | Poly [ADP-ribose] polymerase 4 | 2.55 |
| ANXA2 | Annexin A2 | 1.65 |
| Calcium/Calmodulin | | |
| CIB1 | Calcium and integrin-binding protein 1 | 2.90 |
| MCU | Calcium uniporter protein, mitochondrial | 2.13 |
| CAPS | Calcyphosin | 1.79 |
| CAMK2D | Calcium/calmodulin-dependent protein kinase, type II subunit delta | 1.70 |
| CALML5 | Calmodulin-like protein 5 | 1.69 |
| TACSTD2 | Tumor-associated calcium signal transducer 2 | 1.64 |
| CHP1 | Calcineurin B homologous protein 1 | 1.60 |
| SMDT1 | Essential MCU regulator, mitochondrial | 1.56 |
| ATP2C1 | Calcium-transporting ATPase type 2C member 1 | 1.53 |

TABLE 7 eCSC Marker Proteins are Transcriptionally Up-regulated in Patient-derived Human Breast Cancer Cells In Vivo

| Symbol | Gene Description | Fold-Change | P-value |
|---|---|---|---|
| TSPAN31 | Tetraspanin-31 | 4.72 | 8.45E−06 |
| CDS2 | Phosphatidate cytidylyltransferase 2 | 4.71 | 8.73E−06 |
| PEX11B | Peroxisomal membrane protein PEX11B | 4.69 | 9.58E−06 |
| RAB9A | Ras-related protein Rab-9A | 4.47 | 2.02E−05 |
| TACSTD2 | Tumor-associated calcium signal transducer 2 | 4.41 | 2.47E−05 |
| GLUD1 | Glutamate dehydrogenase 1, mitochondrial | 4.38 | 2.76E−05 |
| MSRB2 | Methionine-R-sulfoxide reductase B2, mitochondrial | 4.31 | 3.49E−05 |
| SURF1 | Surfeit locus 1 (cytochrome c oxidase assembly protein), mitochondrial | 4.16 | 5.66E−05 |
| PON2 | Serum paraoxonase/arylesterase 2 | 4.01 | 9.25E−05 |
| CYB5R1 | NADH-cytochrome b5 reductase 1 | 3.94 | 1.18E−04 |
| ANK3 | Ankyrin-3 | 3.81 | 1.77E−04 |
| ASAH1 | Acid ceramidase | 3.80 | 1.83E−04 |
| CD59 | CD59 glycoprotein | 3.60 | 3.47E−04 |
| OXSM | 3-oxoacyl-[acyl-carrier-protein] synthase, mitochondrial | 3.49 | 4.82E−04 |
| NQO1 | NAD(P)H dehydrogenase [quinone] 1 | 3.49 | 4.81E−04 |
| SEMA3C | Semaphorin-3C | 3.49 | 4.92E−04 |
| CD44 | CD44 antigen | 3.44 | 5.69E−04 |
| ALDH5A1 | Succinate-semialdehyde dehydrogenase, mitochondrial | 3.43 | 5.75E−04 |
| AGA | N(4)-(beta-N-acetylglucosaminyl)-L-asparaginase | 3.40 | 6.30E−04 |
| GSTK1 | Glutathione S-transferase kappa 1 | 3.39 | 6.59E−04 |
| KTN1 | Kinectin | 3.36 | 7.16E−04 |
| FECH | Ferrochelatase, mitochondrial | 3.36 | 7.20E−04 |
| C21orf33 | ES1 protein homolog, mitochondrial | 3.31 | 8.40E−04 |
| MPV17 | Protein Mpv17 | 3.27 | 9.44E−04 |
| TMEM214 | Transmembrane protein 214 | 3.12 | 1.44E−03 |
| NEBL | Nebulette | 3.09 | 1.59E−03 |
| CDIPT | CDP-diacylglycerol--inositol 3-phosphatidyltransferase | 3.06 | 1.74E−03 |
| CPT2 | Carnitine O-palmitoyltransferase 2, mitochondrial | 3.02 | 1.94E−03 |
| ATP2C1 | Calcium-transporting ATPase type 2C member 1 | 3.01 | 1.96E−03 |
| SERPINA3 | Alpha-1-antichymotrypsin | 2.99 | 2.11E−03 |
| CYCS | Cytochrome c | 2.92 | 2.52E−03 |
| TTC19 | Tetratricopeptide repeat protein 19, mitochondrial | 2.85 | 3.06E−03 |
| SELENBP1 | Methanethiol oxidase | 2.84 | 3.22E−03 |
| MIA3 | Transport and Golgi organization protein 1 homolog | 2.76 | 3.98E−03 |
| OS9 | Protein OS-9; amplified in osteosarcoma | 2.76 | 3.99E−03 |
| ANXA2 | Annexin A2 | 2.73 | 4.30E−03 |
| SULT1A1 | Sulfotransferase 1A1 | 2.72 | 4.34E−03 |
| MYOF | Myoferlin | 2.67 | 5.00E−03 |
| CAPN2 | Calpain-2 catalytic subunit | 2.64 | 5.42E−03 |
| VDAC1 | Voltage-dependent anion-selective channel protein 1, mitochondrial | 2.64 | 5.35E−03 |
| TXNRD1 | Thioredoxin reductase 1, cytoplasmic | 2.64 | 5.36E−03 |
| EPS8L1 | Epidermal growth factor receptor kinase substrate 8-like protein 1 | 2.57 | 6.54E−03 |
| PDF | Peptide deformylase, mitochondrial | 2.56 | 6.71E−03 |
| CTSH | Cathepsin H | 2.54 | 7.07E−03 |
| KRT10 | Keratin, type I cytoskeletal 10 | 2.53 | 7.19E−03 |
| GLB1 | Beta-galactosidase | 2.53 | 7.20E−03 |
| GM2A | Ganglioside GM2 activator | 2.42 | 9.42E−03 |
| RRM2 | Ribonucleoside-diphosphate reductase subunit M2 | 2.40 | 9.93E−03 |
| RETSAT | All-trans-retinol 13,14-reductase | 2.39 | 1.03E−02 |
| RNASET2 | Ribonuclease T2 | 2.36 | 1.10E−02 |
| ENDOG | Endonuclease G, mitochondrial | 2.32 | 1.22E−02 |
| NAMPT | Nicotinamide phosphoribosyltransferase | 2.19 | 1.66E−02 |
| SPATA20 | Spermatogenesis-associated protein 20 | 2.16 | 1.77E−02 |
| SLC22A18 | Solute carrier family 22 member 18 | 2.14 | 1.86E−02 |
| ABAT | 4-aminobutyrate aminotransferase, mitochondrial | 2.08 | 2.14E−02 |
| TAPBP | Tapasin | 2.08 | 2.13E−02 |
| CIB1 | Calcium and integrin-binding protein 1 | 2.04 | 2.34E−02 |
| HMGCL | Hydroxymethylglutaryl-CoA lyase, mitochondrial | 2.03 | 2.38E−02 |
| FAM8A1 | Protein FAM8A1 | 2.02 | 2.40E−02 |
| GCLC | Glutamate--cysteine ligase catalytic subunit | 2.01 | 2.49E−02 |
| ACAA1 | 3-ketoacyl-CoA thiolase, peroxisomal | 2.00 | 2.53E−02 |
| GLRX | Glutaredoxin-1 | 1.92 | 3.01E−02 |
| ISCU | Iron-sulfur cluster assembly enzyme ISCU, mitochondrial | 1.92 | 3.02E−02 |
| TMF1 | TATA element modulatory factor | 1.88 | 3.25E−02 |
| CD81 | CD81 antigen | 1.87 | 3.34E−02 |
| NQO2 | Ribosyldihydronicotinamide dehydrogenase [quinone] | 1.79 | 3.98E−02 |
| MAOB | Amine oxidase [flavin-containing] B | 1.74 | 4.41E−02 |
| CEACAM6 | Carcinoembryonic antigen-related cell adhesion molecule 6 | 1.70 | 4.71E−02 |
| SLC9A1 | Sodium/hydrogen exchanger 1 | 1.68 | 4.97E−02 |

TABLE 8

Tumor Recurrence (RFS): Predicting Tamoxifen-resistance in ER( + ) Breast Cancer Patients

| Gene Probe | Gene Symbol | HR (Hazard-Ratio) | Log-Rank Test |
|---|---|---|---|
| 201468_s_at | NQO1 | 2.47 | 0.0023 |
| 203608_at | ALDH5A1 | 2.21 | 0.01 |
| 201266_at | TXNR | 2.17 | 0.0062 |

TABLE 8-continued

Tumor Recurrence (RFS): Predicting
Tamoxifen-resistance in ER( + ) Breast
Cancer Patients

| Gene Probe | Gene Symbol | HR (Hazard-Ratio) | Log-Rank Test |
|---|---|---|---|
| 201890_at | RRM2 | 2.54 | 0.00089 |
| Combined Signature (RFS) | | 3.89 | 4.1e−05 |

RFS, recurrence-free survival.

TABLE 9

Distant Metastasis (DMFS): Predicting Tamoxifen-resistance in ER(+) Breast Cancer Patients

| Gene Probe | Gene Symbol | HR (Hazard-Ratio) | Log-Rank Test |
|---|---|---|---|
| 201468_s_at | NQO1 | 1.73 | 0.1 |
| 203608_at | ALDH5A1 | 2.86 | 0.0034 |
| 201266_at | TXNR | 3.64 | 0.00035 |
| 201890_at | RRM2 | 3.02 | 0.00092 |

DMFS, distant metastasis-free survival.

What is claimed is:

1. A method for identifying and treating energetic cancer stem cells (e-CSCs) in a breast cancer, the method comprising:
obtaining a biological sample of the breast cancer;
determining, or having determined, a level of expression of at least one of a protein or mRNA transcript, of each member of an e-CSC gene signature comprising aldehyde dehydrogenase 5 family member A1 (ALDH5A1), thioredoxin reductase 1 (TXNR), and ribonucleotide-diphosphate reductase subunit M2 (RRM2);
comparing the determined level to a threshold level from a healthy cell line for each member of the e-CSC gene signature;
administering a pharmaceutically effective amount of at least one of an oxidative phosphorylation (OXPHOS) inhibitor and a cyclin-dependent kinase 4/6 (CDK4/6) inhibitor if the determined level exceeds the threshold level, wherein the OXPHOS inhibitor inhibits mitochondrial function and biogenesis and the CDK4/6 inhibitor inhibits cell proliferation.

2. The method of claim 1, wherein the gene signature comprises NAD(P)H quinone dehydrogenase 1 (NQO1), ALDH5A1, TXNR and RRM2.

3. The method of claim 1, wherein the at least one of an OXPHOS inhibitor and a CDK4/6 inhibitor comprises diphenyleneiodonium chloride (DPI).

4. The method of claim 1, wherein the at least one of an OXPHOS inhibitor and a CDK4/6 inhibitor comprises Ribociclib.

5. The method of claim 1, wherein the at least one of an OXPHOS inhibitor and a CDK4/6 inhibitor is selected from the group consisting of DPI, atovaquone, irinotecan, sorafenib, niclosamide, berberine chloride, Ribociclib, Abemaciclib, and Palbociclib.

6. The method of claim 1, wherein the pharmaceutically effective amount of at least one of an OXPHOS inhibitor and a CDK4/6 inhibitor is administered if the quotient of the determined level divided by the threshold level is greater than 1.2.

7. A method for treating tumor recurrence in a breast cancer, the method comprising:
obtaining a biological sample of the breast cancer;
performing an assay to detect the presence of e-CSCs in the biological sample using an e-CSC gene signature comprising ALDH5A1, TXNR, and RRM2, wherein the assay comprises measuring a level of expression of at least one of a protein or mRNA transcript, of each member of the e-CSC gene signature in the biological sample, and e-CSCs are detected if the measured level of expression of each member of the e-CSC gene signature exceeds a threshold level from a healthy cell line for each member of the e-CSC gene signature;
administering a pharmaceutically effective amount of at least one of an OXPHOS inhibitor and a CDK4/6 inhibitor if e-CSCs are detected in the biological sample, wherein the OXPHOS inhibitor inhibits mitochondrial function and biogenesis and the CDK4/6 inhibitor inhibits cell proliferation.

8. The method of claim 7, wherein the gene signature comprises NQO1, ALDH5A1, TXNR, and RRM2.

9. The method of claim 8, wherein the at least one of an OXPHOS inhibitor and a CDK4/6 inhibitor comprises diphenyleneiodonium chloride (DPI).

10. The method of claim 8, wherein the at least one of an OXPHOS inhibitor and a CDK4/6 inhibitor comprises Ribociclib.

11. The method of claim 8, wherein the at least one of an OXPHOS inhibitor and a CDK4/6 inhibitor comprises at least one of DPI, atovaquone, irinotecan, sorafenib, niclosamide, berberine chloride, Ribociclib, Abemaciclib, and Palbociclib.

12. The method of claim 8, wherein the threshold level comprises a level of the at least one member from a non-cancerous biological sample.

13. The method of claim 8, wherein the pharmaceutically effective amount of at least one of an OXPHOS inhibitor and a CDK4/6 inhibitor is administered if the quotient of the determined level divided by the threshold level is greater than 1.2.

14. The method of claim 8, wherein the cancer exists in a tumor that has been treated with hormone therapy.

15. A method for treating breast cancer having one or more e-CSCs, the method comprising:
obtaining a biological sample of the breast cancer;
performing an assay to detect the presence of e-CSCs in the biological sample using an e-CSC gene signature comprising ALDH5A1, TXNR, and RRM2, wherein the assay comprises measuring a level of expression of at least one of a protein or mRNA transcript, of each member of the e-CSC gene signature in the biological sample, and e-CSCs are detected if the measured level of expression of each member of the e-CSC gene signature exceeds a threshold level from a healthy cell line for each member of the e-CSC gene signature;
administering a pharmaceutically effective amount of at least one of an OXPHOS inhibitor and a CDK4/6 inhibitor if e-CSCs are detected in the biological sample, wherein the OXPHOS inhibitor inhibits mitochondrial function and biogenesis and the CDK4/6 inhibitor inhibits cell proliferation.

16. The method of claim 15, wherein the gene signature comprises NQO1, ALDH5A1, TXNR and RRM2.

17. The method of claim 15, wherein the at least one of an OXPHOS inhibitor and a CDK4/6 inhibitor comprises diphenyleneiodonium chloride (DPI).

18. The method of claim 15, wherein the at least one of an OXPHOS inhibitor and a CDK4/6 inhibitor comprises Ribociclib.

19. The method of claim 15, wherein the at least one of an OXPHOS inhibitor and a CDK4/6 inhibitor is selected from the group consisting of DPI, atovaquone, irinotecan, sorafenib, niclosamide, berberine chloride, Ribociclib, Abemaciclib, and Palbociclib.

20. The method of claim 15, wherein the threshold level comprises a level of the at least one member from a non-cancerous biological sample.

21. The method of claim 15, wherein the pharmaceutically effective amount of at least one of an OXPHOS inhibitor and a CDK4/6 inhibitor is administered if the quotient of the determined level divided by the threshold level is greater than 1.2.

22. The method of claim 15, wherein the cancer exists in a tumor that has been treated with hormone therapy.

23. The method of claim 15, wherein the breast cancer comprises at least one of a benign lesion, a pre-malignant lesion, a malignant lesion, and a metastatic lesion.

24. The method of claim 15, further comprising administering a pharmaceutically effective amount of at least one mitochondrial inhibitor if e-CSCs are detected in the biological sample.

25. The method of claim 15, wherein the mitochondrial inhibitor comprises at least one of a mitoriboscin, a mitoketoscin, a antimitoscin, a repurposcin, a mitoflavoscin, metformin, a tetracycline family member, a tigecycline family member, a erythromycin family member, atovaquone, bedaquiline, vitalin c, stiripentol, caffeic acid phenyl ester (CAPE), and berberine.

* * * * *